United States Patent [19]
De Mesmaeker et al.

[11] Patent Number: 6,066,447
[45] Date of Patent: *May 23, 2000

[54] MODIFIED OLIGONUCLEOTIDES

[75] Inventors: Alain De Mesmaeker, Känerkinden; Adrian Waldner, Allschwil, both of Switzerland; Jacques Lebreton, Marseilles, France; Marc-Olivier Bevierre, Fontainebleau, France; Cathérine Lesueur, Chambray-lès-Tours, France

[73] Assignee: Novartis Corporation, Summit, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/687,456
[22] PCT Filed: Jan. 17, 1995
[86] PCT No.: PCT/EP95/00156
§ 371 Date: Nov. 12, 1996
§ 102(e) Date: Nov. 12, 1996
[87] PCT Pub. No.: WO95/20597
PCT Pub. Date: Aug. 3, 1995

[30] Foreign Application Priority Data

Jan. 26, 1994 [GB] United Kingdom .................... 9401446
Jun. 22, 1994 [GB] United Kingdom .................... 9412526

[51] Int. Cl.$^7$ ..................................................... C12Q 1/68
[52] U.S. Cl. .................................. 435/5; 435/6; 436/501; 514/44; 536/22.1; 536/24.1; 536/24.3; 536/24.31; 536/24.32; 536/24.33; 536/25.3
[58] Field of Search ................................... 435/6, 810, 5; 436/501; 536/22.1, 23.1, 24.1, 25.3, 24.3–24.33; 935/77, 78; 514/44

[56] References Cited

FOREIGN PATENT DOCUMENTS

| 0266099 | 5/1988 | European Pat. Off. . |
| 8707300 | 12/1987 | WIPO . |
| 8908146 | 9/1989 | WIPO . |
| 9106556 | 5/1991 | WIPO . |
| 9202534 | 2/1992 | WIPO . |
| 9205186 | 4/1992 | WIPO . |
| 9220822 | 11/1992 | WIPO . |
| 9220823 | 11/1992 | WIPO . |

OTHER PUBLICATIONS

Idziak et al., Tetrahedron Letters, vol. 34, No. 34, pp. 5417–5420, 1993.
Uhlmann, E. et al, Chemical Reviews 90 (1990) pp. 543–584.
Marquez, V. E. et al., Medicinal Research Reviews 6 (1986), pp. 1–40.
Helene, C. et al. Biochimica. et Biophysica Acta 1049 (1990), pp. 99–125.
English, U. et al., Angew. Chemic Int. Ed. Engl. 30 (1991), pp. 613–629.
Matteucci, M.D. et al., Ann. Rep. in Medicinal Chemistry 26 (1991), pp. 287–296.
De Mesmaeker, A. et al., Angew Chem. Int. Ed. Engl. 33 (1994), pp. 226–229.
Pudlo, J.S. et al., Tetrahedron Letters 31 (1990), pp. 3101–3104.
Codington, J.F. et al., J. Org. Chem. 29 (1964), pp. 558–564.
Pieles, U. et al. Nucleic Acids Res. 21 (1993), pp. 3191–3196.
Freier, S.M. et al. Biopolymers 22 (1983), pp. 1107–1131.
Hoke, G.D. et al., Nucleic Acids Res. 19 (1991), pp. 5743–5748.
Greene, B.T. "Protective Groups in Organic Synthesis," Wiley Interscience, New York (1991), pp. 1–142.
Gait, M.J. "Oligonucleitde Synthesis: A Practical Approach," 1RL Press, Oxford (1984).

*Primary Examiner*—Ardin H. Harschel
*Attorney, Agent, or Firm*—Gregory D. Ferraro

[57] ABSTRACT

Oligonucleotides of the formula: 5'(U)$_n$–3' in which U is an identical or different radical of a natural or a synthetic nucleoside and n is a number from 2 to 200 comprising at least one structural unit of two consecutive nucleosides wherein one of the nucleotides is substituted in the 2'-position or wherein the nucleotides are substituted differently in their 2'-position and wherein the backbone is modified.

45 Claims, No Drawings

MODIFIED OLIGONUCLEOTIDES

The present invention relates to modified oligonucleotides comprising at least one nucleotide dimer with a modified backbone, to the modified nucleotide dimers, processes for the preparation of the modified oligonucleotides or the nucleotide dimers, the use of the modified oligonucleotides or the nucleotide dimers and pharmaceutical preparations containing the modified oligonucleotides.

Nucleosides and oligonucleotides have required wide interest as antiviral active ingredients or because of their capability to interact with nucleic acids ("antisense" oligonucleotides) and the biological activity associated therewith, see, for example, Uhlmann, E., Peyman, A., Chemical Reviews 90:543–584 (1990). To provide nucleosides having novel properties or to improve the interaction of antisense oligonucleotides with natural nucleic acids and their stability to nucleases, the sugar radicals of nucleosides (or the nucleotide units in oligonucleotides) or the internucleotide phosphate bond in oligonucleotides have been modified in very different ways, see, for example, Marquez, V. E., Lim. M-I., Medicinal Research Reviews 6:1–40 (1986), Hélène, C., Toulmé, J. J., Biochimica et Biophysica Acta 1049:99–125 (1990), Englisch, U., Gauss, D. H., Angewandte Chemie 103:629–646 (1991), Matteucci, M.D., Bischofberger, N., Annual Reports in Medicinal Chemistry 26:287–296 (1991) and WO 91/06556.

In WO 92/20823 backbone modified oligonucleotide analogs are disclosed wherein the phosphodiester inter-sugar linkages found in wild type oligomers are replaced with four atom linking groups and identical 2'-substituents. WO 92/05186 discloses modified oligonucleotides wherein the phosphodiester linkages are replaced by a two to four atom long internucleoside linkage wherein at least one of the atoms is nitrogen, oxygen or sulfur and wherein the substituents in 2'-position may be different. Exemplified are linkages wherein the hetero atom is in 3'-position of the sugar and dimers wherein both nucleosides are unsubstituted.

The hybridization characteristics with DNA/RNA and the resistence to nucleases of the so modified oligonucleotides are, however, not satisfying.

Surprisingly it was found that oligonucleotides which are highly resistant to nucleases and capable of strong hybridization to target RNA or DNA can be obtained by incorporating into the oligonucleotides nucleotide dimers wherein only one of the two 2'-positions is substituted or wherein the 2'-positions are substituted differently, and wherein the phosphodiester linkage is formed by a four membered amide or butylene group.

It is an object of the present invention to provide an oligonucleotide of the formula I $$5'—(U)_n-3' \qquad (I)$$

in which U is an identical or different radical of a natural or a synthetic nucleoside and n is a number from 2 to 200, preferably 2 to 100, more prefered 2 to 50 and most prefered 2 to 20 monomer units, comprising at least one structural unit of two consecutive nucleosides, the structural unit comprising the formula IIa, IIb, IIc or IId

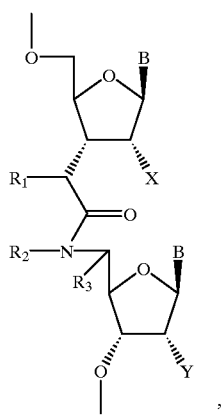

(IIa)

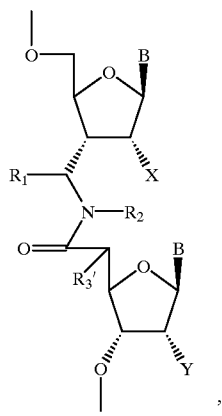

(IIb)

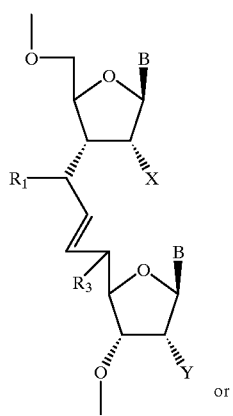

(IIc)

or

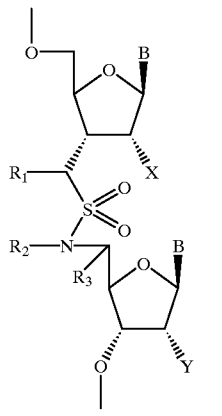

(IId)

wherein $R_1$ is H, $C_1$–$C_4$alkyl or $C_1$–$C_4$alkoxy; $R_2$ is H; $C_1$–$C_4$alkyl; phenyl; phenyl substituted with OH, OR''', O($CH_2CH_2O)_n$R''', $C_6$–$C_{10}$aryl or $C_3$–$C_9$heteroaryl; an intercalator; amino-$C_1$–$C_4$alkyl; $C_1$–$C_4$alkylamino; ammonium-$C_1$–$C_4$alkyl; $C_1$–$C_4$alkylammonium; amino-$C_1$–$C_4$alkylaminosulfonyl; $C_1$–$C_4$alkylamino-$C_1$–$C_4$alkylaminosulfonyl or ($CH_3)_2NCH_2CH_2$; $R_3$ is H or $C_1$–$C_4$alkyl; $R_3'$ is H; OH; $C_1$–$C_4$alkyl; O—$C_1$–$C_4$alkyl; O($CH_2CH_2O)_n$R'''; R''' is $C_1$–$C_4$alkyl; X is H, OH, O—$C_1$–$C_4$alkyl, —O—($CH_2$—$CH_2$—O$)_m$H or —O—$CH_2$—C(OR)H—$CH_2$—OH; Y is H, O—$C_1$–$C_4$alkyl, —O—($CH_2$—$CH_2$—O$)_m$H or —O—$CH_2$—C(OR)H—$CH_2$—OH; R is H or $C_1$–$C_{10}$alkyl; m is an integer from 1 to 4; n is an integer from 1 to 4 and B is a purine or pyrimidine radical or an analogue thereof with the proviso that either X or Y is H or that X and Y are not identical.

Some examples of alkyl, alkoxy, alkylthio, hydroxyalkyl and aminoalkyl, which preferably contain 1 to 6 C atoms, are methyl, ethyl and the isomers of propyl, butyl, pentyl, hexyl, heptyl, octyl, nonyl, decyl, undecyl and dodecyl, and also corresponding alkoxy, alkylthio, hydroxyalkyl and aminoalkyl radicals. The alkyl, alkoxy, alkylthio, hydroxy-alkyl and aminoalkyl radicals preferably contain 1 to 4 C atoms. Preferred alkyl, alkoxy, alkylthio, hydroxyalkyl and aminoalkyl radicals are methyl, ethyl, n- and i-propyl, n-, i- and t-butyl, methoxy, ethoxy, methylthio and ethylthio, aminomethyl, aminoethyl, hydroxymethyl and hydroxy-ethyl.

Examples of aminoalkyl are aminomethyl, aminoethyl, 1-aminoprop-2-yl or —3—yl, 1-aminobut-2-yl or 3-yl or -4-yl, N-methyl- or N,N-dimethyl- or N-ethyl- or N,N-deithyl- or N-2-hydroxyethyl- or N,N,-di-2-hydroxyethylaminomethyl or -aminoethyl or -aminopropyl or -aminobutyl. Examples of hydroxyalkyl are hydroxymethyl, 1-hydroxyeth-2-yl, 1-hydroxyprop-2- or -3-yl, 1-hydroxbut-2-yl, -3-yl or -4-yl.

Examples of $C_6$–$C_{10}$aryl are naphythyl and phenyl, phenyl is preferred. The heteroaryl preferably contains 1 to 3 heteroatoms selected from the group consisting of O, S and N.

A preferred intercalator in connection with the present invention is anthraquinone substituted by a linker, the linker being preferably a chain of 2 to 7 atoms selected from the group consisting of C, N and O.

If B is a purine radical or an analogue thereof, it can be a radical of the formula IV, IVa, IVb, IVc, IVd or IVe

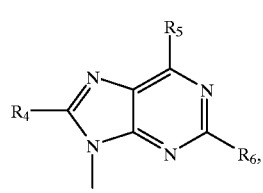

(IV)

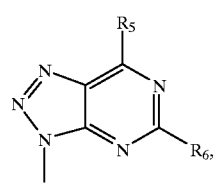

(IVa)

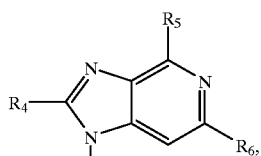

(IVb)

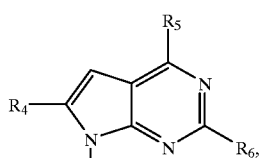

(IVc)

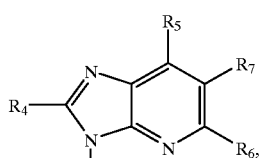

(IVd)

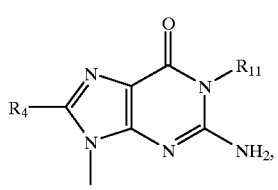

(IVe)

in which $R_4$ is H, Cl, Br or OH or —O—alkyl having 1 to 12 C atoms, and $R_5$, $R_6$ and $R_7$ independently of one another are H, OH, SH, $NH_2$, $NHNH_2$, NHOH, NHOalkyl having 1 to 12 C atoms, —N=CH—N($C_1$–$C_{12}$alkyl$)_2$, F, Cl, Br, alkyl or hydroxyalkyl or aminoalkyl or alkoxy or alkylthio having 1 to 12 C atoms, the hydroxyl and amino groups being unsubstituted or substituted by a protective group, phenyl, benzyl, primary amino having 1 to 20 C atoms or secondary amino having 2 to 30 C atoms, and $R_{11}$ is H or $C_1$–$C_4$alkyl.

Protective groups and processes for derivatisation of the hydroxyl groups with such protective groups are generally known in sugar and nucleotide chemistry and described, for example, by B. T. Greene, Protective Groups in Organic Synthesis, Wiley Interscience, New York (1991). Examples of such protective groups are: linear or branched $C_1$–$C_8$alkyl, particularly $C_1$–$C_4$alkyl, for example methyl, ethyl, n- and i-propyl, n-, i- and t-butyl; $C_7$–$C_{18}$aralkyl, for example benzyl, methylbenzyl, dimethylbenzyl, methoxybenzyl, dimethoxybenzyl, bromobenzyl; diphenylmethyl, di(methylphenyl)methyl, di(dimethylphenyl)methyl, di(methoxyphenyl)methyl, di(dimethoxyphenyl)methyl, tritryl, tri(methylphenyl)methyl, tri(dimethylphenyl)methyl, methoxyphenyl(diphenyl)methyl, di(methoxyphenyl)phenylmethyl, tri(methoxyphenyl)methyl, tri(dimethosphenyl)methyl; triphenylsilyl, alkyldiphenylsilyl, dialkylphenylsilyl and trialkylsilyl having 1 to 20, preferably 1 to 12 and particularly preferably 1 to 8, C atoms in the alkyl groups, for example trimethylsilyl, triethylsilyl, tri-n-propylsilyl, i-propyldimethylsilyl, t-butyldimethylsilyl, t-butyl-diphenylsilyl, n-octyldimethylsilyl, (1,1,2,2-tetramethylethyl)dimethylsilyl; —($C_1$–$C_8$alkyl$)_2$Si—O—Si($C_1$–$C_8$alkyl$)_2$—, in which alkyl, for example, is methyl, ethyl, n- or i-propyl, n-, i- or t-butyl; $C_2$–$C_{12}$acyl, particularly $C_2$–$C_8$acyl, for example acetyl, propanoyl, butanoyl, pentanoyl, hexanoyl, benzoyl, methylbenzoyl, methoxybenzoyl, chlorobenzoyl and bromobenzoyl; $R_4$—$SO_2$—, in which $R_4$ is $C_1$–$C_{12}$alkyl, particularly $C_1$–$C_6$alkyl, $C_5$- or $C_6$cycloalkyl, phenyl, benzyl, $C_1$–$C_{12}$alkylphenyl and particularly $C_1$–$C_4$alkylphenyl, or $C_1$–$C_{12}$alkylbenzyl and particularly $C_1$–$C_4$alkylbenzyl, or halophenyl or halobenzyl, for example methyl—, ethyl—, propyl—, butyl—, phenyl—, benzyl—p-bromo—, p-methoxy- or p-methylphenylsulfonyl; unsubstituted or F—, Cl—, Br—, $C_1$–$C_4$alkoxy—, tri ($C_1$–$C_4$alkyl)silyl— or $C_1$–$C_4$alkylsulfonyl-substituted $C_1$–$C_{12}$alkoxycarbonyl, preferably $C_1$–$C_8$alkoxycarbonyl, for example methoxy—, ethoxy—, n- or i-propoxy- or n-, i- or t-butoxycarbonyl, 2-trimethylsilylethoxycarbonyl, 2-methylsufonylethoxycarbonyl, or phenoxycarbonyl or benzyloxycarbonyl which is unsubstituted or substituted as for alkoxycarbonyl, for example methyl— or methoxy— or chlorophenoxycarbonyl or —benzyloxy-carbonyl, and also 9-fluorenylmethyloxycarbonyl.

If the protecting group is alkyl, it can be substituted by F, Cl, Br, $C_1$–$c_4$alkoxy, phenoxy, chlorophenoxy, methoxyphenoxy, benzyloxy, methoxybenzyloxy or chlorophenoxy.

In a preferred embodiment, the protective groups are, independently or one another, linear or branched $C_1$–$C_4$alkyl, $C_7$–$C_{18}$aralkyl, trialkylsilyl having 1 to 12 C atoms in the alkyl groups, —($C_1$–$C_4$alkyl)$_2$Si—O—Si($C_1$–$C_4$alkyl)$_2$, $C_2$–$C_8$acyl, $R_4$—$SO_2$—, in which $R_4$ is $C_1$–$C_6$alkyl, phenyl, benzyl, $C_1$–$C_4$alkylphenyl, $C_1$–$C_4$alkyl benzyl, halophenyl or halobenzyl, or $C_1$–$C_8$alkoxycarbonyl, phenoxycarbonyl or benzyloxycarbonyl or 9-fluorenylmethoxycarbonyl.

In a particularly preferred embodiment, the protective groups are methyl, ethyl, n- or i-propyl, n-, i- or t-butyl; benzyl; methylbenzyl, dimethylbenzyl, methoxybenzyl, dimethoxybenzyl, bromobenzyl; diphenylmethyl, di(methylphenyl)methyl, di(dimethylphenyl)-methyl, di(methoxyphenyl)methyl, di(methoxyphenyl)(phenyl)methyl, trityl, tri(methylphenyl)methyl, tri(dimethylphenyl)methyl, tri(methoxyphenyl)methyl, tri(dimethoxyphenyl)methyl; trimethylsilyl, triethylsilyl, tri-n-propylsilyl, i-propyldimethylsilyl, t-butyl-dimethylsilyl, t-butyldiphenylsilyl, n-octyldimethylsilyl, (1,1,2,2-tetramethylethyl)-dimethylsilyl, —($CH_3$)$_2$Si—O—Si($CH_3$)$_2$—, —(i—$C_3H_7$)$_2$Si—O—Si(i—$C_3H_7$)$_2$—; acetyl, propanoyl, butanoyl, pentanoyl, hexanoyl, benzoyl, methylbenzoyl, methoxybenzoyl, chlorobenzoyl and bromobenzoyl; methyl-, ethyl-, propyl-, butyl-, phenyl-, benzyl-, p-bromo-, p-methoxy- and p-methylphenylsulfonyl; methox-, ethoxy-, n- or i-propoxy- or n-, i- or t-butoxycarbonyl, or phenoxycarbonyl, benzyloxycarbonyl, methyl- or methox- or chlorophenoxycarbonyl or —benzyloxycarbonyl or 9-fluorenylmethoxycarbonyl.

Preferred protective groups are $C_1$–$C_8$acyl groups, for example acetyl, propionyl, butyroyl and benzoyl. $R_{11}$ is preferably H or methyl.

The primary amino preferably contains 1 to 12 and particularly preferably 1 to 6 C atoms, and the secondary amino preferably 2 to 12 and particularly preferably 2 to 6 C atoms.

Some examples of alkyl, alkoxy, alkylthio, hydroxyalkyl and aminoalkyl, which preferably contain 1 to 6 C atoms, are methyl, ethyl and the isomers of propyl, butyl, pentyl, hexyl, heptyl, octyl, nonyl, decyl, undecyl and dodecyl, and also corresponding alkoxy, alkylthio, hydroxyalkyl and aminoalkyl radicals. The alkyl, alkoxy, alkylthio, hydroxyalkyl and aminoalkyl radicals preferably contain 1 to 4 C atoms. Preferred alkyl, alkoxy, alkylthio, hydroxyalkyl and aminoalkyl radicals are methyl, ethyl, n- and i-propyl, n-, i- and t-butyl, methoxy, ethoxy, methylthio and ethylthio, aminomethyl, aminoethyl, hydroxymethyl and hydroxyethyl.

The primary amino and secondary amino can, for example, be radicals of the formula $R_8R_9N$, in which $R_8$ is H or independently has the meaning of $R_9$, and $R_9$ is $C_1$–$C_{20}$alkyl, —aminoalkyl or —hydroxyalkyl, preferably $C_1$–$C_{12}$alkyl, —hydroxylakyl and particularly preferably $C_1$–$C_6$alkyl, —aminoalkyl or —hydroxylakyl; carboxyalkyl or carbalkoxyalkyl, where the carbalkoxy group contains 2 to 8 C atoms and the alkyl group contains 1 to 6, preferably 1 to 4, C atoms; $C_2$–$C_{20}$alkenyl, preferably $C_2$–$C_{12}$alkenyl and particularly preferably $C_2$–$C_6$alkenyl; phenyl, mono- or di($C_1$–$C_4$alkyl- or —alkoxy)phenyl, benzyl, mono- or di($C_1$–$C_4$alkyl— or —alkoxy)benzyl; or 1,2-, 1,3- or 1,4-imidazolyl-$C_1$–$C_6$alkyl, or $R_8$ and $R_9$ together are tetra- or pentamethylene, 3-oxa-1,5-pentylene, —$CH_2$—$NR_{10}$—$CH_2CH_2$— or —$CH_2CH_2$—$NR_{10}$—$CH_2CH_2$—, in which $R_{10}$ is H or $C_1$–$C_4$alkyl. The amino group in the aminoalkyl can be substituted by one or two $C_1$–$C_4$alkyl or —hydroxyalkyl groups. The hydroxyl group in hydroxyalkyl can be etherified with $C_1$–$C_4$alkyl.

Examples of alkyl have been given previously. Examples of aminoalkyl are aminomethyl, aminoethyl, 1-aminoprop-2-yl or -3-yl, 1-aminobut-2-yl or -3-yl or -4-yl, N-methyl- or N,N-dimethyl- or N-ethyl- or N,N-diethyl- or N-2-hydroxyethyl- or N,N-di-2-hydroxyethylaminomethyl or —aminoethyl or —aminopropyl or —aminobutyl. Examples of hydroxyalkyl are hydroxymethyl, 1-hydroxyethy-2-yl, 1-hydroxyprop-2- or -3yl, 1-hydoxybut-2-yl, -3-yl or —4—yl. Examples of carboxyalkyl are carboxymethyl, carboxyethyl, carboxypropyl and carboxybutyl, and examples of carbalkoxyalkyl are these carboxyalkyl groups esterified with methyl or ethyl. Examples of alkenyl are allyl, but-1-en-3-yl or -4-yl, pent-3- or 4-en-1-yl or -2-yl, hex-3- or -4- or -5-en-1-yl or -2-yl. Examples of alkyl- and alkoxyphenyl or benzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl, diethoxybenzyl. Examples of imidazolylalkyl, in which the alkyl group preferably contains 2 to 4 C atoms, are 1,2-, 1,3- or 1,4-imidazolylethyl or -n-propyl or -n-butyl. $R_{10}$ is preferably H, methyl or ethyl.

Preferred examples of primary amino and secondary amino are methyl-, ethyl-, dimethyl-, diethyl-, allyl-, mono- or di(1-hydroxyeth-2-yl)-, phenyl— and benzylamino, acetylamino, isobutyrylamino and benzoylamino.

In a preferred embodiment, $R_4$ is hydrogen. In another preferred embodiment, $R_7$ is hydrogen. In a further preferred embodiment, $R_5$ and $R_6$ independently of one another are H, F, Cl, Br, OH, SH, $NH_2$, NHOH, $NHNH_2$, methylamino, dimethylamino, benzoylamino, isobutyrylamino, methoxy, ethoxy and methylthio.

Besides purine, some examples of analogues of the purine series are adenine, N-methyl-adenine, N-benzoyladenine, 2-methylthioadenine, 2-aminoadenine, 6-hydroxypurine, 2-amino-6-chloropurine, 2-amino-6-methylthiopurine, guanine and N-isobutyrylguanine. Adenine, 2-aminoadenine and guanine, and also their base-protected derivatives, are particularly preferred.

If B in formula II is an analogous pyrimidine radical, it is preferably uracil, thymine or cytosine radicals of the of the formulae V, Va and Vb

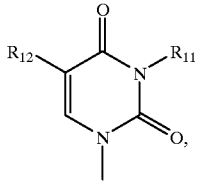

(V)

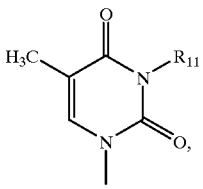

(Va)

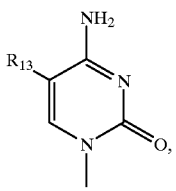

(Vb)

in which $R_{11}$ is H or $C_1$–$C_4$alkyl, and $R_{12}$ and $R_{13}$ independently of one another are H, F, Cl, Br, alkyl, propargyl or hydroxyalkyl or aminoalkyl or alkoxy or alkylthio having 1 to 12 C atoms, where the hydroxyl and amino groups are unsubstituted or substituted by a protective group, phenyl, benzyl, primary amino having 1 to 20 C atoms or secondary amino having 2 to 30 C atoms, and the hydrogen atoms of the $NH_2$ group in formula Vb are unsubstituted or substituted by $C_1$–$C_6$alkyl, benzoyl or benzyl, and the dihydro derivatives of the radicals of the formulae V, Va and Vb.

$R_{11}$ is preferably H. $R_{12}$ is preferably H, F, Cl, Br, $C_1$–$C_6$alkyl or hydroxyalkyl. $R_{13}$ is preferably H, F, Cl, Br, $C_1$–$C_6$alkyl or —alkoxy or —hydroxyalkyl.

Some examples of pyrimidine analogues are uracil, thymine, cytosine, 5-fluorouracil, 5-chlorouracil, 5-bromouracil, dihydrouracil and 5-methylcytosine.

In one embodiment the oligonucleotide of formula I comprises at least one structural unit of two consecutive nucleosides, the stuctural unit comprising the formula IIa or IIc wherein $R_1$ is H, $C_1$–$C_4$alkyl or $C_1$–$C_4$alkoxy;

$R_2$ is H; $C_1$–$C_4$alkyl; phenyl; phenyl substituted with OH, OR'", $O(CH_2CH_2O)_nR'"$, $C_6$–$C_{10}$aryl or $C_3$–$C_9$heteroaryl; an intercalator; amino-$C_1$–$C_4$alkyl; $C_1$–$C_4$alkylamino; ammonium-$C_1$–$C_4$alkyl; $C_1$–$C_4$alkylammonium; amino-$C_1$–$C_4$alkylaminosulfonyl; $C_1$–$C_4$alkylamino-$C_1$–$C_4$alkylaminosulfonyl or $(CH_3)_2NCH_2CH_2$;

$R_3$ is H or $C_1$–$C_4$alkyl;

R'" is $C_1$–$C_4$alkyl;

X is H, OH, O—$C_1$–$C_4$alkyl, —O—$(CH_2$—$CH_2$—$O)_m$H or —O—$CH_2$—$C(OR)H$—$CH_2$—OH;

Y is H, O—$C_1$–$C_4$alkyl, —O—$(CH_2$—$CH_2$—$O)_m$H or —O—$CH_2$—$C(OR)H$—$CH_2$—OH;

R is H or $C_1$–$C_{10}$alkyl;

m is an integer from 1 to 4;

n is an integer from 1 to 4 and

B is a purine or pyrimidine radical or an analogue thereof.

In a preferred embodiment the oligonucleotide of formula I comprises at least one structural unit of two consecutive nucleosides, the structural unit comprising the formula IIa or IIc wherein $R_1$ is H or $C_1$–$C_4$alkyl;

$R_2$ is H; $C_1$–$C_4$alkyl; phenyl or phenyl substituted with OH, OR'", $O(CH_2CH_2O)_nR'"$, $C_6$–$C_{10}$aryl or $C_3$–$C_9$heteroaryl;

$R_3$ is H or $C_1$–$C_4$alkyl;

R'" is $C_1$–$C_4$alkyl;

X is H, OH, O—$C_1$–$C_4$alkyl, —O—$(CH_2$—$CH_2$—$O)_m$H or —O—$CH_2$—$C(OR)H$—$CH_2$—OH;

Y is H, O—$C_1$–$C_{14}$alkyl, —O—$(CH_2$—$CH_2$—$O)_m$H or —O—$CH_2$—$C(OR)H$—$CH_2$—OH;

R is H or $C_1$–$C_{10}$alkyl;

m is an integer from 1 to 4;

n is an integer from 1 to 4 and

B is a puine or pyrimidine radical or an analogue thereof.

In a particularly preferred embodiment the oligonucleotide of formula I comprises at least one structural unit of two consecutive nucleosides, the structural unit comprising the formula IIa or IIc wherein $R_1$ is H or $C_1$–$C_4$alkyl;

$R_2$ is H; $C_1$–$C_4$alkyl or phenyl;

$R_3$ is H or $C_1$–$C_4$alkyl;

X is H, OH, O—$C_1$–$C_4$alkyl, —O—$(CH_2$—$CH_2$—$O)_m$H or —O—$CH_2$—$C(OR)H$—$CH_2$—OH;

Y is H, O—$C_1$–$C_4$alkyl, —O—$(CH_2$—$CH_2$—$O)_m$H or —O—$CH_2$—$C(OR)H$—$CH_2$—OH;

R is H or $C_1$–$C_{10}$alkyl;

m is an integer from 1 to 4;

n is an integer from 1 to 4 and

B is a puine or pyrimidine radical or an analogue thereof.

More preferred are oligonucleotides of formula I comprising at least one structural unit of two consecutive nucleosides, the structural unit comprising the formula IIa or IIc wherein $R_1$ is H or $C_1$–$C_4$alkyl;

$R_2$ is H; $C_1$–$C_4$alkyl or phenyl;

$R_3$ is H or $C_1$–$C_4$alkyl;

X is H, OH or O—$C_1$–$C_4$alkyl;

Y is H or O—$C_1$–$C_4$alkyl; and

B is a purine or pyrimidine radical or an analogue thereof.

Most preferred are oligonucleotides of formula I comprising at least one structural unit of two consecutive nucleosides, the structural unit comprising the formula IIa or IIc wherein $R_1$ is H;

$R_2$ is H or phenyl;

$R_3$ is H or methyl;

X is H or O—$CH_3$;

Y is H or O—$CH_3$; and

B is a pyrimidine radical or an analogue thereof.

Another object of the present invention is a nucleotide dimer of the formula IIIa, IIIb, IIIc or IIId

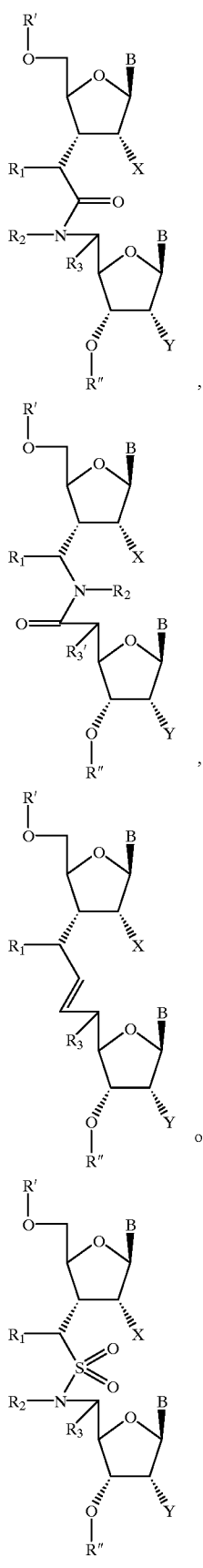

(IIIa)
(IIIb)
(IIIc)
(IIId)

wherein
$R_1$ is H, $C_1$–$C_4$alkyl or $C_1$–$C_4$alkoxy;
$R_2$ is H; $C_1$–$C_4$alkyl; phenyl; phenyl substituted with OH, OR''', O($CH_2CH_2O$)$_n$R''', $C_6$–$C_{10}$aryl or $C_3$–$C_9$heteroaryl; an intercalator; amino-$C_1$–$C_4$alkyl; $C_1$–$C_4$alkylamino; ammonium-$C_1$–$C_4$alkyl; $C_1$–$C_4$alkylammonium; amino-$C_1$–$C_4$alkylaminosulfonyl; $C_1$–$C_4$alkylamino-$C_1$–$C_4$alkylaminosulfonyl; or $(CH_3)_2NCH_2CH_2$;
$R_3$ is H or $C_1$–$C_4$alkyl;
$R_3'$ is H; OH; $C_1$–$C_4$alkyl; O—$C_1$–$C_4$alkyl; O($CH_2CH_2O$)$_n$R''';
R' and R'' are H or an OH-protecting group of R'' is a radical forming a phosphorus-containing nucleotide bridge group;
R''' is $C_1$–$C_4$alkyl;
X is H, $OR_x$, O—$C_1$–$C_4$alkyl, —O—($CH_2$—$CH_2$—O)$_m$H or —O—$CH_2$—C(OR)H—$CH_2$—$OR_x$;
Y is H, O—$C_1$–$C_4$alkyl, —O—($CH_2$—$CH_2$—O)$_m$H or —O—$CH_2$—C(OR)H—$CH_2$—OH;
R is H or $C_1$–$C_{10}$alkyl;
$R_x$ is H or an OH-protecting group;
m is an integer from 1 to 4;
n is an integer from 1 to 4 and
B is a purine or pyrimidine radical or an analogue thereof with the proviso that either X or Y is H or that X and Y are not identical.

Suitable protective groups have been mentioned above.
A phosphorus-containing nucleotide bridge group is a radical of the formula $$Y_a-\underset{OR_a}{\overset{|}{P}}=X_a$$

in which $Y_a$ is hydrogen, $C_1$–$C_{12}$alkyl, $C_6$–$C_{12}$aryl, $C_7$–$C_{20}$aralkyl, $C_7$–$C_{20}$alkaryl, —$OR_b$, —$SR_b$, —$NH_2$, primary amino, secondary amino, $O^{\ominus}M^{\oplus}$ or $S^{\ominus}M^{\oplus}$; $X_a$ is oxygen or sulfur; $R_a$ is hydrogen, $M^{\oplus}$, $C_1$–$C_{12}$alkyl, $C_2$–$C_{12}$alkenyl or $C_6$–$C_{12}$aryl, or the group $R_aO$ is N—heteroaryl—N—yl having 5 ring members and 1 to 3 N atoms; $R_b$ is hydrogen, $C_1$–$C_{12}$alkyl or $C_6$–$C_{12}$aryl; and $M^{\oplus}$ is $Na^{\oplus}$, $K^{\oplus}$, $Li^{\oplus}$, $NH_4^{\oplus}$ or primary, secondary, tertiary or quaternary ammonium; where alkyl, aryl, aralkyl and alkaryl in $Y_a$, $R_a$ and $R_b$ are unsubstituted or substituted by alkoxy, alkylthio, halogen, —CN, —$NO_2$, phenyl, nitrophenyl or halophenyl.

A preferred bridge group is the group —P(O)O$^{\ominus}$—, which occurs in natural oligonucleotides. Examples of further bridge groups are —P(O)S$^{\ominus}$—, —P(S)S$^{\ominus}$—, —P(O)$R_{16}$—, P(O)N$R_{17}R_{18}$, or —$CH_2$—, in which $R_{16}$ is H or $C_1$–$C_6$alkyl and $R_{17}$ and $R_{18}$ independently of one another have the meaning of $R_{16}$.

In one embodiment of the present invention the nucleotide dimers are of the formula IIIa or IIIc
wherein
$R_1$ is H, $C_1$–$C_4$alkyl or $C_1$–$C_4$alkoxy;
$R_2$ is H; $C_1$–$C_4$alkyl; phenyl; phenyl substituted with OH, OR''', O($CH_2CH_2O$)$_n$R''', $C_6$–$C_{10}$aryl or $C_3$–$C_9$heteroaryl; an intercalator; amino—$C_1$–$C_4$alkyl; $C_1$–$C_4$alkylamino; ammonium—$C_1$–$C_4$alkyl; $C_1$–$C_4$alkylammonium; amino—

$C_1$–$C_4$alkylaminosulfonyl; $C_1$–$C_4$alkylamino—$C_1$–$C_4$alkylaminosulfonyl or $(CH_3)_2NCH_2CH_2$;

$R_3$ is H or $C_1$–$C_4$alkyl;

R''' is $C_1$–$C_4$alkyl;

X is H, $OR_x$, O—$C_1$–$C_4$alkyl, —O—$(CH_2$—$CH_2$—O$)_m$H or —O—$CH_2$—C(OR)H—$CH_2$—$OR_x$;

Y is H, O—$C_1$–$C_4$alkyl, —O—$(CH_2CH_2$—O$)_m$H or —O—$CH_2$—C(OR)H—$CH_2$—OH;

R is H or $C_1$–$C_{10}$alkyl;

$R_x$ is H or an OH-protecting group;

m is an integer from 1 to 4;

n is an integer from 1 to 4 and

B is a purine or pyrimidine radical or an analogue thereof

In a preferred embodiment the nucleotide dimers are of the formula IIIa or IIIc wherein $R_1$ is H or $C_1$–$C_4$alkyl;

$R_2$ is H; $C_1$–$C_4$alkyl; phenyl or phenyl substituted with OH, OR''', $O(CH_2CH_2O)_nR'''$, $C_6$–$C_{10}$aryl or $C_3$–$C_9$heteroaryl;

$R_3$ is H or $C_1$–$C_4$alkyl;

R''' is $C_1$–$C_4$alkyl;

X is H, $OR_x$, O—$C_1$–$C_4$alkyl, —O—$(CH_2$—$CH_2O)_m$H or —O—$CH_2$—C(OR)H—$CH_2$—$OR_x$;

Y is H, O—$C_1$–$C_4$alkyl, —O—$(CH_2$—$CH_2$—O$)_m$H or —O—$CH_2$—C(OR)H—$CH_2$—OH;

R is H or $C_1$–$C_{10}$alkyl;

$R_x$ is H or an OH-protecting group;

m is an integer from 1 to 4;

n is an integer from 1 to 4 and

B is a purine or pyrimidine radical or an analogue thereof.

In a particularly preferred embodiment the nucleotide dimers are of the formula IIIa or IIIc wherein $R_1$ is H or $C_1$–$C_4$alkyl;

$R_2$ is H; $C_1$–$C_4$alkyl or phenyl;

$R_3$ is H or $C_1$–$C_4$alkyl;

X is H, $OR_x$, O—$C_1$–$C_4$alkyl, —O—$(CH_2$—$CH_2$—O$)_m$H or —O—$CH_2$—C(OR)H—$CH_2$—$OR_x$;

Y is H, O—$C_1$–$C_4$alkyl, —O—$(CH_2$—$CH_2$—O$)_m$ H or —O—$CH_2$—C(OR)H—$CH_2$—OH;

R is H or $C_1$–$C_{10}$alkyl;

$R_x$ is H or an OH-protecting group;

m is an integer from 1 to 4;

n is an integer from 1 to 4 and

B is a purine or pyrimidine radical or an analogue thereof.

More preferred are nucleotide dimers of the formula IIIa or IIIc wherein $R_1$ is H or $C_1$–$C_4$alkyl;

$R_2$ is H; $C_1$–$C_4$alkyl or phenyl;

$R_3$ is H or $C_1$–$C_4$alkyl;

X is H, $OR_x$ or O—$C_1$–$C_4$alkyl;

Y is H or O—$C_1$–$C_4$alkyl;

$R_x$ is H or an OH-protecting group; and

B is a purine or pyrimidine radical or an analogue thereof.

Most preferred are nucleotide dimers of the formula IIIa or IIIc wherein $R_1$ is H;

$R_2$ is H or phenyl;

$R_3$ is H or methyl;

X is H or O—$CH_3$;

Y is H or O—$CH_3$; and

B is a pyrimidine radical or an analogue thereof.

The invention further relates to a process for the preparation of compounds of the formula IIIa, IIIb, IIIc or IIId, which is characterised in that (a) a compound of the formula VI (VI)

[Structure: R'—O—[furanose ring with B]—X, with $R_1$ and COOH substituents]

wherein $R_1$ is H, $C_1$–$C_4$alkyl or $C_1$–$C_4$alkoxy;

R' is H or an OH-protecting group

X is H, OH, O—$C_1$–$C_4$alkyl, —O—$(CH_2$—$CH_2$—O$)_m$H— or —O—$CH_2$—C(OR)H—$CH_2$—OH;

R is H or $C_1$–$C_{10}$alkyl; and

B is a purine or pyrimidine radical or an analogue thereof;

is reacted with a compound of the formula VII (VII)

[Structure: $R_2$—NH—[furanose ring with B]—Y, with $R_3$ and OR'' substituents]

wherein $R_2$ is H; $C_1$–$C_4$alkyl; phenyl; phenyl substituted with OH, OR''', $O(CH_2CH_2O)_nR'''$, $C_6$–$C_{10}$aryl or $C_3$–$C_9$heteroaryl; an intercalator; amino—$C_1$–$C_4$alkyl; $C_1$–$C_4$alkylamino; ammonium—$C_1$–$C_4$alkyl; $C_1$–$C_4$alkylammonium; amino—$C_1$–$C_4$alkylaminosulfonyl; $C_1$–$C_4$alkylamino—$C_1$–$C_4$alkylaminosulfonyl; or $(CH_3)_2NCH_2CH_2$;

$R_3$ is H or $C_1$–$C_4$alkyl;

R'' is H or an OH-protecting group or a radical forming a phosphorus-containing nucleotide bridge group;

R''' is $C_1$–$C_4$alkyl;

Y is H, O—$C_1$—$C_4$alkyl, —O—$(CH_2$—$CH_2$—O$)_m$H or —O—$CH_2$—C(OR)H—$CH_2$—OH; and B is a purine or pyrimidine radical or an analogue thereof; or (b) a compound of the formula VIII

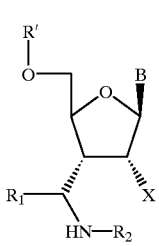
(VIII)

wherein $R_1$, $R_2$, R', X and B are as defined above, is reacted with a compound of the formula IX

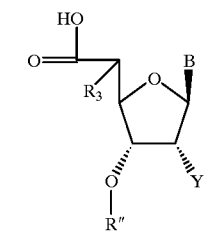
(IX)

wherein $R_3$, R", Y and B are as defined above; or (c) a compound of the formula X

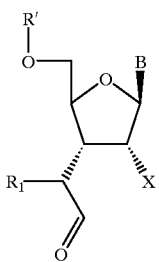
(X)

wherein $R_1$, R', X and B are as defined above, is reacted with a compound of the formula XI

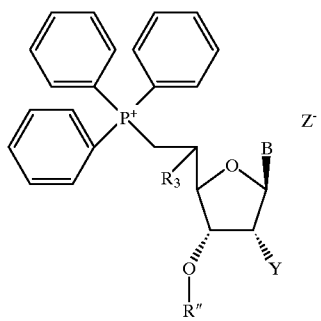
(XI)

wherein $R_3$, R", Y and B are as defined above, and Z is halogen, for example, F, Cl, Na; or (d) a compound of the formula XII

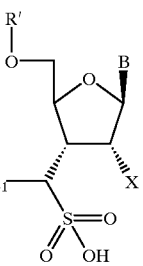
(XII)

wherein
$R_1$, R', X and B are as defined above, is reacted with a compound of the formula XIII

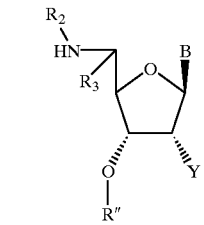
(XIII)

wherein $R_2$, R", Y and B are as defined above.

Compounds of the formulae VI, VII, VIII, IX, X, XI, XII and XIII are known or can be prepared according to for example De Mesmaeker, A., Waldner, A., Lebreton, J., Hoffmann, P., Fritsch, V., Wolf, R. M., Freier, S. M. Angew. Chem. Int. Ed. Engl. 33:226–229 (1994) or Pudlo, J. S., Townsend, L. B., Tetrahedron Lett. 31:3101 (1990).

The temperature in the synthesis reaction can be from −80° to 150° C., preferably 0° to 100° C.

In general, solvents are used which are protic and/or aprotic, and particularly preferably dipolar. Examples of solvents which can be employed on their own or as a mixture of at least two solvents are ethers (dibutyl ether, tetrahydrofuran, dioxane, diethylene glycol dimethyl ether, ethylene glycol dimethyl or diethyl ehter, diethylene glycol diethyl ether, triethylene glycol dimethyl ether), halogenated hydrocarbons (methylene chloride, chloroform, 1,2-dichlooethane, 1,1,1-trichloroethane, 1,1,2,2-tetrachloroethane), carboxylic acid esters and lactones (ethyl acetate, methyl propionate, ethyl benzoate, 2-methoxyethyl acetate, methoxymethyl acetate, γ-butyrolactone, δ-valerolactone, pivalolactone), carboxamides and lactams (N,N-dimethylformamide, N,N-diethylformamide, N,N,-dimethylacetamide, tetramethylurea, hexamethylphosphoramide, γ-butyrolactam, ε-caprolactam, N-methylpyrrolidone, N-acetylpyrrolidone, N-methylcaprolactam), sulfoxides (dimethyl sulfoxide), sulfones (dimethyl sulfone, diethyl sulfone, trimethylene sulfone, tetramethylene sulfone), tertiary amines (triethylamine, N-methylpiperidine, N-methylmorpholine), aromatic hydrocarbons, for example benzene or substituted benzenes (chlorobenzene, o-dichlorobenzene, 1,2,4-trichlorobenzene, nitrobenzene, toluene, xylene) and nitriles (acetonitrile, propionitrile, benzonitrile, phenylacetonitrile), and also aliphatic or cycloaliphatic hydrocarbons (pentane, petroleum ether, hexane, cyclohexane and methylcyclohexane).

An object of the present invention is the use of a dimer of the formulae IIIa, IIIb, IIIc or IIId for the preparation of oligonucleotides which comprise one or more identical or different dimer units of the formulae IIIa, IIIb, IIIc and/or IIId.

The oligonucleotides according to the invention can be prepared in a manner known per se by various processes, preferably on a solid support. For details see for example Gait, M. J., Oligonucleotide Synthesis: A Practical Approach, IRL Press, Oxford (1984).

The oligonucleotides of the formula I according to the invention have antiviral and antiproliferative properties and can accordingly be used as medicaments. The oligonucleotides according to the invention have a surprisingly high stability to degradation by nucleases. A very good pairing with complementary nucleic acid strands, particularly of the RNA type A, is also observed. The oligonucleotides according to the invention are therefore particularly suitable for antisens technology, i.e. for inhibition of the expression of undesired protein products due to the binding to suitable complementary nucleotide sequences in nucleic acids (see EP 266,099 WO 87/07300 and WO 89/08146). They can be employed for the treatment of infections and diseases, for example by blocking the expression of bioactive proteins at the nucleic acid stage (for example oncogenes). The oligonucleotides according to the invention are also suitable as diagnostics and can be used as gene probes for the detection of viral infections or of genetically related diseases by selective interaction at the single- or double-stranded nucleic acid stage. In particular—due to the increased stability to nucleases—diagonistic use is not only possible in vitro but also in vivo (for example tissue samples, blood plasma and blood serum). Use possibilities of this type are described, for example, in WO 91/06556.

The invention relates to the use of the oligonucleotides according to the invention as diagnostics for the detection of viral infections or of genetically related diseases.

The invention also relates to the the oligonucleotides of the formula I according to the invention for use in a therapeutic process for the treatment of disease in mammals including humans by means of inactivation of nucleotide sequences in the body. The dose when administered to mammals of about 60 kg body weight can be, for example, 0.01 to 1000 mg per day. Administration is preferably effected parenterally, for example intravenously or intraperitoneally, in the form of pharmaceutical preparations.

The invention further relates to a pharmaceutical preparation comprising an effective amount of an oligonucleotide of the formula I on its own or together with other active ingredients, a pharmaceutical carrier in a customary amount and, if appropriate, excipients.

The pharmacologically active oligonucleotides according to the invention can be used in the form of parenterally administrable preparations or of infusion solutions. Solutions of this type are preferably isotonic aqueous solutions or suspensions, it being possible to prepare these before use, for example in the case of lyophilised preparations which contain the active substance on its own or together with a carrier, for example mannitol. The pharmaceutical preparations can be sterilised and/or contain excipients, for example preservatives, stabilisers, wetting and/or emulsifying agents, solubilisers, salts for regulating the osmotic pressure and/or buffers. The pharmaceutical preparations, which if desired can contain further pharmacologically active substances such as, for example, antibiotics, are prepared in a manner known per se, for example by means of conventional dissolving or lyophilising processes, and contain about 0.1% to 90%, in particular from about 0.5% to about 30%, for example 1% to 5% of active substance(s).

The examples below illustrate the invention.

The following abbreviations are used in the examples:
BN: benzyl DMT: dimethoxy trityl HV: high vacuum Me: methyl nBu$_4$NF: tetrabutyl ammonium fluoride O—Ac: acetate Ph: phenyl pMeOBOM: p-methoxybenzyloxybenzyl RT: room temperature T: thymine tBuPh$_2$Si: tert.butyldiphenylsilyl Ts: tosyl TTTr: tris tert.butyl trityl

A. PREPARATION OF DIMERS

Example A1: Preparation of compound no. 12

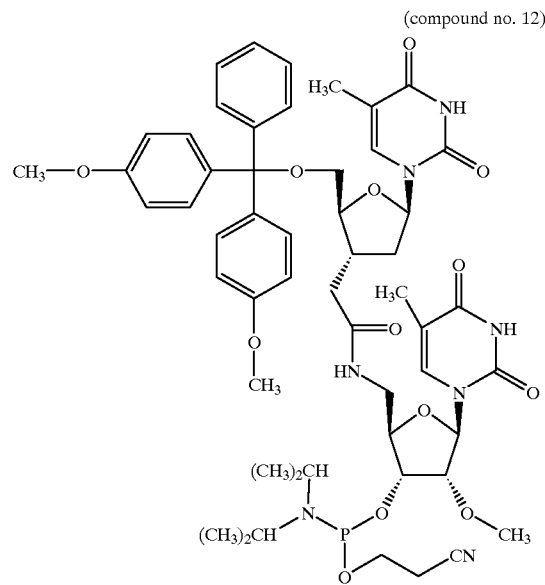

(compound no. 12)

Steps (a) to (e) are performed under a dry atmosphere of argon.

(a) 5.12 g of compound no. 0

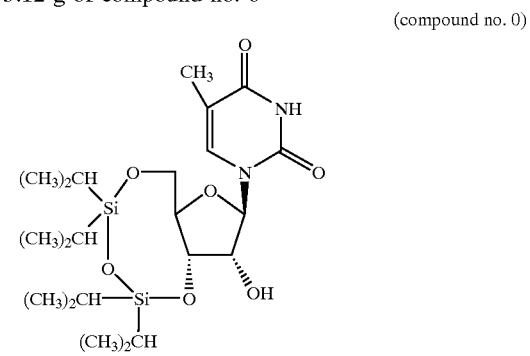

(compound no. 0)

are dissolved in 70 ml of dry acetonitrile. To this solution 1.599 g benzyloxymethylchloride and 1.556 g 1,5-diazabicyclo-[5.4.0.]-undec-5-en are added at room temperature. The mixture is stirred at room temperature for 40 h, then diluted with 70 ml of CH$_2$Cl$_2$, washed with 70 ml of aqueous NaH$_2$PO$_4$ and twice with a saturated solution of NaCl. The organic phase is dried over Na$_2$SO$_4$. After evaporation of the solvent, the residue is chromatographed on silica gel (hexane/acetic acid ester 6:1) to obtain compound no 1.

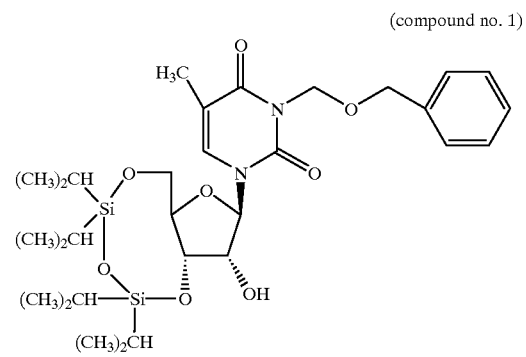

(compound no. 1)

$^1$H—NMR (CHCl$_3$, 500 MHz, J(Hz)): 1.91 (3H$_7$, d, J$_{6-7}$=1.0); 4.01 (H$_{5'}$, dd, J$_{5'-5''}$=13.0, J$_{5'-4'}$=3.0); 4.06 (H$_{4'}$, ddd); 4.14 (H$_{2'}$, ddd), 4.19 (H$_{5''}$, dd, J$_{5''-4'}$=2.5); 4.40 (H$_{3'}$, dd, J3'—2'=5.1; J$_{3'-4'}$=8.6); 4.72 (OCH$_2$Ph, s); 5.48 and 5.51 (NCH$_2$O, AB, J=9.9); 5.72 (H$_{2'}$, d, J$_{1'-2'}$=1.0). Ms (FD)(m/e): 620 (M$^+$).

(b) 12.87 g of compound no. 1 are dissolved in 100 ml CH$_3$I. To this mixture 40.32 g of Ag$_2$O are added at room temperature. The suspension is stirred at 45° for 2 days in the dark. The CH$_3$I is distilled off, the residue is stirred with CH$_2$Cl$_2$ and filtered. The Ag$_2$O is carefully washed with CH$_2$Cl$_2$ and the solvent is evaporated to obtain compound no. 2.

(compound no. 2)

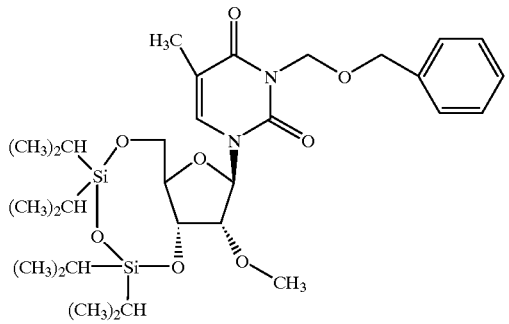

$^1$H—NMR (CHCl$_3$, 500 MHz, J(Hz)): 1.92(3H$_7$, d, J$_{6-7}$=1.0); 3.68 (OMe, s); 3.97 (H$_{5'}$, dd, J$_{5'-5''}$=13.2, J$_{5'-4'}$=2.5); 4.11 (H$_{4'}$, dd); 4.20 (H$_{3'}$, dd), 4.24 (H$_{5''}$, d); 5.72 (H$_{1'}$, s). MS (FD)/(m/e): 635 (M$^+$).

(c) To a solution of 0.771 g compound no. 2 in 20 ml dry tetrahydrofuran 0.182 g acetic acid and 0.698 g tetrabutylammonium fluoride are added. The mixture is stirred at room temperature for 20 h. 0.169 ml of triethylamine are added and the mixture is coevaporated with toluene (3×). The residue is chromatographed on silica gel (acetic acid ester/methanol 30:1) to obtain compound no 3.

(compound no. 3)

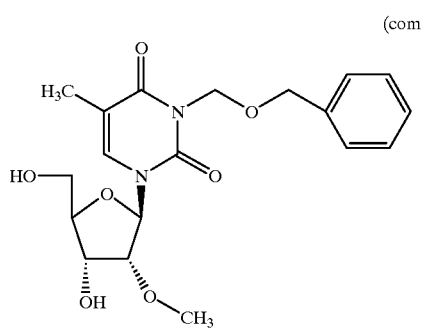

$^1$H—NMR (CHCl$_3$, 500 MHz, J(Hz)): 1.97(3H$_7$d, J$_{6-7}$=1.0); 3.58 (OMe, s); 3.87 (H$_{5'}$, ddd, J$_{5'-5''}$=10.2, J$_{5'-4'}$=2.5): 4.32 (H$_{3'}$, ddd); 5.73 (H$_{1'}$, d). MS (FD)(m/e):392 (M$^+$).

(d) A mixture of 0.772 g of triphenyl phosphine and 0.54 g compound no. 3 are dissolved in toluene/tetrahydrofuran (5:1) at room temperature. 0.338 g of Zn(N$_3$)$_2$·2 pyridine are added followed by the slow addition of 0.556 g of diethylazodicarboxylate. After 4 h at room temperature the mixture is filtered, the solvent is evaporated. The residue is chromatographed on silica gel (hexane/acetic acid ester 1:1) to obtain compound no. 4.

(compound no. 4)

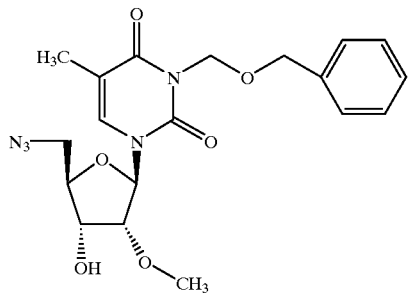

$^1$H—NMR (CHCl$_3$, 500 MHz, J(Hz)): 1.97 (3H$_7$, d, J$_{5-7}$=1.0); 3.63 (OMe, s); 3.69 (H$_{5'}$, dd); 4.15 (H$_{3'}$, m); 5.90 (H$_{1'}$,d). MS(FD)(m/e): 417 (M$^+$). IR: 2100 cm$^{-1}$(N$_3$).

(e) 0.472 g of compound no. 4 are dissolved in 6 ml of dry dimethyl formamide. To this solution 0.777 g tert.butyldiphenylchlorosilane, 0.138 g dimethylamino pyridine and 0.228 g triethylamine are added. The mixture is heated to 50° C. and stirred for 18 h at this temperature. 20 ml of a saturated solution of NaH$_2$PO$_4$ is added to the mixture and the solvents are removed under high vacuum. The residue is dissolved in CH$_2$Cl$_2$ and NaH$_2$PO$_4$. The organic phase is washed with a saturated solution of NaCl and dried over Na$_2$SO$_4$. After evaporation of the solvent chromatography of the residue on silica gel affords compound no. 5.

(compound no. 5)

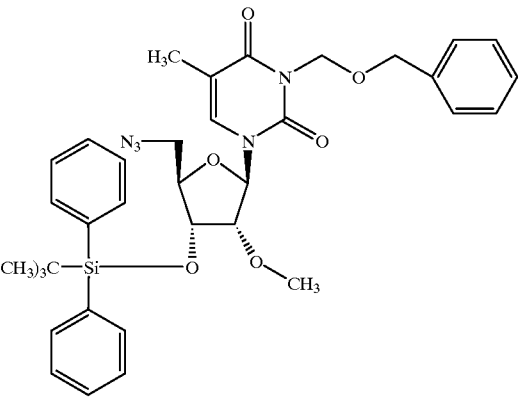

$^1$H—NMR (CHCl$_3$, 500 MHz, J(Hz)): 1.08 (t—Bu, 9H, s); 1.84(3H$_7$, d, J$_{6-7}$=1.0); 3.37 (OMe, s); 5.90 (H$_{1'}$, d, J$_{1'-2'}$=2.0).

(f) 0.62 g of compound no. 5 dissolved in 5 ml of methanol are added to a suspension of 0.427 g SnCl$_2$·2H$_2$O in 15 ml of methanol. The mixture is stirred for 20 h at room temperature. The pH is brought to 8 with aqueous NaHCO$_3$. The methanol is evaporated and the aqueous phase is extracted 3× with CH$_2$Cl$_2$. The organic phase is dried and the solvent is removed. Compound no. 6 is obtained by chromatography.

(compound no. 6)

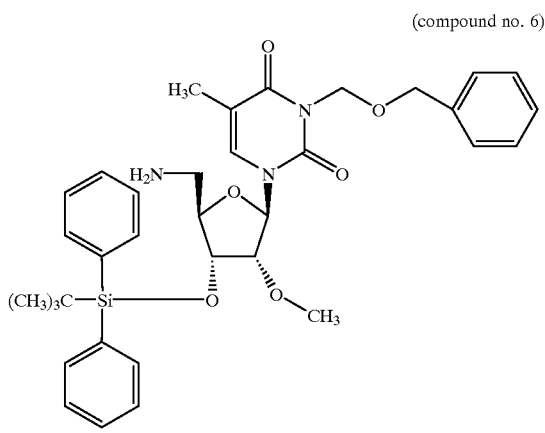

$^1$N—NMR (CHCl$_3$, 500 MHz, J(Hz)); 1.11 (t—Bu, 9H, s); 1.80 (3H$_7$, d, J$_{6-7}$=1.0); 2.70(H$_{5'}$, dd, J$_{5'-5''}$=14.0, J$_{5'-4'}$=4.1); 2.99 (H$_{5''}$, dd, J$_{5''-'}$=3.0); 3.99 (H$_{3'}$, dd, J$_{3'-4'}$=8.0, J$_{3'-2'}$=5.0); 5.89 (H$_{1'}$, d). MSCFD(m/e): 630 (M$^+$).

(g) 1.123 g of compound no. 7

(Compound no. 7)

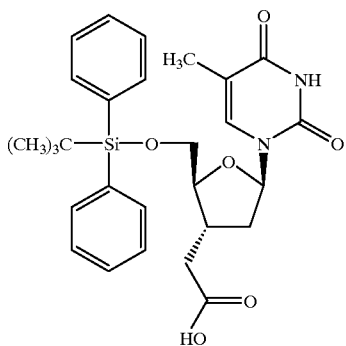

prepared according to De Mesmaker, A., Waldner, A., Lebreton, J., Hoffmann, P., Fritsch, V., Wolf, R. M., Freier, S. M., Angew. Chem. Int. Ed. Engl. 33:226–229 (1994) are dissolved in 30 ml dry acetonitrile. 0.239 g N-methylmorpholine, 0.758 g O-(1H-benzotriazole-1-yl)—N,N,N',N'-tetramethyluronium tetrafluoroborate and 0.145 g N-hydroxybenzotriazole are added. This mixture is stirred at room temperature for 30 minutes. Then 1.353 g of compound no. 6 and 0.326 g N-methylmorpholine are added. After 20 h a saturated solution of NaH$_2$PO$_4$ is added. The organic solvent is removed under vacuum. The aqueous phase is extracted with CH$_2$Cl$_2$, the organic phase is dried and evaporated. The residue is purified by chromatography on silica gel to obtain compound no. 8.

(Compound no. 8)

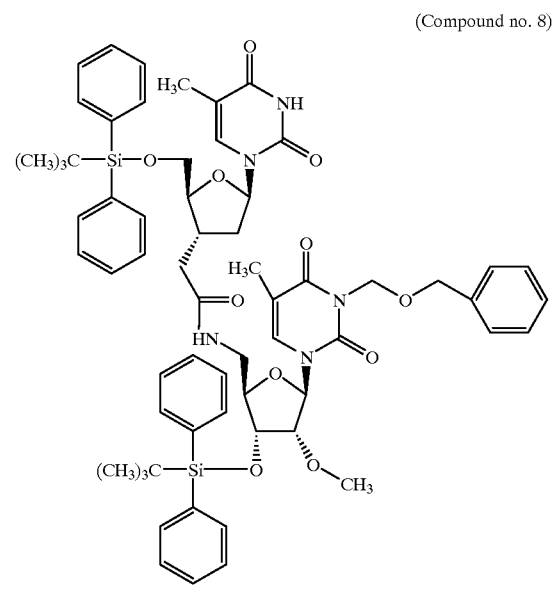

$^1$H—NMR (CHCl$_3$, 500 MHz, J(Hz)): 1.09 (t—Bu, 9H, s); 1.10(t—Bu, 9H, s); 1.62 (3 H$_7$, d, J$_{6-7}$=0.9); 1.89 (3 H$_7$, d, J$_{6-7}$=0.9); 3.14 (OME, s); 5.14(H$_{1'}$, d, J$_{1'-2'}$=3.8); 6.10 (H$_{1'}$, dd, J$_{1'-2'}$=5.1, J$_{1'-2''}$=6.1). MS (FD)(m/e): 1133 (M$^+$).

(h) 1.95 g of compound no. 8 are dissolved in 15 ml of tetrahydrofuran. To this solution 0.309 g acetic acid and 4.7 ml of a tetrabutylammonium fluoride solution (1 M in tetrahydrofuran) are added. The mixture is stirred at room temperature for 18 h. 0.263 ml triethylamine are added and the solvent is coevaporated 3× with toluene. Compound no. 9 is isolated by chromatography on silica gel.

(Compound no. 9)

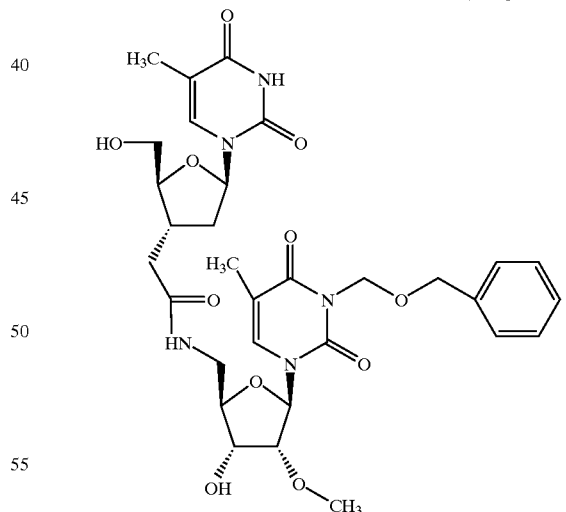

$^1$H—NMR (CHCl$_3$, 250 MHz, J(Hz)): 1.89 (3H$_7$, d,); 1.96 (3 H$_7$d); 3.53 (OMe, s); 5.40 (H$_{1'}$, d); 5.98 (H$_{1'}$, dd,).

(i) 1.08 g of compound no. 9 are dissolved in 20 ml methanol. 1.08 g of 5% Pd/C is added. The mixture is stirred under an atmosphere of hydrogen for 24 h at room temperature. The catalyst is filtered off, washed with methanol and CHCl$_3$ and the combined filtrates are evaporated. Chromatography of the residue on silica gel (acetic acid ester/methanol 9:1) affords compound no. 10.

(Compound no. 10)

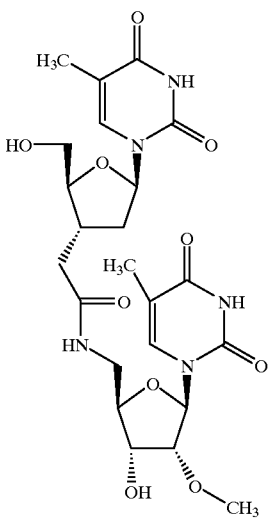

$^1$H—NMR (CD$_3$OD, 500 MHz,J(Hz)): 1.87 (3H$_7$, d, J$_{6-7}$=1.0); 1.90 (3 H$_7$, d, J$_{6-7}$=1.0); 3.48 (OMe, s); 5.78 (H$_{1'}$, d, J$_{1'-2'}$=4.0); 6.05 (H$_{1'}$, dd, J$_{1'-2'}$=3.1, J$_{1'-2''}$=6.9).

(j) 0.755 g of compound no. 10 are dissolved in 10 ml of dry pyridine. To this mixture 0.954 g of p-dimethoxytritylchloride are added in two portions. The mixture is stirred at room temperature for 48 h. The pyridine is coevaporated with toluene under vacuum. The residue is chromatographed on silica gel (acetic acid ester, methanol+ 1% triethylamine; 100:1 to 10:1) to obtain compound no. 11.

(Compound no. 11)

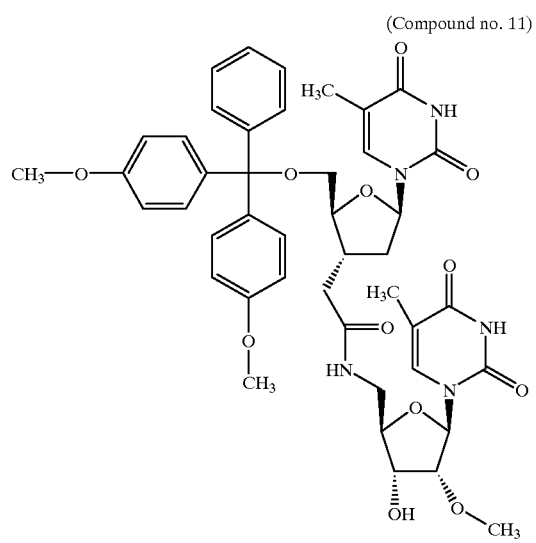

$^1$H—NMR (CHCl$_3$, 500 MHz,J(Hz)): 1.42(3H$_7$, d); 1.91 (3H$_7$, d); 3.51 (OMe, s); 5.24 (H$_{1'}$, d, J$_{1'-2'}$=3.0); 6.24 (H$_{1'}$, dd, J$_{1'-2'}$, J$_{1'-2''}$=6.0). M.S. (C.I.)m/e: 839 M$^+$.

(k) 0.361 g of compound no. 11 are dissolved in 12 ml CH$_2$Cl$_2$. 0.143 g 2-cyanoethyl-N,N,N',N'-tetraisopropyl-phosphoramidite and 0.088 g N,N-diisopropylammonium tetrazolide are added. The mixture is stirred at room temperature for 20 h. The reaction mixture is diluted with CH$_2$Cl$_2$ and with NaHCO$_3$. The organic phase is washed with a saturated solution of NaCl and dried over Na$_2$SO$_4$. After removal of the solvent the residue is chromatographed on silica gel (acetic acid ester, methanol+1% N-methylmorpholine; 50:1 to 9:1) to obtain compound no. 12.

$^1$H—NMR (CHCl$_3$, 500 MHz,J(Hz)): 1.47 (3 H$_7$, m); 1.91 (3 H$_7$, m); 3.40 (OMe, s); 3.46 (OMe, s); 3.80 (2 ArOMe, s); 5.24 (H$_{1'}$, d, J$_{1'-2'}$=6.0); 5.29 (H$_{1'}$, d, J$_{1'-2'}$=5.5). $^{31}$P—NMR (CHCl$_3$, 101 MHz, δ(ppm): 150.3, 151.2

Example A2: Preparation of compound no. 26

(Compound no. 26)

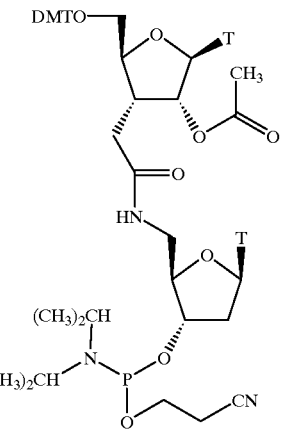

(a) A solution of 1.47 g compound no. 13

(Compound no. 13)

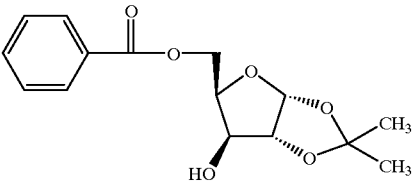

prepared as described in Pudlo, J. S., Townsend, L. B., Tetrahedron Lett. 31:3101 (1990) in 15 ml CH$_2$Cl$_2$ is added to a mixture of 2.23 g Dess-Martin reagent (Dess-Martin reagent)

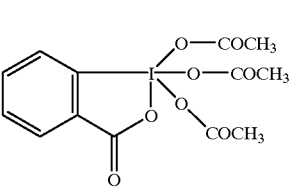

in 35 ml CH$_2$Cl$_2$. This mixture is stirred for 15 min at 0° C. and 2 h at room temperature. It is poured into 100 ml of cold, saturated NaHCO$_3$ with 12.5 g Na$_2$S$_2$O$_3$·5H$_2$O. Then the organic layer is extracted, washed with NaHCO$_3$ and a saturated solution of NaCl, dried over Na$_2$SO$_4$, filtered and evaporated. The residue is filtere over silica gel to obtain compound no. 14.

(compound no. 14)

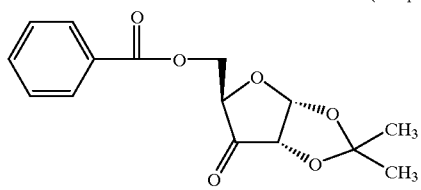

¹H—NMR (CHCl₃, 500 MHz, J(Hz)): 1.44 (3H, Me, s); 1.52 (3H, Me, s); 4.43 (H₂, d); 6.11 (H₁, d, J₁₋₂=4.6); 7.95 (2 H—Ar, dd, J=8.2, J'=1.5). M.S. (FD) (m/e): 292 M⁺.

(b) To a solution of 1.18 g compound no. 14 in 40 ml CH₂Cl₂ 1.74 gof (benzyloxycarbonylmethylene)-triphenylphosphorane are added. This mixture is stirred overnight at room temperature followed by the removal of the solvent under vacuum. The residue is chromatographed on silica gel (hexane/acetic acid ester 4:1) and compound no. 15 is obtained.

(Compound no. 15)

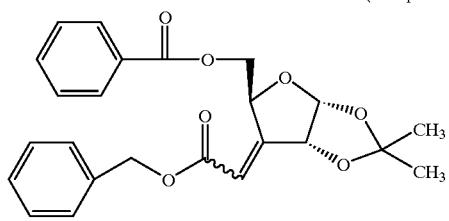

¹H—NMR (CHCl₃, 500 MHz, J(Hz)): 5.19 (2 H, s, CH₂Ph); 5.23 (2H, d, J$_{AB}$=12.2, CH₂Ph); 5.98 (H₁, d, J₁₋₂=4.5); 6.01 (H₁, d, J₁₋₂=4.9); 6.07 (=CH, t, J=1.8); 6.28 (=CH, t, J=2.0) MS (CI)(m/e): 442 (M+NH₄)⁺.

(c) 0.5 g of compound no. 15 are added to a suspension of Pd/C (10%) (0.25 g) in 30 ml methanol under an atmosphere of H₂. After 2 h stirring the mixture is filtered over Celite and evaporated and compound no. 16 is obtained.

(Compound no. 16)

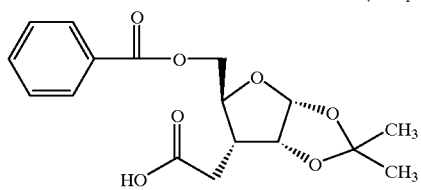

¹H—NMR (CHCl₃, 500 MHz, J(Hz): 1.33 (3H, Me, s); 1.52 (3H, Me, s); 2.55 (CH—COOH, dd, J=4.5, J'=17.2); 5.88 (H₁, d, J₁₋₂=4.0); 8.05 (2H—Ar, dd, J=8.2, J'=1.5). MS (CI) (m/e): 336 (M⁻).

(d) To a solution of 1.0 g of compound no. 16 in 40 ml acetonitrile 0.36 ml N-methylmorpholine are added at room temperature followed by the addition of 0.203 g dry hydroxybenzotriazole and 1.076 g of O—(1H-benzotriazole—1—yl)—N,N,N',N'-tetramethyluronium tetrafluoroborate. After 15 min a solution of 1.42 g of the amine, synthesized from 5'-azido-5'-deoxythymidine via 3'-protection and 5'-azido reduction by hydrogenation, and 0.49 ml N-methylmorpholine in 8 ml acetonitrile is added. After stirring overnight, aqueous NaH₂PO₄ is added and acetonitrile is removed by evaporation. The aqueous layer is extracted 3× with CHCl₃ and the combined organic extracts are washed with a saturated solution of NaCl, dried over Na₂SO₄, filtere and evaporated. The product is chromatographed on silica gel (hexane/acetic acid ester 1:1 to 1:4) to obtain compound no. 17.

(Compound no. 17)

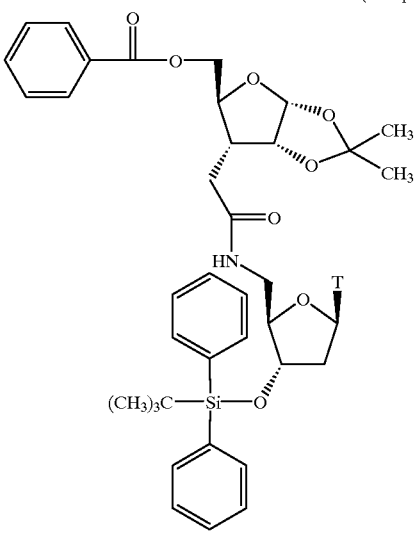

¹H—NMR (CHCl₃, 500 MHz, J(Hz)): 1.09 (9H, s, t—Bu); 1.28 (3H, s, Me); 1.50 (3H, s, Me); 5.82 (H₁, d, J₁₋₂=4.0); 6.00 (H₁', dd, J₁'₋₂'=8.0, J₁'₋₂'=7.6); 6.49 (NHCO, m); 7.02 (H₆, d, J=1.0). MS (CI)(m/e): 797 (M⁺).

(e) 0.5 g of compound no 17 are added at 0° C. to a solution of 7.2 ml CF₃COOH and 3.94 ml thiophenol under a dry atmosphere of argon. After 30 min the reaction is kept at room temperature and then vigorously stirred during 6 h. 30 ml CHCl₃ and 30 ml of a saturated solution of NaCl are added simulataneously. Thix mixture is slowly neutralized by addition of NaHCO₃. The aqueous layer is washed with a saturated solution of NaCl, dired, filtered and evaporated. The product is chromatographed on silica gel to obtain compound no. 18.

(Compound no. 18)

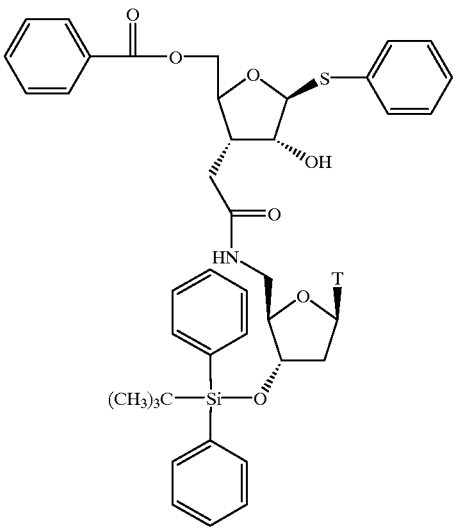

¹H—NMR (CHCl₃, 500 MHz, J(Hz)): 1.12 (9 H, s, t—Bu); 5.41 (H₁', d, J₁'₋₂'=1.6); 5.69 (H₁', t, J₁'₋₂'=7.0); 6.98 (H₆, d, J=1.0). MS (CI) (m/e): 850 (M+H)⁺.

(f) To a solution of 0.18 g compound no. 18 in 1 ml pyridine 0.2 ml acetic acid anhydride are added. After 18 h stirring at room temperature the solvent is coevaporated with toluene in vacuum. The residue is diluted with CHCl₃, washed with NaH₂PO₄ and a saturated solution of NaCl, dried over Na₂SO₄, filtered and evaporated. The product is chromatographed on silica gel (toluene/acetic acid ester 1:1) to obtain compound no. 19.

(Compound no. 19)

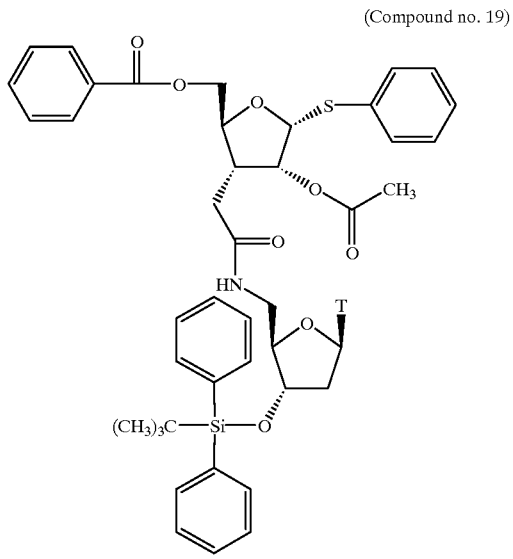

¹H—NMR (CHCl₃, 500 MHz, J(Hz)): 1.08 (9 H, s, t—Bu); 1.92 (3 H, d, J=1.6, Me); 5.43 (H$_{1'}$, s); 5.92 (H$_{1'}$, dd, J$_{1'-2a'}$=6.0, J$_{1'-2b'}$=8.2); 6.51 (1H, m, NHCO). MS (FD) (m/e): 892 (M⁺).

(g) A solution of 0.12 g of compound no. 19 with 0.095 g NaIO₄ in 2.8 ml H₂O/dioxane (1:1) is stirred at room temperature during 72 h. The dioxane is evaporated and the residue diluted with CHCl₃, washed with a saturated solution of NaCl, dried, filtered and evaporated. The product is chromatographed on silica gel (toluene/acetic ester 1:2 to 1:4) to obtain compound no. 20.

(Compound no. 20)

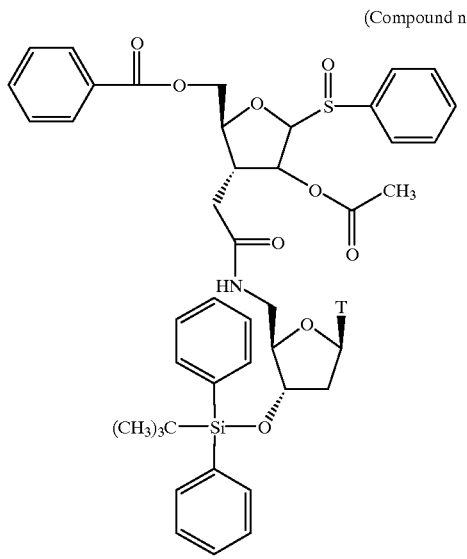

¹H-NMR (CHCl₃, 500 MHz, J(Hz)): 1.08 (9H, s, t-Bu); 1.90 (3H, d, J=1.6, Me); 4.65 (H$_{1'}$, s); 5.78 (H$_{1'}$, dd, J$_{1'-2a'}$=6.5, J$_{1'-2b'}$=7.8); 6.69 (1H, m, NHCO). MS (FD) (m/e): 906 (M—H);

(h) To a suspension of 0.011 g thymine in 0.5 ml (CH₂Cl)₂ 0.025 ml CH₃C[NSi(CH₃)₃]OSi(CH₃)₃ (0.17 mmole) are added and this mixture is kept at 90° C. After 1 h another 2.2 eq. of CH₃C[NSi(CH₃)₃]OSi(CH₃)₃ are added. After 3 h the solution is cooled to room temperature and a solution of 0.07 g compound no. 20 in 0.5 ml (CH₂Cl)₂ with 0.014 ml trimethylsilyltrifluoromethane sulfonate is added. After 20 min the mixture is cooled to 0° C. and 0.012 ml of triethylamine are added. After the addition of CH₂Cl₂ the mixture is washed with NaHCO₃ and a saturated solution of NaCl. After drying and filtration the solvent is evaporated. The product is chromatographed on silica gel (toluene/acetic acid ester 1:1 to 1:3) to obtain compound no. 21.

(Compound no. 21)

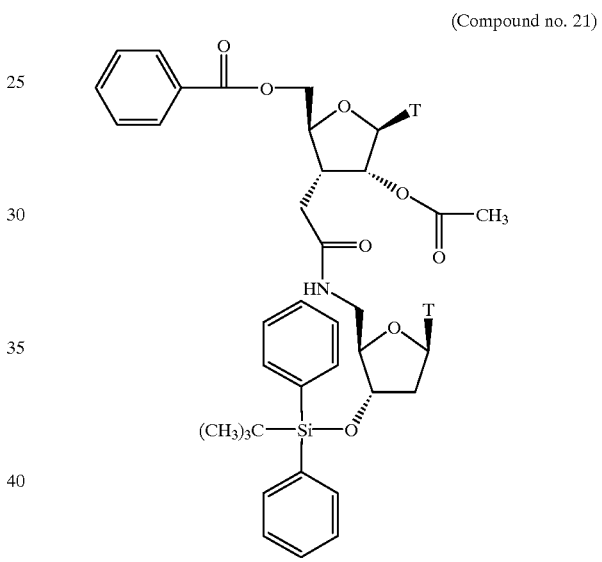

¹H-NMR (CHCl₃, 250 MHz, J(Hz)); 1.08 (9H, s, t-Bu); 2.1 (3H, s, Me); 5.43 (H$_{1'}$, dd); 5.80 (H$_{1'}$, s); 5.92 (1H, t, NHCO); 9.32 and 9.56 (1H, br. s, NH).

(i) 0.680 g of compound no. 21 (0.74·10⁻³ mole) are added at RT to a solution of 0.084 g sodium methanolate (1.56·10⁻³ mole) in 5 ml methanol. The reaction is finished after 3 hours (thin layer chromatography; ethylacetate-:methanol 9:1). The solution is neutralized by addition of Amberlyst 15 (H⁺). The resine is filtered off, the solvent is evaporated under vacuum. The residue is purified by flash chromatography on silica gel (ethylacetate:methanol; gradient 100:1 10:1) to obtain compound no. 22 (0.44 g; 0.584·10⁻³ mole: yield: 78%).

(compound no. 22)

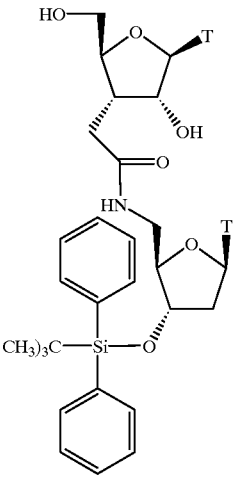

$^1$H NMR (CDCl$_3$, 250 MHz), 1.06 (9H tBu, s,); 1.82 (3H Me, d, J=1.5); 1.87 (3H Me, d, J=1.5); 5.67 (H$_1$, s); 5.89 (H$_1$, dd); 6.99 (H$_6$, q); 7.95 (H$_6$, q).

(j) 0.245 g of dimethoxytritylchloride (0.72·10$^{-3}$ mole) are added to a solution of 0.55 g compound no. 22 (0.72·10$^{-3}$ mole) in 10 ml pyridine. After 12 hours at RT, five portions of 0.074 g each dimethoxytritylchloride (0.3 eq.) are added every 4 hours. After 40 hours of stirring at RT, the mixture is diluted with CH$_2$Cl$_2$, washed with NaHCO$_3$ aq., with a saturated solution of sodium chloride in water. The solution is dried over Na$_2$SO$_4$, then evaporated under vacuum. The remaining pyridine is coevaporated with toluene under vacuum. The white residue is purified by flash chromatography on silica gel (ethylacetate:methanol; gradient 100:1 25:1, with 1% triethylamine) to obtain compound no. 23 (0.581 g; 5.46·10$^{-3}$ mole; yield: 76%).

(compound no. 23)

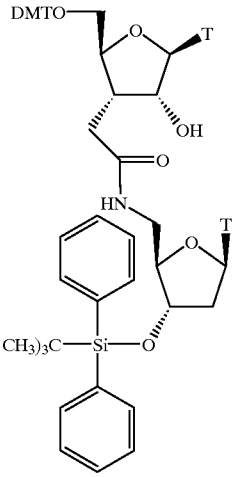

$^1$H NMR (CDCl$_3$, 500 MHz), 1.06 (9H, s, tBu); 1.82 (3H, d, Me); 1.87 (3H, d); 3.70 (6H, s, OMe); 5.67 (H$_1$, dd); 6.99 (H$_6$, q); 7.97 (H$_6$, q). MS (FAB): m/e: 1098 (M$^+$+Cl$^-$), 1063 (M$^+$).

(k) 0.564 g of compound no. 23 (0.529·10$^{-3}$ mole) are dissolved in 10 ml dry pyridine. 15 ml acetic acid anhydride are added and the mixture is stirred at RT for 20 hours. The solution is diluted with CH$_2$Cl$_2$ and washed with NaHCO$_3$ aq. After drying with Na$_2$SO$_4$, the solvents are evaporated under vacuum. The remaining pyridine is coevaporated under vacuum with toluene. The residue is chromatographied on silica gel (hexane:ethylacetate; gradient 4:1 1:3+ 1% triethylamine) to obtain compound no. 24 (0.283 g; 0.306·10$^{-3}$ mole).

(compound no. 24)

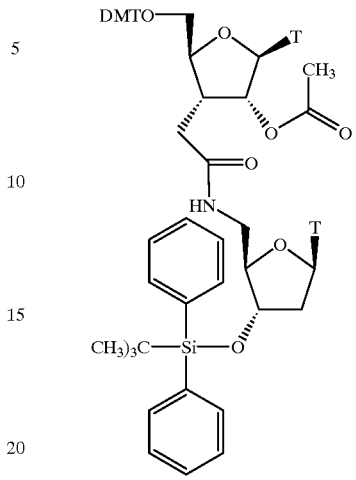

$^1$H NMR (CDCl$_3$, 500 MHz), 1.08 (9H, s); 1.45 (3H$_7$, d, J$_{6-7}$=1.0); 1.88 (3H$_{7*}$, d, J$_{6*-7*}$=1.0); 2.02 (3H OAc, s); 2.11 (H$_9$, dd, J$_{9-9'}$=15.0, J$_{9-3}$=6.7), 2,18 (H$_{2*}$, ddd, J$_{2-2*}$=14.0, J$_{2*-3*}$=2.7, J$_{2*-1*}$=6.4); 2.21 (H$_{9'}$, dd, J$_{9'-3}$=8.4); 2.39 (H$_{2'*}$, ddd, J$_{2'*-3*}$=6.3, J$_{2'*-1*}$=7.8); 3.04–3.16 (3H, m); 3.25 (H$_5$, dd, J$_{4-5}$=3.3, J$_{5-5'}$=10.8); 3.46 (H$_{5'}$, dd, J$_{5'-4}$=2.2); 3.79 (6H OMe, s); 3.96–4.02 (H$_4$, H$_{4*}$, m); 4.30 (H$_{3*}$, ddd); 5.57 (H$_2$, dd, J$_{2-1}$=3.9, J$_{2-3}$=6.6); 5.83 (H$_{1*}$, dd); 5.96 (H$_1$, d); 6.55 (H$_{10}$, dd, J$_{10-5*}$=J$_{10-5'*}$=5.0); 6.83 (4H$_{11}$, J$_{11-12}$=8.0); 6.96 (H$_{6*}$, q); 7.60–7.64 (4H$_{12}$, m); 8.26 (NH, m); 8.62 (NH, m). MS (FAB): m/e: 1140 (M$^+$+Cl$^-$); 1105 (M$^+$).

(l) 0.219 g of compound no. 24 (0.197·10$^{-3}$ mole) are dissolved in 8 ml dry tetrahydrofuran. 0.218 ml of a 1 M solution tetrabutyl ammonium fluoride (0.217·10$^{-3}$ mole; 1.1 eq.) in tetrahydrofuran are added to this solution. The mixture is stirred at 0° C. for 2 hours, then diluted with CH$_2$Cl$_2$. This solution is washed 3 times with NaH$_2$PO$_4$ aq., with a saturated solution of sodium chloride in water. The organic phase is dried over Na$_2$SO$_4$. After evaporation of the solvents under reduced pressure the residue is purified by flash chromatography on silica gel (ethylacetate:ethanol 4:1+1% triethylamine) to obtain compound no. 25 (0.154 g; 0.175·10$^{-3}$ mole: yield: 89%).

(compound no. 25)

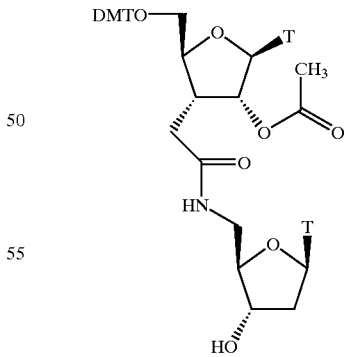

$^1$H NMR (CDCl$_3$, 500 MHz): 1.46 (3H$_7$, d); 1.90 (3H$_7$, d); 2.14 (3H OAc, s); 3.79 (6H OMe, s); 5.63 (NH, m); 5.81 (H$_1$, dd); 5.88 (H$_1$, s); 7.08 (H$_6$, q); 7.59 (H$_6$, q). MS (FAB): m/e: 866 (M$^+$–H$^+$), 902 (M$^+$+Cl$^-$).

(m) 0.144 g of compound no. 25 (0.166·10$^{-3}$ mole) are dissolved in 10 ml dry CH$_2$Cl$_2$. 0.068 g of N,N-diisopropylammonium tetrazolide (0.398·10$^{-3}$ mole) and 0.11 g of 2-cyanoethyl-N,N,N',N'-tetraisopropyl phosphoramidite ($0.364 \cdot 10^{-3}$ mole) are added to this solution. The mixture is stirred at RT for 20 hours. A saturated solution of NaHCO$_3$ aq. is added. The organic phase is separated and washed with NaHCO$_3$ aq., with a saturated solution of sodium chloride in water, dried over Na$_2$SO$_4$. After evaporation of the solvent under reduced pressure, the resin is purified by flash chromatography on silica gel (ethylacetate:methanol; gradient 100:1  20:1+1% triethylamine) to obtain compound no. 26 (0.15 g; $0.139 \cdot 10^{-3}$ mole; yield: 84 %).

$^1$H NMR (CDCl$_3$, 500 MHz): 1.46 (3H$_7$, d, J$_{6-7}$=1.0); 1.47 (3H$_7$, d, J$_{6-7}$=1.0); 1.92 (6H$_7$, d); 2.11 (OAc, s); 2.12 (OAc, s); 3.79 (6H OMe, s); 5.60 (H$_{2'}$, dd); 5.74 (H$_{1'}$, dd); 5.89 (H$_{1'}$, dd); 5.95 (H$_{1'}$, d, J$_{1'-2'}$=2.8); 5.96 (H$_{1'}$, d, J$_{1'-2'}$=2.8). $^{31}$P NMR (CDCl$_3$, 101 MHz, delta (ppm)): 149.7 and 150.2. MS (FAB): m/e: 1067 (M$^+$), 1066 (M$^+$-H$^+$).

EXAMPLE A3

Preparation of Compound No. 43

(compound no. 43)

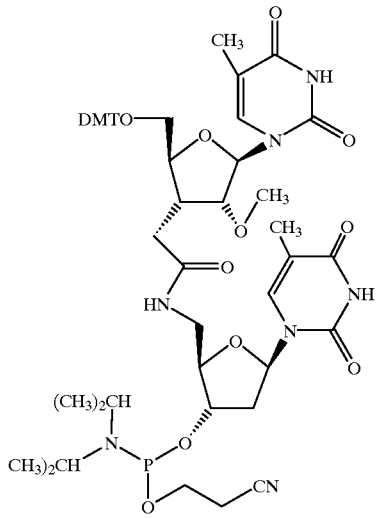

(a) To a stirred solution of 5.05 g of compound no. 27 prepared according to Codington, J. F., Doerrr, I. L., Fox, J. F., J. Org. Chem. 29:558 (1964)

(compound no. 27)

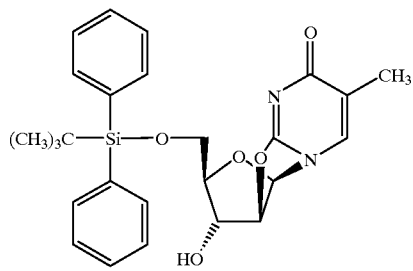

in 105 ml CH$_2$Cl$_2$ 4.26 ml pyridine, 2.94 ml triethylamine, 1.29 g dimethylamino pyridine and then 2.86 ml o-phenyl chlorothioformate are added. After 24 h stirring all reagents are added in the same amounts as at the beginning. After 56 h the product is worked up as described in example A2(g) including chromatography of the crude product to obtain compound no. 28.

(compound no. 28)

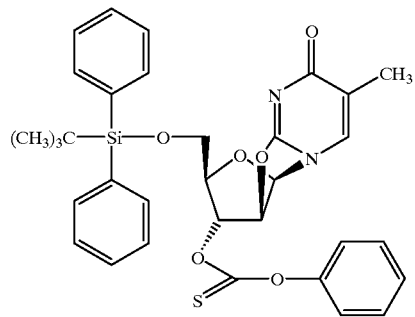

$^1$H-NMR (CHCl$_3$, 500 MHz, J(Hz)): 1.92 (3H, d, J=1.3, Me); 4.66 (1H, t, J$_{4'-5a'}$=J$_{4'-5b'}$=6.9, H$_{4'}$); 5.49 (1H, d, J$_{2'-1'}$=5.8, H$_{2'}$); 5.96 (1H, br. s, H$_{3'}$); 6.25 (1H, d, J$_{1'-2'}$=5.8, H$_{1'}$). MS (FD) (m/e): 615 (M$^+$).

(b) To a stirred solution of 4.36 g of compound no. 28 in 70.9 ml benzene 0.58 g of azobisisobutyronitrile are added, followed by the addition of 10.7 ml tributylallylstannane. The reaction is kept at 80° C. for 18 h. Another 0.29 g of azobisisobutyronitrile are added. After 22 h the mixture is concentrated and the product is chromatographed on silica gel (hexane/acetic acid ester: 2:1 to pure acetic acid ester, then acetic acid ester/methanol 10:1) to obtain compound no. 29.

(compound no. 29)

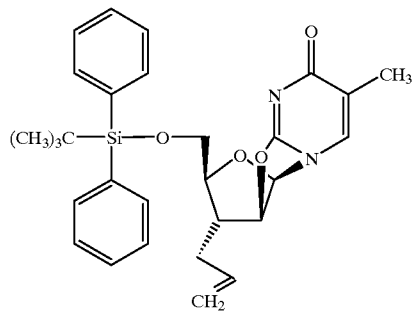

$^1$H-NMR (CHCl$_3$, 250 MHz, J(Hz)): 1.00 (9H, s, t-Bu); 1.91 (3H, d, J=1.3, Me); 5.06 (1 H, dd, H$_{2'}$); 5.75 (1H, m, CH=C); 6.00 (1H, d, J$_{1'-2'}$=5.5, H$_{1'}$).

(c) 0.5 g of compound no. 29 are diluted in 6.4 ml of freshly distilled tetrahydrofuran and 3.2 ml water are added. After cooling to 0° C., 0.96 ml 2 N NaOH are added and the solution is stirred for 1 h and 4 h at room temperature. After neutralization with 1 N HCl extraction with CHCl$_3$ is carried out 4×. The organic layers are washed with a saturated solution of NaCl, dried and evaporated. The residue is chromatographed on silica gel affording compound no. 30.

(compound no. 30)

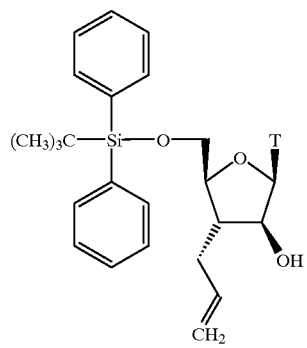

¹H-NMR (CHCl₃, 500 MHz, J(Hz)): 1.12 (9H, s, t-Bu); 1.71 (3H, d, J=1.4, Me); 4.16 (1 H, m, H₂·); 6.00 (1H, d, J₁·₋₂·=4.0, H₁·). MS (FD) (m/e): 521 (M⁺).

(d) To a stirred solution of 0.44 g of compound no. 30 in 4 ml acetonitrile 0.15 ml 1,5-diazabicyclo-[5.4.0.]-undec-5-en and 0.13 ml benzyloxymethylchloride are added. After 18 h at room temperature an aqueous solution of NaH₂PO₄ is added. The organic solvent is removed in vacuum and the aqueous phase is extracted with CHCl₃. The organic layer is washed with a saturated solution of NaCl, dried and concentrated. The product is chromatographed on silica gel affording compound no. 31.

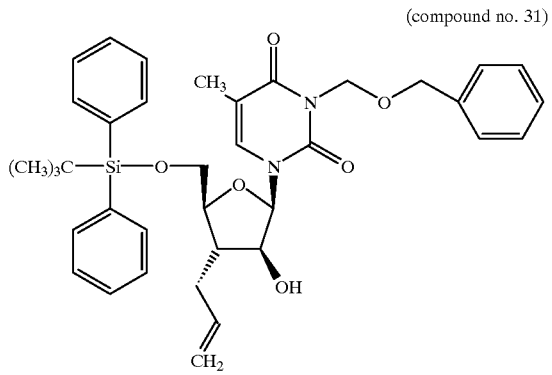

(compound no. 31)

¹H-NMR (CHCl₃, 500 MHz, J(Hz)): 1.12 (9H, s, t-Bu); 1.74 (3H, d, J=1.6 , Me); 4.19 (1 H, dt, J₂·₋OH=8.5, J₁·₋₂·=J₂·₋₃·= 3.8, H₂·); 5.51 (2H, AB, J=13.2, NCH₂O); 6.03 (1H, d, J₁·₋₂·=3.8, H₁·). MS (FD) (m/e): 641 (M⁺).

(e) A solution of 2.23 g triphenyl phosphine and 1.73 ml diisopropylazodicarboxylate in 30 ml of dry toluene is stirred for 1 h at 0° C. under argon. The solution is warmed to room temperature and 2.18 g of compound no. 31 in 15 ml of toluene are added. After 10 min 0.96 g of chloroacetic acid are added. After stirring for 56 h the solvent is removed and the residue is chromatographed on silica gel affording compound no. 32.

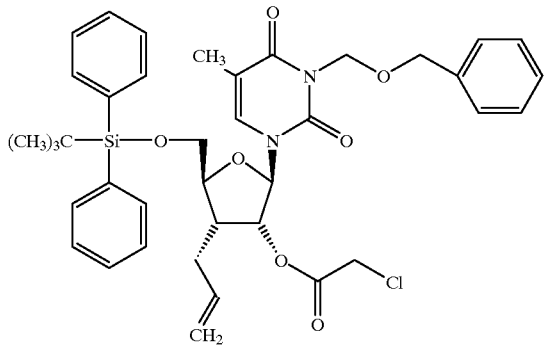

(compound no. 32)

¹H-NMR (CHCl₃, 500 MHz, J(Hz)): 1.11 (9H, s, t-Bu); 1.57 (3H, s, Me); 5.55 (1H, dd, J=6.2, J=2.1, H₂·); 5.92 (1H, d, J₁·₋₂·=2.1, H₁·). MS (FD) (m/e): 717 (M⁺).

(f) To a solution of 0.24 g of compound no. 32 in 10 ml methanol 10 ml of a solution of sodium methanolate (0.009 g Na in 1 ml methanol) are added at room temperature under argon. After 30 min the mixture is neutralized by slow addition of H⁺-ion exchange resin. This mixture is filtered and evaporated to obtain compound no. 33.

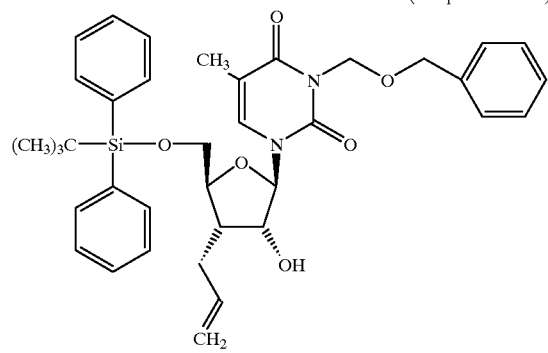

(compound no. 33)

¹H-NMR (CHCl₃, 500 MHz, J(Hz)): 1.10 (9H, s, t-Bu); 1.57 (3H, s, Me); 4.28 (1H, dd, J₂·₋₃·=5.3, J₁·₋₂·=1.0, H₂·); 5.49 (2H, s, NCH₂O); 5.65 (1H, d, J₁·₋₂·=1.0, H₁·). MS (FD) (m/e): 641 (M⁺).

(g) A suspension of 0.69 g Ag₂O and 0.19 g of compound no. 33 in 5 ml CH₃I is kept at 45° C. for 20 h. The excess CH₃I is distilled off and the residue is diluted with CHCl₃, filtered and concentrated. Chromatography or silica gel affords compound no. 34.

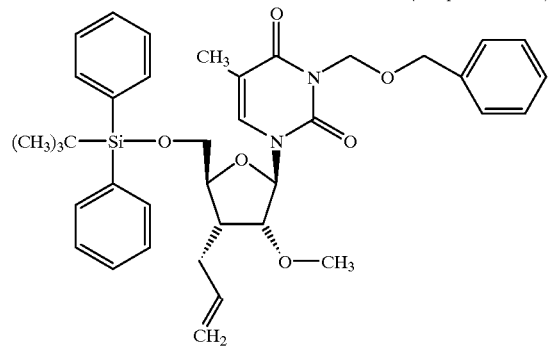

(compound no. 34)

¹H-NMR (CHCl₃, 500 MHz, J(Hz)): 1.10 (9H, s, t-Bu); 1.46 (3H, d, J=1.6, Me); 3.60 (3 H, s, McO); 4.72 (2H, s, PhCH₂O); 5.06 (2H, m, C=CH₂); 5.87 (1H, d, J₁·₋₂·=1.0, H₁·).

(h) To a stirred suspension of 0.084 g NaH in 6 ml tetrahydrofuran 0.83 g of compound no. 33 are added at 0° . After 1 h 0.12 ml CH₃I is added and the reaction is kept at room temperature. After 18 h the solvent is removed under vacuum and the residue is diluted with CHCl₃, washed with Na₂S₂O₃, NaH₂PO₄ and a saturated solution of NaCl, dried over Na₂SO₄ and evaporated. The residue is chromatographed on silica gel to obtain compound no. 34.

(i) To a stirred solution of 0.83 g of compound no. 34 in acetone/H₂O (4:1) 0.188 g of 4-methylmorpholine-4-oxide monohydrate and then 0.032 g of OsO₄ are added at room temperature. After 17 h the solvent is removed under vacuum. The residue is diluted with CHCl₃, washed with a saturated solution of NaCl, dried, filtered and evaporated. The residue is chromatographed on silica gel to obtain compound no. 35.

(compound no. 35)

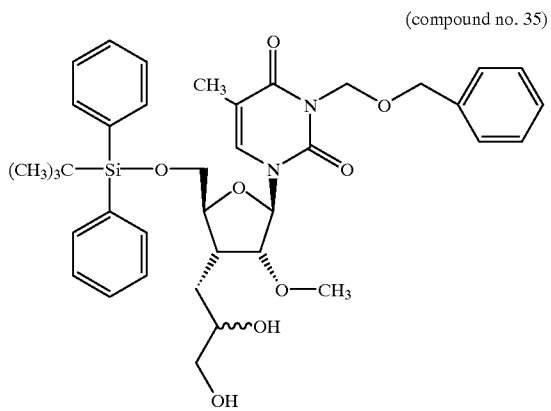

(j) A solution of 0.735 g of compound no. 35 in 10 ml methanol with 0.735 g Pd/C is stirred overnight under an atmosphere of hydrogen at room temperature. The solution is filtered and evaporated under vacuum. The residue is chromatographed on silica gel to obtain compound no. 36.

(compound no. 36)

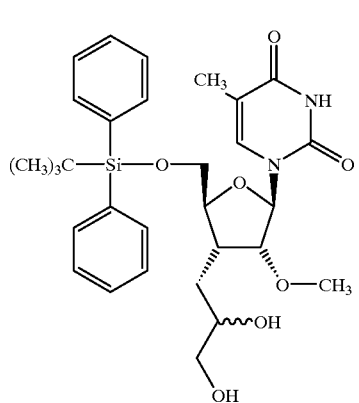

(k) A solution of 0.49 g of compound no. 36 and 0.203 g of NaIO$_4$ in 5 ml of a mixture of dioxane/H$_2$O (3:1) is stirred for 18 h at room temperature. The solvent is removed and the residue is diluted with CHCl$_3$, washed with a saturated solution of NaCl and dried. After evaporation chromatography on silica gel affords compound no. 37.

(compound no. 37)

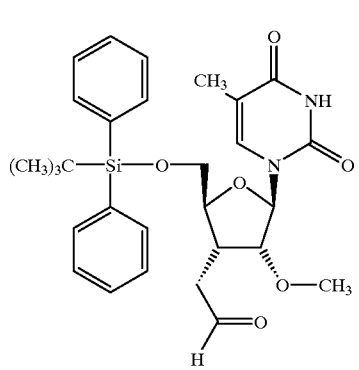

(l) To a stirred solution of 0.37 g of compound no. 37 in 2.3 ml t-butanol 0.374 g of NaClO$_2$, 0.29 ml 2-methyl-2-butene and 0.381 g NaH$_2$PO$_4$ in 1.4 ml water are added at room temperature. After 30 min the solution is evaporated under vacuum. The residue is taken up in a saturated solution of NaCl and extracted three times with CHCl$_3$. The organic phase is dried and evaporated to afford compound no. 38.

(compound no. 38)

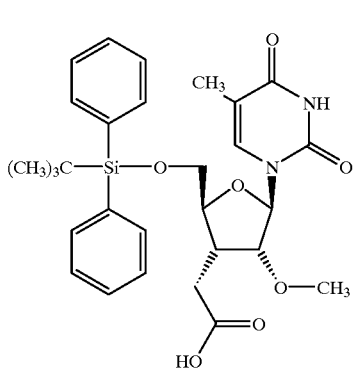

(m) To a solution of 0.33 g of compound no. 38 in 3 ml acetonitrile 0.073 ml of N-methyl-morpholine, morpholine, 0.041 g of hydroxybenzotriazole and then 0.22 g of (1-H-benzotriazol-1-yl) N,N,N',N'-tetramethyluronium tetrafluoroborate are added at room temperature. After 30 min a solution of 0.29 g of compound no. 39, synthesized from 5'-azido-5'-deoxythymidine via 3'-protection and 5'-azido reduction by hydrogenation, (compound no. 39)

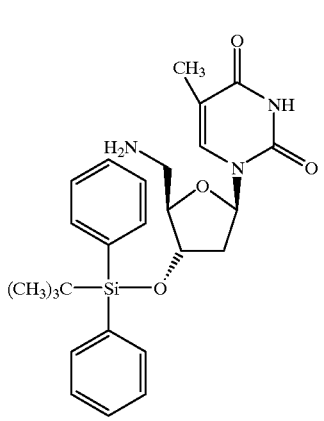

is added with 1.5 eq. of N-methylmorpholine in 2 ml acetonitrile. After 17 h aqueous NaH$_2$PO$_4$ is added. Acetonitrile is removed under vacuum. The aqueous phase is extracted with CHCl$_3$, the organic phase is washed with a saturated solution of NaCl, dried and evaporated. Chromatography on silica gel affords compound no. 40.

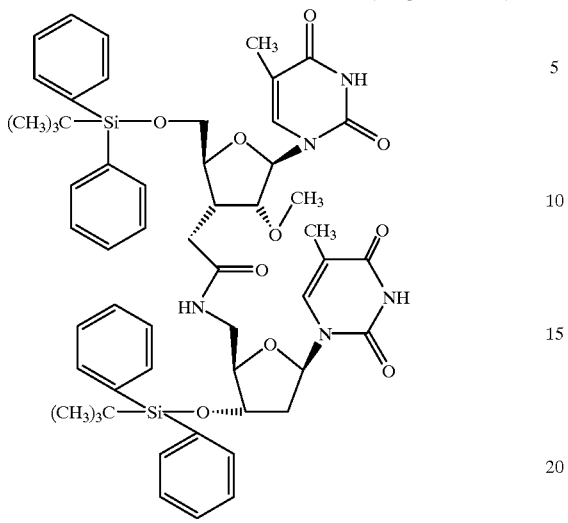
(compound no. 40)

(n) To a solution of 0.42 g of compound no. 40 in 4 ml tetrahydrofuran 0.06 ml acetic acid and 0.91 ml of a 1 M solution of tetrabutylammonium fluoride in tetrahydrofuran are added at room temperature. After 16 h triethylamine is added and the mixture is co-evaporated with toluene. The residue is chromatographed on silica gel to afford compound no. 41.

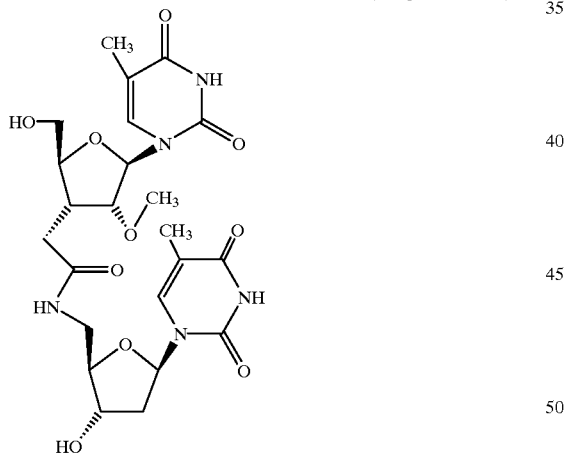
(compound no. 41)

(o) 0.146 g of dimethoxytritylchloride ($0.424 \cdot 10^{-3}$ mole) are added to a stirred solution of 0.19 g of compound no. 41 ($0.353 \cdot 10^{-3}$ mole) in 6 ml dry pyridine. The mixture is stirred at RT. Four portions of 0.036 g each dimethoxytritylchloride ($0.106 \cdot 10^{-3}$ mole) are added every 6 hours. The solution is diluted with $CH_2Cl_2$, washed with $NaHCO_3$ aq., with a saturated solution of sodium chloride in water, dried over $Na_2SO_4$. The solvents are evaporated under vacuum. The residue is purified by flash chromatography on silica gel (ethylacetate:methanol; gradient 100:1 20:1+1% triethylamine) to obtain compound no. 42 (0.245 g, $0.289 \cdot 10^{-3}$ mole; yield: 82%).

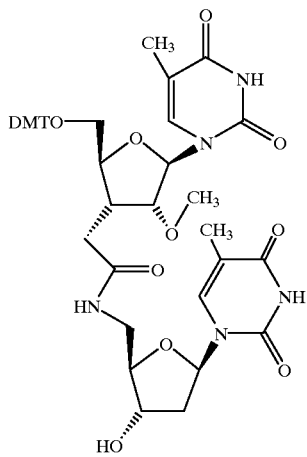
(compound no. 42)

$^1$HNMR (CDCl$_3$, 400 MHz): 1.48 (3H$_7$, d, J$_{7-6}$=1.0); 1.89 (3H$_7$, d, J$_{6-7}$=1.1); 3.66 (OMe, s); 3.79 (OMe, s); 3.80 (OMe, s); 5.86 (H$_1$, s); 5.95 (H$_1$, dd, $^3$J$_{1-2}$=7.0, $^3$J$_{1-2}$=7.5); 7.15 (H$_6$, q); 7.66 (H$_6$, q). MS (FAB): m/e: 874 (M$^+$+Cl$^-$), 838 (M$^+$–H$^+$).

(p) 0.23 g of compound no. 42 ($0.273 \cdot 10^{-3}$ mole) are dissolved in 10 ml dry $CH_2Cl_2$. 0.112 g of N,N-diisopropylammonium tetrazolide ($0.657 \cdot 10^{-3}$ mole) and 0.182 g 2-cyanoethyl-N,N,N',N'-tetraisopropyl phosphoramidite ($0.602 \cdot 10^{-3}$ mole) are added to this solution. The mixture is stirred at RT for 24 hours. A saturated solution of NaHCO$_3$ aq. is added. The organic phase is separated and washed with NaHCO$_3$ aq., with a saturated solution of sodium chloride in water, dried over Na$_2$SO$_4$. After evaporation of the solvent under vacuum, the residue is purified by flash chromatography on silica gel (ethylacetate:methanol; gradient 100:1 97:3, +1% triethylamine) to obtain compound no. 43 (0.21 g; $0.202 \cdot 10^{-3}$ mole; yield: 74%). $^{31}$P NMR (CDCl$_3$, 101 MHz, delta (ppm)): 148.7 and 149.6.

EXAMPLE A4

Preparation of Compound No. 51

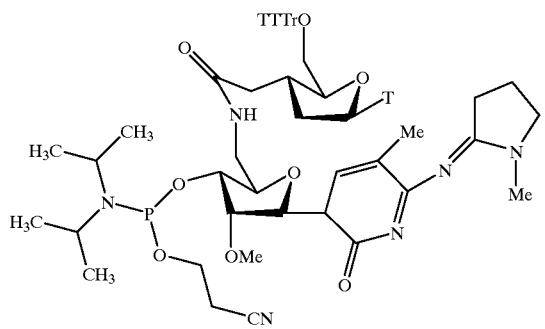
(compound no. 51)

(a) 26.84 g of compound no. 44 (0.0501 mole)

(compound no. 44)

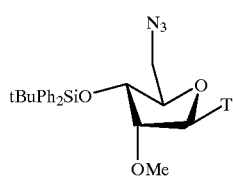

are dissolved in 80 ml of dry pyridine. To this solution 18.44 g 4-chlorphenylphosphordichlorate (0.0751 mole) and 10.47 g 1,2,4-triazole (0.1503 mole) are added at RT. The reaction mixture is heated at 50° C. for 24 hours, then diluted with $CH_2Cl_2$ and washed with $NaH_2PO_4$ aq., with a saturated solution of sodium chloride in water. The organic phase is dried over $Na_2SO_4$. The residue is further transformed without purification. The residue is dissolved in 100 ml of dioxane (100 ml). To this solution 50 ml of concentrated ammoniac (25% in water) is added. The mixture is stirred at RT for 23 hours, then extrated with $CH_2Cl_2$. The water phase is saturated with NaCl and extracted with $CH_2Cl_2$. The organic phases are dried over $Na_2SO_4$. The solvent is evaporated under vacuum and the residue is purified by flash chromatography on silica gel (:methanol gradient 50:1 9:1) to obtain compound no. 45 (24.61 g; 0.0456 mole: yield= 91%).

(compound no. 45)

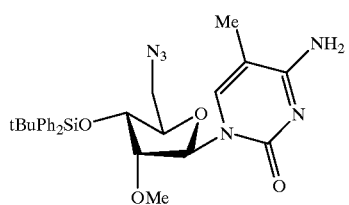

$^1$H NMR (CDCl$_3$, 500 MHz, J (Hz)); 1.10 (9H tBu, s); 1.83 (3H$_7$, d, J$_{6-7}$=1.0); 3.24 (H$_2$, dd, J$_{2-3}$=5.0, J$_{2-1}$=1.1); 3.45 (3H OMe, s); 3.46 (H$_5$, dd, J$_{5-5'}$=13.5, J$_{5-4}$=3.0); 3.80 (H$_{5'}$, dd, J$_{5'-4'}$=2.8); 3.95 (H$_3$, dd, J$_{3-4}$=8.8); 4.20 (H$_4$, ddd); 5.91 (H$_1$, d); 7.36 (H$_6$, q). MS(FD): m/e: 535 (M$^+$).

(b) 0.251 g of compound no. 45 (0.469·10$^{-3}$ mole) are dissolved in 5 ml dry pyridine. 0.136 g N-methylpyrrolidone dimethylacetal (0.938·10$^{-3}$ mole) are added. This mixture is stirred at RT for 16 hours. The pyridine is coevaporated 3 times with toluene under vacuum. The residue is purified by flash chromatography on silica gel (ethylacetate:methanol; gradient 20:1 10:1) to obtain compound no. 46 (0.276 g; 0.445·10$^{-3}$ mole; yield: 95%).

(compound no. 46)

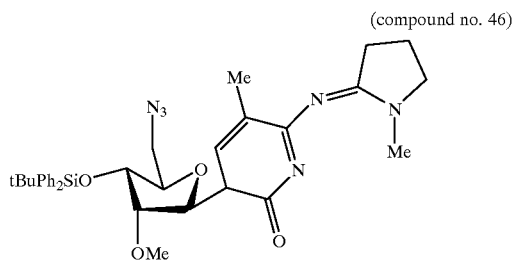

$^1$H NMR (CDCl$_3$, 500 MHz, J (Hz)): 1.10 (9H tBu, s); 1.88 (3H$_7$, d, J$_{6-7}$=1.0); 2.04 (2H$_9$, m); 3.06 (3H NMe, s), 3.13 (H$_{10}$, m); 3.17 (H$_{10'}$, m); 3.17 (H$_{10'}$, m); 3.30 (H$_2$, dd, J$_{2-3}$=5.1; J$_{1-2}$=1.0); 3.43 (H$_5$, dd, J$_{5-4}$=3.5); 3.43–3.47 (2 Hg, m); 3.45 (3H OMe, s), 3.75 (H$_{5'}$, dd, J$_{5-5'}$=13.4, J$_{5'-4}$=2.9); 4.02 (H$_3$, dd, J$_{3-4}$=8.6); 4.20 (H$_4$, ddd), 5.95 (H$_1$, d); 7.30 (H$_6$, q).

(c) 4 g of compound no. 46 (6.49·10$^{-3}$ mole) are dissolved in 60 ml methanol. 1.466 g SnCl$_2$·2H$_2$O (6.49·10$^{-3}$ mole) are added to this solution three times: at 0.60 and 90 minutes each. After 2 hours of vigorous stirring at RT, a saturated solution of NaHCO$_3$ aq. is added. The pH of the solution is brought to pH=9. The methanol is evaporated under vacuum. The water phase is extracted with CH$_2$Cl$_2$. The organic phase is washed with a saturated solution of sodium chloride in water and dried over Na$_2$SO$_4$. The crude product, compound no. 47, is used without purification in the next step (3.50 g; 5.9·10$^{-3}$ mole; yield: 91%).

(compound no. 47)

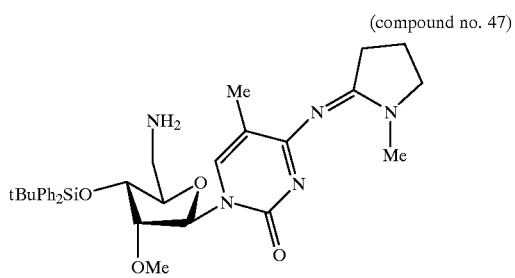

$^1$H NMR (CDCl$_3$, 250 MHz): 1.10 (9H tBu, s); 1.86 (3H$_7$, d, J$_{1-2}$=1.3).

(d) 1.104 g compound no. 48 (1.588·10$^{-3}$ mole)

(compound no. 48)

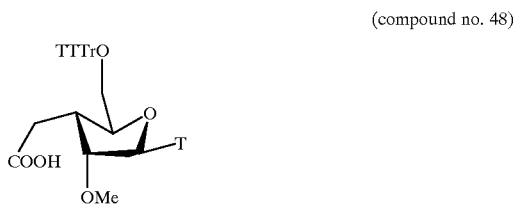

are dissolved in 20 ml acetonitrile (dry). 0.176 g of triethylamine (1.74·10$^{-3}$ mole), 0.561 g O-(1H-benzotriazol-1-yl)-N,N,N',N'-tetramethyluronium tetrafluoroborate (1.74·10$^{-3}$ mole) and 0.107 g N-hydroxybenzotriazole (0.79·10$^{-3}$ mole) are added to this solution. This mixture is stirred at RT for 1 hour. 0.935 g compound no. 47 (1.588·10$^{-3}$ mole) are added followed by 0.241 g triethylamine (2.38·10$^{-3}$ mole). After 12 hours at RT, a saturated solution of NaH$_2$PO$_4$ is introduced in the reaction flask. The solvent is evaporated under vacuum, the water phase is extracted with CH$_2$Cl$_2$. The organic phase is dried over Na$_2$SO$_4$. After evaporation of the solvent, the residue is purified by flash chromatography on silica gel (ethylacetate:methanol: gradient 100:1 10:1) to obtain compound no. 49 (1.407 g; 1.106.10$^{-3}$ mole: yield: 70%).

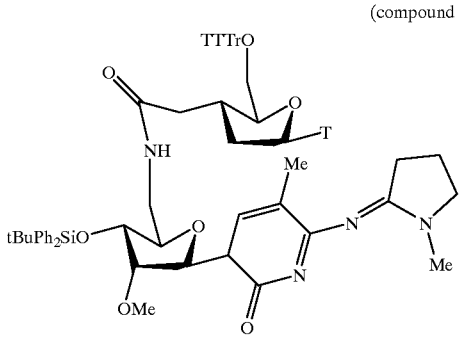

(compound no. 49)

$^1$H NMR (CDCl$_3$, 500 MHz): 1.10 (9H tBu, s); 1.30 (27H tBu, s); 1.35 (3H$_7$, d, J$_{6-7}$=1.0); 1.96 (3H$_7$, d, J$_{6-7}$=1.0); 3.05 (3H NMe, s); 3.08 (3H OMe, s); 5.18 (H$_1$, d, J$_{1-2}$=5.9); 6.10 (H$_1$, dd, J$_{1-2}$=3.1, J$_{1-2'}$=7.0). MS(FAB); m/e 1265 (M$^+$).

(e) 0.470 g of compound no. 49 (0.371·10$^{-3}$ mole) are dissolved in 20 ml dry tetrahydrofuran. 0.107 g tetrabutyl ammonium fluoride (0.408 ml of a 1 M solution in tetrahydrofuran) are added to this solution. After 2 hours at RT, the solvent is evaporated under vacuum. The residue is purified by flash chromatography on silica gel (ethylacetate:methanol: gradient 100:1 10:1) to obtain compound no. 50 (0.81 g; 0.304·10$^{-3}$ mole; yield: 82%).

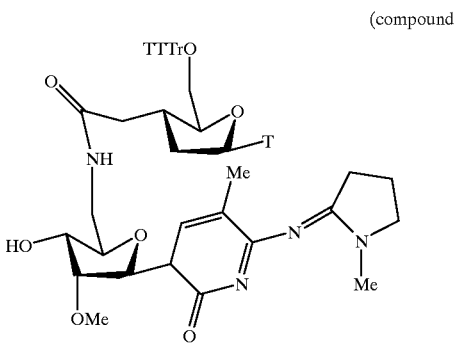

(compound no. 50)

$^1$H NMR (CDCl$_3$, 500 MHz, J (H$_Z$)): 1.30 (27H tBu, s); 1.36 (3H$_7$, d, J$_{6-7}$=1.0); 1.98 (3H$_7$, d, J$_{6-7}$=1.0); 2.07 (2H$_9$, m); 2.23 (1H$_2$, ddd, J$_{2-2'}$=16.2, J$_{2-1}$=7.0 J$_{2-3}$=9.2); 2.31–2.44 (3H, m); 3.07 (3H NMe, s); 3.18 (H$_5$, ddd, J$_{5-5'}$=14.0, J$_{5-10}$=2.2, J$_{5-4}$=3.0); 3.25 (H$_{10}$, ddd); 3.31 (H$_5$, dd, J$_{5-4}$=3.5, J$_{5-5'}$=10.9); 3.46–3.51 (2 Hg, m); 3.47 (3H OMe, s); 3.51 (H$_5$, dd, J$_{5-4}$=2.3); 3.92 (H$_5$, ddd, J$_{5-4}$=2.6, J$_{5-10}$=8.0); 3.95 (H$_4$, ddd, J$_{3-4}$=8.3); 4.16 (H$_4$, ddd, J$_{3-4}$=3.6); 4.24 (H$_3$, ddd); 4.71 (H$_2$, dd, J$_{2-3}$=5.7); 5.15 (H$_1$, d, J$_{1-2}$=5.5); 6.11 (H$_1$, dd, J$_{1-2}$=3.1); 7.08 (H$_6$, q); 7.75 (H$_6$, q). MS(FAB): m/e: 1027 (M$^+$).

(f) 0.24 g of compound no. 50 (0.233·10$^{-3}$ mole) are dissolved in 10 ml dry CH$_2$Cl$_2$. 0.096 g of N,N-diisopropylammonium tetrazolide (0.56·10$^{-3}$ mole) and 0.155 g of 2-cyanoethyl-N,N,N',N'-tetraisopropyl phosphoramidite (0.513·10$^{-3}$ mole) are added to this solution. The mixture is stirred at RT for 24 hours. A saturated solution of NaHCO$_3$ aq. is added. The organic phase is separated and washed with NaHCO$_3$ aq., with a saturated solution of sodium chloride in water, dried over Na$_2$SO$_4$. After evaporation of the solvent under vacuum, the residue is purified by flash chromatography on silica gel (ethylacetate:methanol; gradient 100:1 25:1) to obtain compound no. 51 (0.225 g; 0.184·10$^{-3}$ mole; yield: 79%). $^{31}$P NMR (CDCl$_3$, 101 MHz, delta (ppm)): 150.7 and 151.3.

EXAMPLE A5

Preparation of Compound No. 71

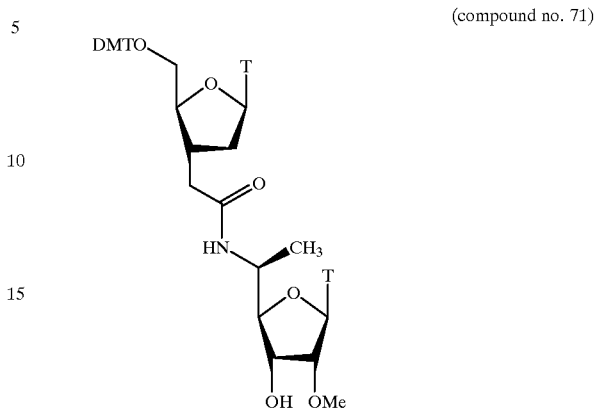

(compound no. 71)

(a) A solution of 47.5 mg of compound no. 52 (0.182 mol)

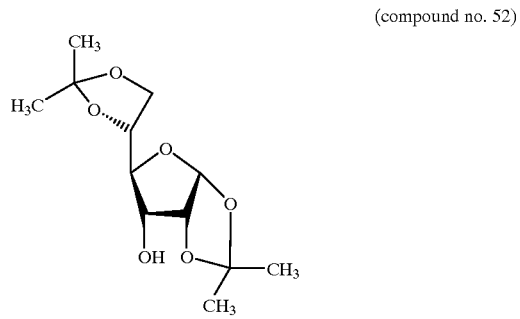

(compound no. 52)

in 70 ml tetrahydrofuran is added to a suspension of NaH (8.76 g, 55%, 0.201 mol, washed with hexane) in 110 ml tetrahydrofuran at 0° C. The reaction is stirred for 1.0 h at 0° C. and 0.5 h at 25° C. 46.7 g of benzylbromide (0.273 mol) and 3.36 g of tetrabutyl ammonium iodide (9.1 mmol) are added to the reaction mixture and stirring is continued for 1.0 h at 25° C. The reaction mixture is poured into a saturated, aqueous solution of NH$_4$Cl and extracted with ethylacetate (3×). The combined organic layers are washed with a saturated solution of sodium chloride in water, dried (Na$_2$SO$_4$), concentrated and purified by flash chromatography (silica, 20% ethylacetate in hexane) to give compound no. 53 (55.0 g, 86%).

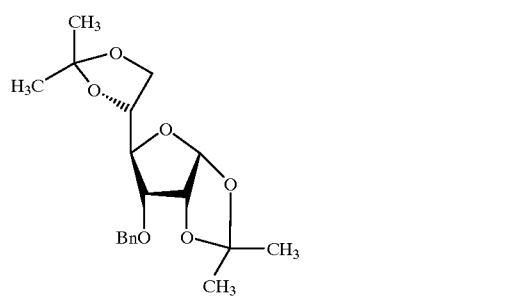

(compound no. 53)

R$_f$=0.30 (silica, 30% ethylacetate in hexane) $^1$H NMR (500 MHz, CDCl$_3$): d=7.45–7.30 (m, 5H, Harom); 5.77 (d, J=4 Hz, 1H, H—C(1')); 4.79, 4.60 (2 d, J=12 Hz, 2H, Hbenzyl);

4.59 (dd, partially covered, J=4, 4 Hz, 1H, H—C(2')); 4.38 (ddd, J=7, 7, 3 Hz, 1H, H—C(5')); 4.15 (dd, J=9, 3 Hz, 1H, H—C(4')); 4.00 (m, 2H, H—C(6')); 3.90 (dd, J=9, 4 Hz, 1H, H—C(3')); 1.60, 1.40, 1.38, 1.37 (4 s, 12H, $CH_3$) MS (FD): 350 (M)

(b) 55.0 g of compound no. 53 (0.157 mol) are dissolved in $AcOH/H_2O$ (9/1, 1105 ml) and stirred for 2.0 h at 40° C. The reaction mixture is concentrated, coevaporated with toluene (3×) and purified by flash chromatography (silica, 65% ethylacetate in hexane) to give diol compound no. 54 (29.0 g, 60%).

(compound no. 54)

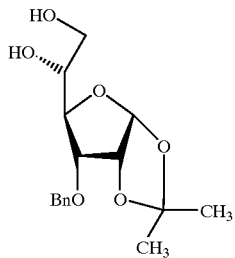

$R_f$=0.29 (silica, 80% ethylacetate in hexane) $^1$H NMR (500 MHz, $CDCl_3$): d=7.28 (m, 5H, Harom); 6.78 (d, J=4 Hz, 1H, H—C(1')); 4.80, 4.56 (2 d, J=12 Hz, 2H, benzyl); 4.62 (dd, J=4, 4 Hz, 1H, H—C(2')); 4.12 (dd, J=9, 4 Hz, 1H, H—C(4')); 4.01 (m, 1H, H—C(5')); 3.94 (dd, J=9, 4 Hz, 1H, H—C(3')); 3.70 (m, 2H, H—C(6')); 2.57, 2.49 (2 bs, 2H, OH); 1.60, 1.37 (2 s, 6H, $CH_3$) MS(FD): 310 (M)

(c) A solution of 29.0 g of compound no. 54 (93.5 mmol) in 250 ml pyridine is treated with 25.0 g of toluene-4-sulfonyl-chloride (130.9 mmol) and 1.1 g of dimethylamino pyridine (9.4 mmol) at 0° C. The reaction is stirred for 4.0 h at 25° C., quenched with 11 ml methanol, stirred for additional 0.3 h, concentrated, coevaporated with toluene (2×) and purified by flash chromatography to give compound no. 55 (36.8 g, 85%).

(compound no. 55)

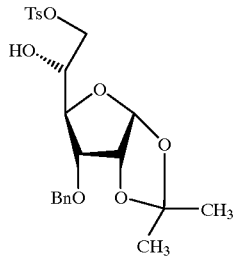

$R_f$=0.50 (silica, 25% ethylacetate in hexane) $^1$H NMR (500 MHz, $CDCl_3$): d=7.7 (m, 2H, Harom); 7.39–7.29 (m, 2H, Harom); 5.71 (d, J=4 Hz, 1H, H—C(1=)); 4.55 (dd, 1H, H—C(2')); 4.72, 4.52 (2 d, AB, J=12 Hz, 2H, Hbenzyl); 4.13 (m, 2H, H—C(5',6')); 4.05 (dd, J=11, 9 Hz, 1H, H—C(6')); 4.00 (dd, J=9, 4 Hz, 1H, H—C(4')); 3.88 (dd, J=9, 4 Hz, 1H, H—C(3')); 2.44 (s, 3H, $ArCH_3$); 2.35 (d, J=3 Hz, 1H, OH); 1.57, 1.35 (2 s, 6H, $CH_3$) MS(FD): 464 (M)

(d) A solution of 11.7 g of compound no. 55 (25.3 mmol) in 83 ml dimethoxy ethane (degassed with Argon) is treated with 11.4 g of NaI (76.0 mmol), 11.1 g of trityl tin hydride (38.0 mmol) and 410 g of azoisobutyronitrile (0.25 mmol) and stirred for 1.0 h at 80° C. The reaction mixture is adsorbed onto silica gel, concentrated and purified by flash chromatography (silica, 30% ethylacetate in hexane) to give compound no. 56 (7.5 g, 73%).

(compound no. 56)

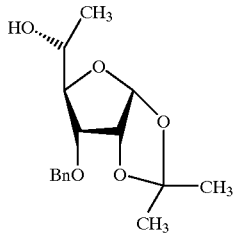

$R_f$=0.13 (silica, 35% ethylacetate in hexane) $^1$H NMR (400 MHz, $CDCl_3$): d=7.35 (m, 5H, Harom); 5.74 (d, J=4 Hz, 1H, H—C(1')); 4.76, 4.57 (2 d, J=12 Hz, 2H, Hbenzyl); 4.58 (m, 1H, H—C(2')); 4.08–3.80 (m, 2H, H—C(4',5')); 3.88 (dd, J=8, 4 Hz, 1H, H—C(3')); 2.14 (d, J=2 Hz, 1H, OH); 1.60, 1.37 (2 s, 6H, $CH_3$); 1.23 (d, J=6 Hz, 3H, H—C(6')) MS (CI): 312 ($M+NH_4^+$), 254 ($M—C_3H_6O+NH_4^+$)

(e) A solution of 12.5 g of compound no. 56 (42.6 mmol) in 125 ml pyridine at 0° C. is treated with 20.3 g of toluene-4-sulfonyl-chloride (106 mmol) and 520 g of dimethylamino pyridine (4.3 mmol). The reaction is slowly heated to 70° C. and stirred for 3.0 h. The reaction mixture is poured into aqueous, saturated $NH_4Cl$ solution, extracted with $CH_2Cl_2$ (3×), dried ($Na_2SO_4$), concentrated and purified by flash chromatography (silica, 25–35% ethylacetate in hexane) to give compound no. 57 (15,9 g, 84%).

(compound no. 57)

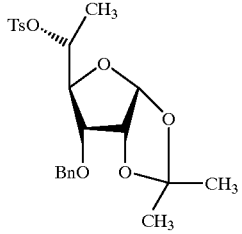

$R_f$=0.31 (silica, 33% ethylacetate in hexane) $^1$H NMR (500 MHz, $CDCl_3$): d=7.76–7.25 (m, 10H, Harom); 5.42 (d, J=4 Hz, 1H, H—C(1')); 4.85 (dq, J=6, 2 Hz, 1H, H—C(5')); 4.73, 4.55 (2 d, J=11 Hz, 2H, Hbenzyl); 4.48 (dd, J=4, 4 Hz, 1H, H—C(2')); 4.01 (dd, J=8, 2 Hz, 1H, H—C(4')); 3.85 (dd, J=8, 4 Hz, 1H, H—C(3')); 2.43 (s, 3H, $ArCH_3$); 1.52 (s, 3H, $CH_3$); 1.34 (d, J=6 Hz, 3H, H—C(6')); 1.32 (s, 3H, $CH_3$) MS(CI): 448 ($M^-$), 357 ($M—PhCH_2$)

(f) A solution of 15.9 g of compound no. 57 (36.0 mmol) in 120 ml dimethylformamide is treated with 4.6 g of $NaN_3$ (71.2 mmol) and stirred at 80° C. for 3.0 h. The reaction mixture is poured into a saturated solution of sodium chloride in water and extracted with ethylacetate (3×). The combined organic layers are dried ($Na_2SO_4$), concentrated and purified by flash chromatography (silica, 20% ethylacetate in hexane) to give compound no. 58 (10.6 g, 93%).

(compound no. 58)

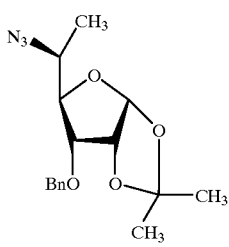

R$_f$=0.42 (silica, 20% ethylacetate in hexane) $^1$H NMR (500 MHz, CDCl$_3$): d=7.38 (m, 5H, Harom); 5.77 (d, J=4 Hz, 1H, H—C(1')); 4.78 and 4.57 (2 d, J=12 Hz, 2H, Hbenzyl); 4.58 (dd, J=4, 4 Hz, 1H, H—C(2')); 3.99 (dd, J=9, 3 Hz, 1H, H—C(4')); 3.83 (dd, J=9, 4 Hz, 1H, H—C(3')); 3.47 (dq, J=7, 3 Hz, H—C(5')); 1.60 (s, 3H, CH$_3$); 1.44 (d, J=7 Hz, 3H, H—C(6')); 1.38 (s, 3H, CH$_3$) MS(EI): 320 (M+H$^+$)

(g) A solution of 5.0 g of compound no. 58 (15.7 mmol) in 25 ml CH$_2$Cl$_2$ at 0° C. is treated with 2.9 ml H$_2$O and 5.8 ml CF$_3$COOH. The reaction mixture is stirred for 9.0 h at 25° C., cooled to 0° C. and carefully treated with solid NaHCO$_3$. The reaction mixture is stirred for 0.3 h, diluted with CH$_2$Cl$_2$ and washed with CH$_2$Cl$_2$. The aqueous phase is extracted with CH$_2$Cl$_2$ (2×), the combined organic layers are dried (Na$_2$SO$_4$) and concentrated to give compound no. 59 (4.4 g, 100%). A small fraction is purified by flash chromatography (silica, 3% methanol in CH$_2$Cl$_2$) for analysis.

(compound no. 59)

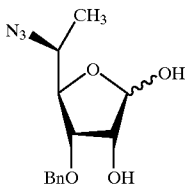

R$_f$=0.35, 0.27 (silica, 4% methanol in CH$_2$Cl$_2$)

(h) A solution of 4.4 g of crude compound no. 59 (15.8 mmol) in 50 ml pyridine is treated with 8.1 g of acetic acid anhydride (79.0 mmol) and 0.2 g of dimethylamino pyridine (1.6 mmol). The reaction mixture is stirred for 0.5 h at 25° C., poured into saturated, aqueous solution of NH$_4$Cl and extracted with CH$_2$Cl$_2$ (3×). The combined organic layers are dried (Na$_2$SO$_4$), concentrated and purified by flash chromatography (silica, 15–20% ethylacetate in hexane) to give compound no. 60 (4.7 g, 92%, mixture of anomers (3.5:1 by $^1$H NMR)).

(compound no. 60)

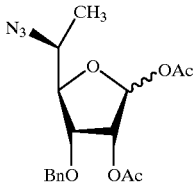

R$_f$=0.41, 0.31 (silica, 33% ethylacetate in hexane) $^1$H NMR of less polar, major anomer (500 MHz, CDCl$_3$): d=7.35 (m, 4H, Harom); 6.17 (s, 1H, H—C(1')); 5.34 (d, J=5 Hz, 1H, H—C(2')); 2.64 and 4.47 (2 d, J=11 Hz, 2H, Hbenzyl); 4.29 (dd, J=8, 5 Hz, 1H, H—C(3')); 4.01 (dd, J=8, 3 Hz, 1H, H—C(4')); 3.32 (dq, J=7, 3 Hz, 1H, H—C(5')); 2.14, 2.11 (2 s, 6H, OAc); 1.41 (d, J=7 Hz, 3H, H—C(6')) MS(FD): 363 (M)

(i) A solution of 4.1 g of compound no. 60 (12.0 mmol) and 2.1 g of thymine (16.8 mmol) in 40 ml CH$_3$CN is treated with 5.8 g of N,O-bis(trimethylsilyl)acetamid (28.4 mmol) and stirred for 0.5 h at 50° C. 5.7 g of trimethylsilyltrifluoromethane sulfonate (25.8 mmol) is added to the reaction mixture and stirring is continued for 3.0 h at 50° C. The reaction mixture is cooled to 25° C., poured into saturated, aqueous NaHCO$_3$ solution and extracted with CH$_2$Cl$_2$ (3×). The combined organic layers are dried (Na$_2$SO$_4$), concentrated and purified by flash chromatography (silica, 50% ethylacetate in hexane) to give compound no. 61 (4.42 g, 80%).

(compound no. 61)

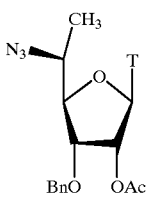

R$_f$=0.30 (silica, 50% ethylacetate in hexane) $^1$H NMR (250 MHz, CDCl$_3$): d=8.24 (bs, 1H, NH); 7.32 (m, 6H, Harom, H—C(6)); 5.94 (d, 1H, H—C(1')); 5.32 (dd, 1H, H—C(2')); 4.62 (d, 1H, Hbenzyl); 4.45 (d, 1H, Hbenzyl); 4.22 (dd, 1H, H—C(3')); 3.90 (dd, 1H, H—C(4')); 3.59 (dq, 1H, H—C(5')); 2.15 (s, 3H, OAc); 1.95 (s, 3H, CH$_3$); 1.42 (d, 3H, H—C(6'))

(j) A solution of 10.6 of compound no. 61 (24.6 mmol) in 70 ml dimethylformamide at 0° C. is treated with 7.5 g of 1,5-diazabicyclo-[5.4.0.]-undec-5-en (49.2 mmol) and a solution of 8.3 g of p-methoxybenzyloxymethylchloride (44.3 mmol) in 30 ml dimethylformamide. The reaction mixture is stirred for 2.0 h at RT, concentrated and purified by flash chromatography (30–50% ethylacetate in hexane) to give compound no. 62 (12.3 g, 87%).

(compound no. 62)

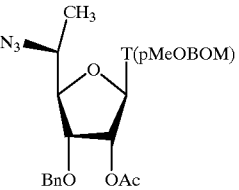

R$_f$=0.27 (silica, 33% ethylacetate in hexane). $^1$H NMR (250 MHz, CDCl$_3$): d=7.30 (m, 8H, Harom, H—C(6)); 6.88 (m, 2H, Harom); 5.92 (d, 1H, H—C(1')); 5.45 (2 d, AB 2H, NCH$_2$O); 5.38 (dd, 1H, H—C(2')); 4.68–4.40 (m, 4H, Hbenzyl); 4.20 (dd, 1H, H—C(3')); 3.89 (dd, 1H, H—C(4')); 3.79 (s, 3H, OCH$_3$); 3.60 (dq, 1h, H—C(5')); 2.15 (s, 3H, OAc); 1.95 (s, 3H, CH$_3$); 1.42 (d, 3H, H—C(6')).

(k) A solution of 12.3 g of compound no. 62 (21.3 mmol) in 120 ml methanol at 0° C. is treated with 4.6 g of sodium methanolate (85.2 mmol) and stirred for 1.0 h at 0° C. The reaction mixture is poured into aqueous, saturated NH$_4$Cl-solution, extracted with CH$_2$Cl$_2$ (3×), dried (Na$_2$SO$_4$), adsorbed on silica gel and purified by flash chromatography (50% ethylacetate in hexane) to give compound no. 63 (10.8 g, 94%).

(compound no. 63)

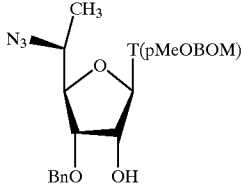

$R_f$=0.31 (silica, 50% ethylacetate in hexane) $^1$H NMR (500 MHz, CDCl$_3$): d=7.43–7.28 (m, 7H, Harom); 7.24 (d, J=1 Hz, 1H, H—C(6)); 6.86 (m, 2H, Harom); 5.77 (d, J=4 Hz, 1H, H—C(1')); 5.46 (dd, J=9 Hz, 2H, NCH$_2$O); 4.64 (dd, J=11 Hz, 2H, Hbenzyl); 4.62 (s, 2H, Hbenzyl); 4.26 (m, 1H, H—C(2')); 4.13 (m, 1H, H—C(3')); 3.93 (dd, J=6, 4 Hz, 1H, H—C(4')); 3.80 (s, 3H, OCH$_3$); 3.58 (dq, J=7, 4 Hz, 1H, H—C(5')); 2.91 (d, J=6 Hz, OH); 1.94 (d, J=1 Hz, 3H, CH$_3$); 1.40 (d, J=7 Hz, 3H, H—C(6')) MS(CI): 555 (M+NH$_4^+$), 538 (M+H$^+$)

(l) To a solution of 10.3 g of compound no. 63 (19.1 mmol) in 100 ml tetrahydrofuran at 0° C. 2.3 g of NaH (57.3 mmol) are added and the reaction mixture is stirred for 0.5 h at 0° C. Methyl iodide is added to the reaction mixture and stirring is continued for 1.0 h at 0° C. The reaction mixture is poured into aqueous, saturated NH$_4$Cl-solution, extracted with CH$_2$Cl$_2$ (3×), the combined organic layers are dried (Na$_2$SO$_4$), concentrated and purified by flash chromatography (30% ethylacetate in hexane) to give compound no. 64 (10.8 g, 100%).

(compound no. 64)

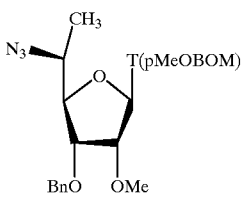

$R_f$=0.43 (silica, 50% ethylacetate in hexane) $^1$H NMR (500 MHz, CDCl$_3$): d=7.50 (d, J=1 Hz, 1H, H—C(6)); 7.40–7.30 (m, 7H, Harom); 6.87 (m, 2H, Harom); 5.90 (d, J=2 Hz, 1H, H—C(1')); 5.46 (2 d, J=9 Hz, 2H NCH$_2$O); 4.64 (s, 2H, Hbenzyl); 4.61 (2d, AB, J=11 Hz, 2H, Hbenzyl)); 4.03 (dd, J=8, 2 Hz, 1, H—C(4')); 3.92 (dd, J=8, 5 Hz, 1H, H—C(3')); 3.79 (s, 3H, ArOCH$_3$); 3.8 (1H, H—C(5')); 3.78 (dd, J=5, 2 Hz, 1H, H—C(2')); 1.94 (d, J=1 Hz, 3H, CH$_3$); 1.47 (d, J=7 Hz, 3H, H—C(6')).

(m) 0.983 g of SnCl$_2$.H$_2$O is added to a solution of 2.0 g of compound no. 64 (3.63 mmol) in 3 ml methanol at 0° C. and the mixture is stirred for 16.0 h at RT. The reaction mixture is poured into saturated, aqueous NaHCO$_3$-solution and extracted with CH$_2$Cl$_2$ (3×). The combined organic layers are dried (Na$_2$SO$_4$), concentrated and purified by flash chromatography (5% methanol in CH$_2$Cl$_2$) to give compound no. 65 (1.4 g, 71%).

(compound no. 65)

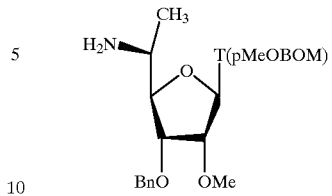

$R_f$=0.27 (silica, 7% methanol in CH$_2$Cl$_2$) $^1$H NMR (500 MHz, CDCl$_3$): d=7.66 (d, J=1 Hz, 1H, H—C(6)); 7.40–7.30 (m, 7H, Harom); 6.86 (m, 2H, Harom); 5.85 (d, J=2 Hz, 1H, H—C(1')); 5.47 (2d, J=9 Hz, 2H, NCH$_2$O); 4.68, 4.55 (2d, J=11 Hz, 2H, Hbenzyl); 4.64 (s, 2H, Hbenzyl); 3.97–3.87 (m, 3H, H—C(2',3',4'); 3.80 (s, 3H, ArOCH$_3$); 3.54 (s, 3H, OCH$_3$); 3.10 (bs. 1H, H—C(5')); 1.91 (d, J=1 Hz, 3H, CH$_3$); 1.22 (d, J=7 Hz, H—C(6')). MS(CI): 526 (M+H$^+$)

(n) A solution of 1.42 g of carboxylic acid compound no. 66 (2.5 mmol, dried over P$_2$O$_5$ on HV, 16.0 h)

(compound no. 66)

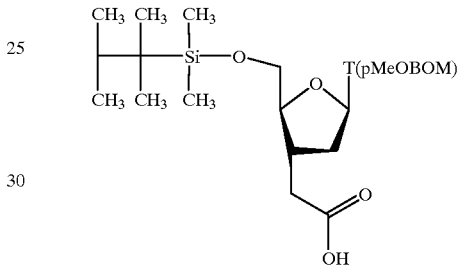

in 12 ml CH$_3$CN is treated with 273 mg of triethylamine (2.7 mmol), 867 mg of O-(1-benztriazol-1-yl)-N,N,N,N-tetramethyluroniumtetrafluoroborat (2.7 mmol) and 166 mg of hydroxybenztriazol (1.3 mmol). The reaction mixture is stirred for 1.5 h. A solution of 1.31 g of amine compound no. 65 (2.5 mmol, dried over P$_2$O$_5$ on HV, 16 h) in 15 ml CH$_3$CN and 373 mg of triethylamine (3.6 mmol) are added to the reaction mixture and stirring is continued for 24 h. The reaction mixture is poured into aqueous, saturated NaH$_2$PO$_4$-solution, a saturated solution of sodium chloride in water, dried (Na$_2$SO$_4$), concentrated and purified by flash chromatography to give compound no. 67 (2,20 g, 85%).

(compound no. 67)

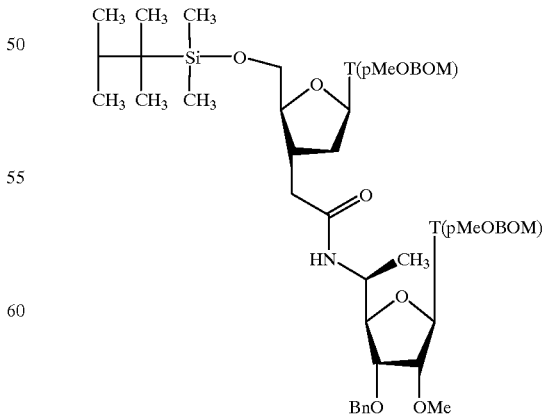

$R_f$=0.61 (silica, 5% methanol in CH$_2$Cl$_2$) $^1$H NMR (500 MHz, CDCl$_3$): d=7.52 (d, J=1 Hz, 1H, H—C(6)); 7.39–7.22

(m, 9H, Harom); 6.83 (m, 4H, Harom); 7.05 (d, J=1Hz, 1H, H—C(6)); 6.13 (dd, J=6, 6 Hz, 1H, H—C(1'A)); 5.49 (dd, J=10 Hz, 2H, NCH₂O); 5.41 (dd, J=10 Hz, 2H, NCH₂O); 5.17 (d, J=4 Hz, 1H, H—C(1'B); 4.60 (m, 6H, Hbenzyl); 4.32 (dd, J=6, 4 Hz, 1H, H—C(2'B)); 4.27 (m, 1H, H—C(5'B)); 4.11 (dd, J=6, 6 Hz, 1H, H—C(3'B)); 4.01 (dd, J=6, 2 Hz, 1H, H—C(4'B)); 3.90 (dd, J=13, 3 Hz, H—C(5'A)); 3.78 (2s, 6H, ArOCH₃); 3.66 (m, 1H, H—C(4'A,5'A)); 3.42 (s, 3H, OCH₃); 2.72 (m, 1H, H—C(3'A)); 2.4–2.10 (m, 4H, H—C(6'A,2'A)); 1.95 (2 d, J=1 Hz, 6H, CH₃); 1.65 (hept, J=6 Hz, 1H, Me₂CH); 1.22 (d, J=6 Hz, 3H, H—C(6'B)); 0.88 (m, 12H, CH₃); 0.18 (2 s, 6H, Si(CH₃)₂) MS(EI): 1082 (M—H⁺)

(o) To a solution of 2.20 g of compound no. 67 (2.03 mmol) in 30 ml CH₂Cl₂ and 3 ml H₂O 1.89 g of 1,2-dichloro-4,5-dicyano-3,6-quinone (8.67 mmol) are added in portions during 2 h and the reaction mixture is stirred for additional 0.5 h. The reaction mixture is filtered through celite, concentrated and purified by flash chromatography (3–20% methanol in CH₂Cl₂) to give compound no. 68 (1.34 g, 84%).

(compound no. 68)

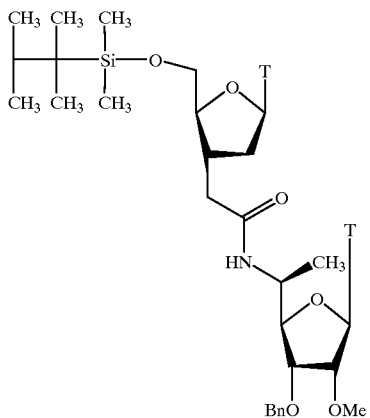

$R_f$=0.15 (silica, 2.5% methanol in CH₂Cl₂) ¹H NMR (500 MHz, CDCl₃): d=8.97 (bs, 1H, NH); 8.14 (bs, 1H, NH); 8.14 (bs, 1H, NH); 7.52 (d, J=1 Hz, H—C(6)); 7.38–7.23 (m, 4h, Harom); 7.02 (d, J=1 H, H—C(6)); 6.23 (dd, J=6, 6 Hz, 1H, H—C(1'A)); 5.12 (d, J=4 Hz, H—C(1'B)); 4.63 (2d, J=11 Hz, 2H, Hbenzyl); 4.30 (m, 2H, H—C(2'B,5'B)); 4.09 (dd, J=6, 6 Hz, 1H, H—C(3'B)); 4.01 (dd, J=6, 2 Hz, 1H, H—C(4'B)); 3.91 (dd, J=11, 2 Hz, 1H, H—C(5'A)); 3.80 (ddd, J=5, 2, 2 Hz, 1H, H—C(4'A)); 3.74 (dd, J=11, 3 Hz, 1H, H—C(5'A)); 3.42 (s, 3H, OCH₃); 2.85 (m, 1H, H—C(3'A)); 2.43 (dd, J=14, 5 Hz, 1H, H—C(6'A)); 2.25 (dd, J=14, 10 Hz, 1H, H—C(6'A)), 2.13 (m, 2H, H—C(2'A)); 1.96, 194 (2 d, J=1 Hz, 6H, CH₃); 1.66 (m, 1H, Me₂CH); 1.20 (d, J=7 Hz, H—C(6'B)); 0.90 (m, 4H, CH₃); 0.18 (s, 6H, CH₃) MS(CI): 801 (M+NH₄⁺), 784 (M+H⁺)

(p) A solution of 650 mg of compound no. 68 (0.83 mmol) in 6 ml tetrahydrofuran is treated with 1.25 ml n-tetrabutylammonium fluoride (1.0 M solution in tetrahydrofuran, 1.25 mmol) and stirred at 25° C. for 24.0 h. The mixture is poured into aqueous, saturated NaHCO₃ solution, extracted with CH₂Cl₂ (3×), dried (Na₂SO₄), concentrated and purified by flash chromatography (2–7% methanol in CH₂Cl₂) to give compound no. 69 (505 mg, 95%).

(compound no. 69)

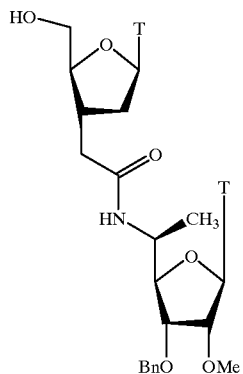

$R_f$=0.21 (silica, 6.5% methanol in CH₂Cl₂) ¹H NMR (500 MHz, CDCl₃): d=9.83 (bs, 1H, NH); 9.21 (bs, 1H, NH); 7.85 (s, 1H, H—C(6)); 7.28 (m, 5H, Harom); 7.02 (s, 1H, H—C(6)); 6.08 (dd, 1H, H—C(1'A)); 5.15 (d, J=5 Hz, 1H, H—C(1'B)); 4.65, 4.59 (2d, J=11 Hz, 2H, Hbenzyl); 4.36 (dd, J=5, 5 Hz, 1H, H—C(2'B)); 4.25 (m, 1H, H—C(5'B)); 4.05 (m, 2H, H—C(3'B,4'B)); 3.98 (m, 1H, H—C(5'A)); 3.74 (m, 2H, H—C(4'B,3' B)); 3.41 (s, 3H, OCH₃); 3.37 (m, 1H, H—C(5'A)); 2.80 (m, 1H, H—C(3'A)); 2.49 (dd, J=15, 6 Hz, 1H, H—C(6'A)); 2.34 (dd, J=15, 8 Hz, 1H, H—C(6'A)); 2.21 (m, 2H, H—C(2'A)); 2.94 (2 s, 6H, CH₃); 1.20 (d, J=8 Hz, 3H, H—C(6'B)) MS(EI): 642 (M+H⁺)

(q) A solution of 310 mg of compound no. 69 (0.48 mmol) is degassed with argon, treated with Pd/C (10%, 62 mg) and stirred under an H₂-atmosphere for 1.5 h. The reaction vessel is flushed with argon, filtered through celite and concentrated to give compound no. 70 (267 mg, 92%).

(compound no. 70)

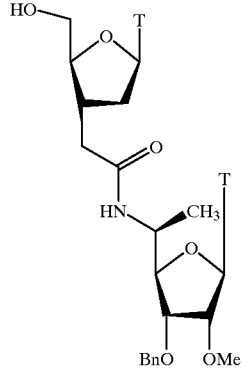

$R_f$=0.17 (silica, 10% methanol in CH₂Cl₂) ¹H NMR (250 MHz, CD₃OD): d=7.90 (s, 1H, H—C(6)); 7.45 (s, 1H, H—C(6)); 5.95 (dd, 1H, H—C(1'A)); 5.60 (d, 1H, H—C(1=B)); 3.38 (s, 3H, OCH₃); 1.19 (d, 3H, H—C(6'B)).

(r) A solution of 186 mg of compound no. 70 (0.34 mmol) in 2 ml pyridine is treated with 3 Å molecular sieves (200 mg), 171 mg of 4,4'-dimethoxytriphenylchloride (0.51 mmol) and 102 mg of triethylamine (1.01 mmol) and stirred for 2.0 h at 25° C. The reaction mixture is poured into an aqueous, saturated NaHCO₃-solution, extracted with CH₂Cl₂ (3×), dried (Na₂SO₄), concentrated, coevaporated with toluene (2×) and purified by flash chromatography (5% methanol in CH₂Cl₂, 1% triethylamine) to give compound no. 71 (274 mg, 95%).

$R_f$=0.20 (silica, 12.5% methanol in CH₂Cl₂) ¹H NMR (500 MHz, CDCl₃): d=7.63 (d, J=1 Hz, 1H, H—C(6)); 7.44 (m, 2H, Harom); 7.34–7.20 (m, 7H, Harom); 7.06 (d, J=1 Hz, 1H, H—C(6)); 6.86 (m, 4H, Harom); 6.27 (dd, J=6, 6 Hz, 1H, H—C(1'A)); 5.12 (d, J=4 Hz, 1H, H—C(1'B)); 5.43 (m, 3H, H—C(2'B,3'B,5'B)); 3.84 (m, 2H, H—C(4'A,4═B)); 3.79 (s, 6H, ArOCH₃); 3.50 (s, 3H, OCH₃); 3.46 (dd, J=11, 2 Hz, 1H, H—C(5'A)); 3.29 (dd, J=11, 3 Hz, 1H, H—C(5'A)); 2.79 (m, 1H, H—C(3'A)); 2.73 (bs, 1H, OH); 2.39 (m, 2H, H—C(2'A,6'A)); 2.23 (m, 2H, H—C(2'A,6'A)); 1.94 (d, J=1 Hz, 3H, CH₃); 1.41 (d, J=1 Hz, 3H, CH₃); 1.16 (d, J=7 Hz, 3H, H—C(6'B)) MS(CI): 853 (M⁻)

EXAMPLE A6

Preparation of Compound No. 80

(compound no. 80)

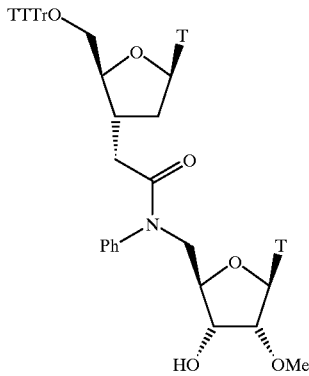

(a) 5.46 g of 2'-α-methoxy-thymidine and 9.86 g of tris-t-butyl-trityl chloride are added to 60 ml dry pyridine. 2.23 g of triethylamine are added to this suspension. After 96 h at RT the reaction mixture is evaporated to dryness and the residue is dissolved in toluene. After evaporation the oily residue is taken up in ether and washed twice with a saturated solution of sodium chloride in water. The organic phase is dried over Na₂SO₄ and evaporated to dryness. The residue is taken up in hexane, the product crystallizes out and is filtered off. Yield 12.66 g (92%) of compound no. 72.

(compound no. 72)

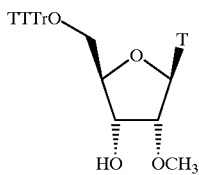

¹H-NMR (CDCl₃, 500 Mhz, J (Hz)): 3.65 (s, 3H, OCH₃).

12.62 g of compound no. 72 and 2.77 g of imidazole are dissolved in 20 ml dry dimethylformamide. 5.59 g of t-butyl-diphenyl chlorosilane are added dropwise over a period of 5 min. After 3.5 h the suspension is diluted with ether and washed three times with water. The organic phase is dried over Na₂SO₄ and evaporated. After treatment with hexane and filtering: yield 12.87 g (76%) of compound no. 73 as white crystals.

(compound no. 73)

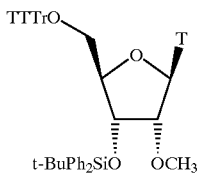

¹H-NMR (CDCl₃, 500 Mhz, J (Hz)): 3.25 (s, 3H, OCH₃); 0.98 (s, 9H, t-Bu)

(c) 16.74 g of compound no. 73 are dissolved in 360 ml 80% aqueous acetic acid and heated up to 60° C. After 1 h the reaction mixture is evaporated to dryness and the residue is chromatographed on silica gel with a gradient of CH₂Cl₂/methanol (100% to 95%/5%) to yield 8.27 g of compound no. 74.

(compound no. 74)

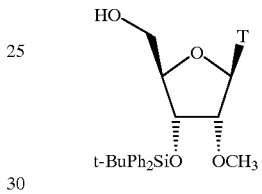

¹H-NMR (CDCl₃, 500 Mhz, J (Hz)): 3.36 (s, 3H, OCH₃); 1.10 (s, 9H, t-Bu).

(d) 8.0 g of compound no. 74 are dissolved in 80 ml of a 1:1 mixture of pyridine and CH₂Cl₂. 3.58 g of tosyl chloride are added portionwise and the solution is stirred over night. Another 2.99 g of TsCl are added and the reaction mixture is stirred for an additional 48 h. After removal of the solvents the residue is taken up in CH₂Cl₂ and washed with water. After evaporation chromatographic purification of the residue affords 9.0 g of compound no. 75. The thin layer chromatography pure compound consists of a mixture of the tosylate and the corresponding chloride. The mixture is used as such in the next step.

(compound no. 75)

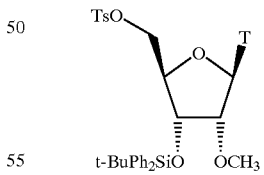

(e) 9.0 g of the mixture obtained in A6(d) above are suspended in 12.35 ml aniline and 75 mg of tetrabutyl ammonium iodide are added. This mixture is heated to 100° C. in a sealed tube for 12 h. Aniline is distilled off in vacuo and the residue is taken up in CH₂Cl₂ and washed with water. After drying and evaporation of the solvent, 8.39 g of the residue are chromatographed over silica gel using toluene/ethyl acetate as eluent to yield 6.8 g of compound no. 76.

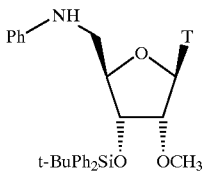
(compound no. 76)

¹H-NMR (CDCl₃, 500 Mhz, J (Hz)): 3.53 (s, 3H, OCH₃); 1.14 (s, 9H, t-Bu)

(f) 360 mg of acid compound no. 77

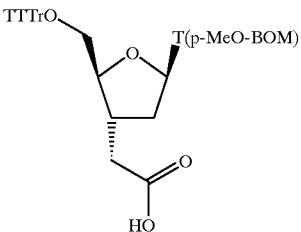
(compound no. 77)

prepared according to De Mesmaeker, A., Waldner, A., Lebreton, J., Hoffmann, P., Fritsch, V., Wolf, R. M., Freier, S. M., Angew. Chem. Int. Ed. Engl. 33: 226–229 (1994), 250 mg of aniline compound no. 76 and 165 mg of 2-chloro-N-methylpyridinium jodide are dissolved in dry CH₃CN. 130 mg of triethylamine are added to this mixture and the resulting solution is heated under reflux for 4 h. The crude reaction mixture is chromatographed after evaporation using a gradient of toluene/ethyl acetate 8:2 to 1:1 yielding 290 mg of compound no. 78.

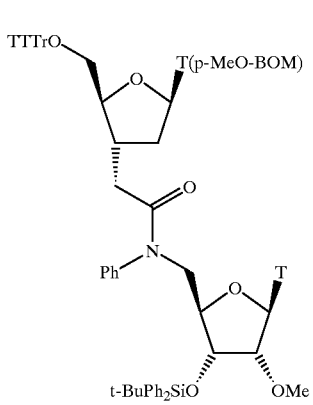
(compound no. 78)

¹H-NMR (CDCl₃, 500 Mhz, J (Hz)): 130 (s,27H, 3 t-Bu); 5.45(2d, J=8, CH₂Ph). MS (FD): 1261.

(g) 1.46 g of compound no. 78 are dissolved in 20 ml CH₂Cl₂/H₂O (20:1). 0.94 g of 1,2-dichloro-4,5-dicyano-3,6-quinone are added within 1 min. After 90 min the solution is filtered and the filtrate washed with saturated Na₂S₂O₅. After drying and evaporation chromatographic purification of the residue affords 0.84 g of compound no. 79.

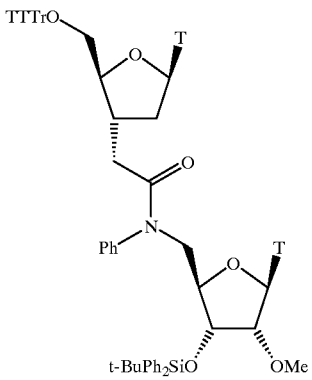
(compound no. 79)

¹H-NMR (CDCl₃, 500 Mhz, J (Hz)): 3.34 (s, 3H, OCH₃); 1.03 (s, 9H, t-Bu). MS (FD): 1261

(h) 0.84 g of compound no. 79 are treated with a mixture of tetrabutyl ammonium fluoride and acetic acid (1:1; 4 equivalents) in tetrahydrofuran. After 2 h the reaction is complete. After evaporation the chromatographic purification affords 0.65 g of compound no. 80.

¹H-NMR (CDCl₃, 500 Mhz, J (Hz)): 3.58 (s, 3H, OCH₃). MS (FD): 1023.

EXAMPLE A7

Preparation of compound no. 96

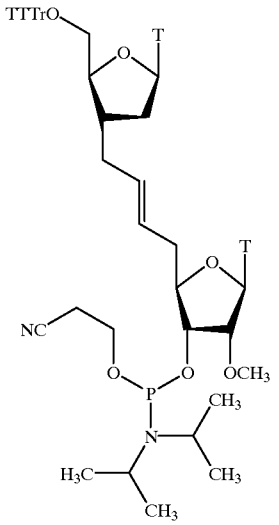
(compound no. 96)

(a) 14.2 g of aldehyde compound no. 81 (28.0 mmol)

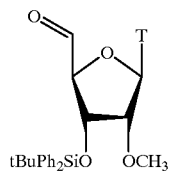
(compound no. 81)

are dissolved in 100 ml CH₂Cl₂ and cooled to 0° C. 11.2 g of (methoxycarbonylmethylene)-triphenylphosphoran (33.5 mmol) are added in portions and the reaction mixture is stirred for 1.5 h at 0° C. The mixture is washed with water and the aqueous phase is extracted with CH$_2$Cl$_2$. The combined organic phases are dried (Na$_2$SO$_4$), concentrated and purified by flash chromatography to give olefin compound no. 82.

(compound no. 82)

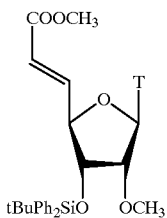

(b) 14.7 g of olefin compound no. 82 (26.1 mmol) are dissolved in 200 ml methanol and degassed with argon. 1.4 g of 10% Pd/C are added and hydrogen gas is bubbled through the reaction mixture for 10 min. The reaction mixture is rapidly stirred for 20 h under hydrogen atmosphere (1 atm). The hydrogen atmosphere is replaced with an argon atmosphere, the reaction mixture is filtered through Celite, concentrated and coevaporated with benzene (2×) to give compound no. 83.

(compound no. 83)

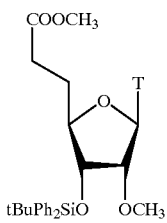

(c) 14.7 g of compound no. 83 (26.1 mmol) are dissolved in 70 ml dimethylformamide and cooled to 0° C. 8.0 g of diazabicycloundecen (52.1 mmol) and a solution of 7.8 g of p-methoxybenzyloxymethylchloride (41.8 mmol) in 15 ml dimethylformamide are added to the reaction mixture. The reaction mixture is stirred at 25° C. for 25 h, concentrated, coevaporated with toluene (2×) and purified by flash chromatography to give compound no. 84.

(compound no. 84)

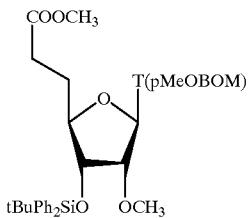

(d) 15.3 of methyl ester compound no. 84 (21.4 mmol) are dissolved in 500 ml tetrahydrofuran, cooled to 0° C. and treated with 320 ml of an aqueous 0.2M NaOH-solution. The reaction mixture is stirred for 3.0 h at RT, diluted with Ch$_2$Cl$_2$ and washed with saturated aqueous NaH$_2$PO$_4$-solution. The aqueous phase is further extracted with CH$_2$Cl$_2$ (3×), the combined organic layers are dried (Na$_2$SO$_4$) and purified by flash chromatography to give carboxylic acid compound no. 85.

(compound no. 85)

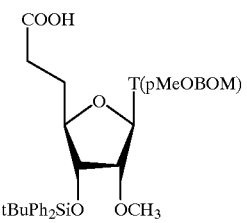

(e) 8.0 g of carboxylic acid compound no. 85 (11.4 mmol) are dissolved in 60 ml 1,2-dichloroethane, cooled to 0° C., and treated with 1.7 g of 1-chloro-N,N,2-trimethyl-propenylamine (12.5 mmol). After 1.0 h at 0° C. 1.8 g of 2-mercaptopyridine-N-oxide sodium-salt (12.5 mmol) are added as a solid and the reaction mixture is stirred at 0° C. for 1.0 h in the dark. The reaction mixture is diluted with 290 ml 1,2-dichloroethane and degassed with argon. 22.8 g of bromotrichlormethane (114.0 mmol) are added to the reaction mixture and the reaction is irradiated with a sun lamp for 5 min. The reaction mixture is concentrated and purified by flash chromatography to give compound no. 86.

(compound no. 86)

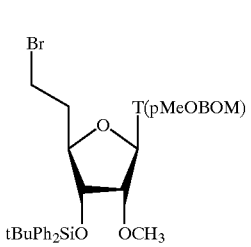

(f) 4.2 g of bromide compound no. 86 (5.7 mmol), 1.8 g of NaI (11.4 mmol) and 3.0 g of triphenylphosphine (11.4 mmol) are dissolved in CH$_3$CN and stirred at 65° C. for 36 h. The reaction mixture is concentrated and purified by flash chromatography to give compound no. 87.

(compound no. 87)

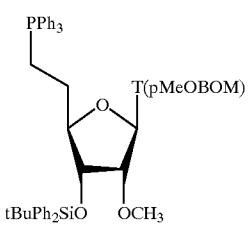

(g) 2.3 g of compound no. 87 (2.45 mmol) are dissolved in 20 ml tetrahydrofuran and cooled to −78° C. 2.7 ml (TMS)$_2$NNa (1M solution in tetrahydrofuran, 2.7 mmol) is added to the reaction mixture. After 1 min 1.37 g of aldehyde compound no. 88 (2.45 mmol)

(compound no. 88)

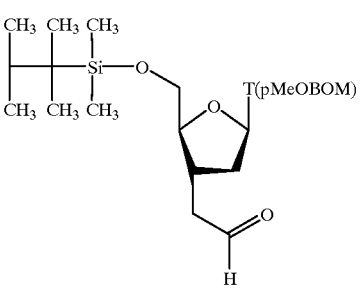

dissolved in 7 ml tetrahydrofuran is added to the reaction mixture and stirring is continued for 1.0 h at −78° C. The reaction is stopped with water and stirred for 0.3 h, diluted with ethylacetate and washed with saturated aqueous NaCl-solution. The aqueous phase is extracted with ethylacetate (2×), the combined organic layers are dried (Na₂SO₄), concentrated and purified by flash chromatography to give compound no. 89.

(compound no. 89)

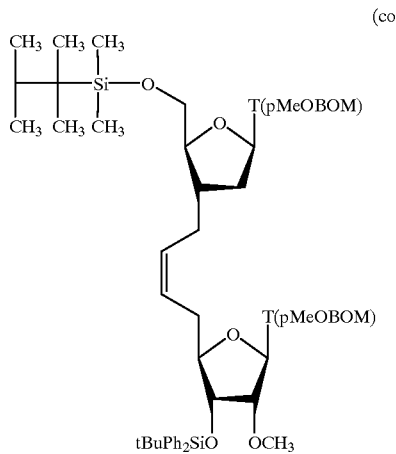

(h) 2.20 g of compound no. 89 (1.83 mmol) are dissolved in 10 ml CH₂Cl₂/H₂O (20:1). 2.9 g of 1,2-dichloro-4,5-dicyano-3,6-quinone (12.4 mmol) are added in portions and the reaction mixture is stirred for 3.0 h. The reaction mixture is filtered through celite, concentrated and purified by flash chromatography to give compound no. 90.

(compound no. 90)

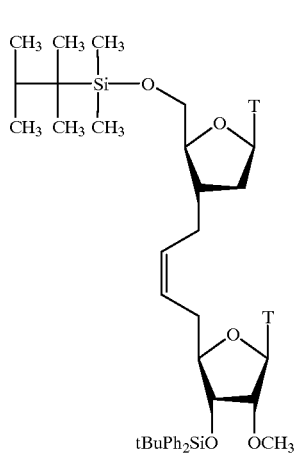

(i) 1.50 g of compound no. 90 (1.67 mmol) are dissolved in 15 ml degassed benzene, treated with 91 mg of thiophenol (0.83 mmol) and 41 mg of azoisobutyronitrile (0.25 mmol) and stirred at 80° C. Additional 91 mg of thiophenol (0.83 mmol) and 41 mg of azoisobutyronitrile (0.25 mmol) are added (5× in 4 h intervals). The reaction mixture is concentrated and purified by flash chromatography to give compound no. 91 (mixture of trans and cis isomers).

(compound no. 91)

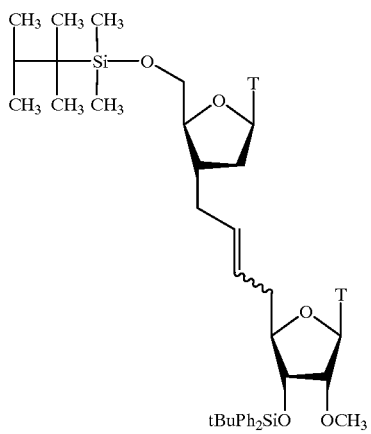

(j) 1.20 g of compound no. 91 (1.33 mmol) are dissolved in 15 ml tetrahydrofuran, treated with n-tetrabutylammonium fluoride (3.1 ml of 1M solution in tetrahydrofuran, 3.1 mmol), stirred for 16.0 h at 25° C., concentrated and purified by flash chromatography to give diol compound no. 92 (mixture of trans and cis isomers).

(Compound no. 92)

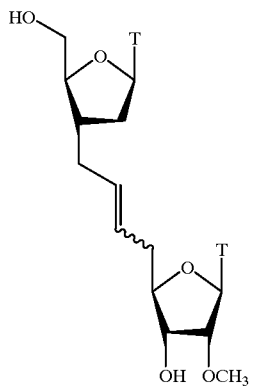

(k) A solution of 600 mg of diol compound no. 92 (1.15 mmol) in 5 ml pyridine is treated with 349 mg of triethylamine (3.45 mmol) and 750 mg of tris(tert-butyl)-trityl-chloride (1.73 mmol). The reaction mixture is stirred at 60° C. After 3.0 h and 6.0 h additional tris)tert-butyl)-trityl-chloride (240 mg, 0.86 mmol and 131 mg, 0.42 mmol) is added to the reaction mixture. After 7 h the reaction mixture is concentrated, coevaporated with toluene (3×) and purified by flash chromatography to give compound no. 93 (mixture of trans and cis isomers).

(Compound no. 93)

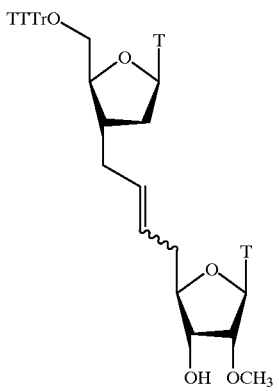

(l) A solution of 950 mg of compound no. 93 (1.02 mmol) in 4 ml dimethylformamide at 0° C. is treated with 620 mg of diazabicycloundecen (4.10 mmol) and a solution of 570 mg of p-methoxybenzyloxymethylchloride (3.06 mmol) is added. The reaction mixture is stirred for 3.5 h at 25° C., diluted with $CH_2Cl_2$, washed with an aqueous solution of $NaHCO_3$ and the aqueous phase is extracted with $CH_2Cl_2$ (2×). The combined organic layers are dried ($Na_2SO_4$), concentrated and coevaporated with toluene (2×). The crude product is purified by flash chromatography to give a mixture of trans and cis isomers.

The trans-isomer is separated form the cis-isomer by flash chromatography ($AgNO_3$ impregnated $SiO_2$). After repeated chromatography compound no. 94 (pure trans-isomer) is obtained.

(Compound no. 94)

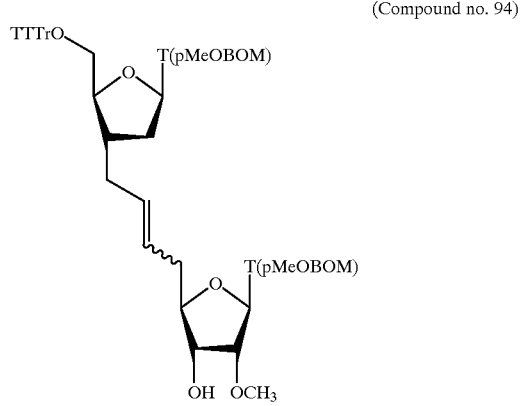

(m) 340 mg of compound no. 94 (0.276 mmol) are dissolved in 2.8 ml ($CH_2Cl_2$ and treated with 0.2 ml water and 626 mg of 1,2-dichloro-4,5-dicyano-3,6-quinone (2.76 mmol). The reaction mixture is stirred for 0.7 h at 25° C., neutralized with 25 drops saturated aqueous $Na_2CO_3$ solution, filtered through celite, concentrated and purified by flash chromatography to give compound no. 95.

(Compound no. 95)

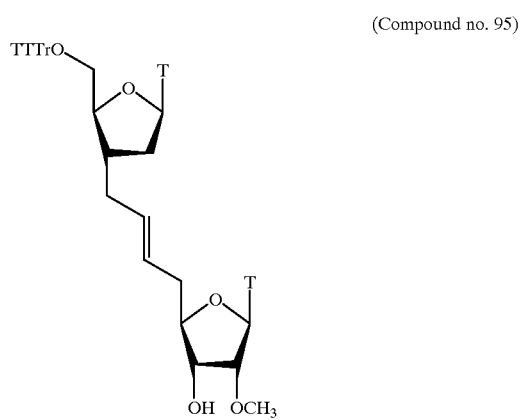

(n) 118 mg of alcohol compound no. 95 (0.127 mmol) and 108.7 mg of di-isopropylammonium tetrazolide (0.635 mmol) are dried for 2 h (HV, 60° C.), dissolved in 4 ml $CH_2Cl_2$ and treated with 114.6 mg of cyanoethoxy-bis-diisopropylamino-phosphine (0.381 mmol). The reaction mixture is stirred for 1.5 h at 25° C. The reaction is concentrated, dissolved in $CH_2Cl_2$ and precipitated in cold pentane. The mother liquor is concentrated and remaining product is precipitated. The precipitates are washed with pentane and purified by flash chromatography to give phosphoramidite compound no. 96 (mixture of diastereomers).

EXAMPLE A8

Preparation of compound no. 99

(Compound no. 99)

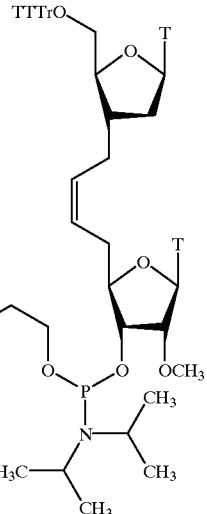

(a) A solution of 620 mg of compound no. 90 (0.689 mmol) in 3 ml tetrahydrofuran is treated with a solution of n-tetrabutylammonium fluoride in tetrahydrofuran (1M, 1.59 ml, 1.59 mmol). The reaction mixture is stirred for 2.0 h at 50° C., concentrated and purified by flash chromatography to give diol compound no. 97.

(Compound no. 97)

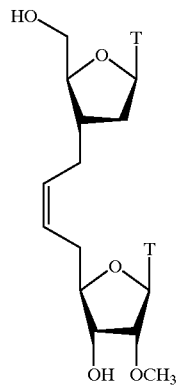

(b) 340 mg of diol compound no. 97 (0.654 mmol) and 439 mg of tris(tert-butyl)-trityl-chloride (0.982 mmol) are dried for 4 h (HV, 60° C.), dissolved in 2 ml pyridine and treated with 200 mg of triethylamine (1.96 mmol). The reaction mixture is stirred at 50° C. for 2.0 h. Additional 440 mg of tris(tert-butyl)-trityl-chloride (0.982 mmol is added, the reaction mixture is stirred for another 16 h at 50° C., concentrated, coevaporated with toluene (2×) and purified by flash chromatography to give compound no. 98.

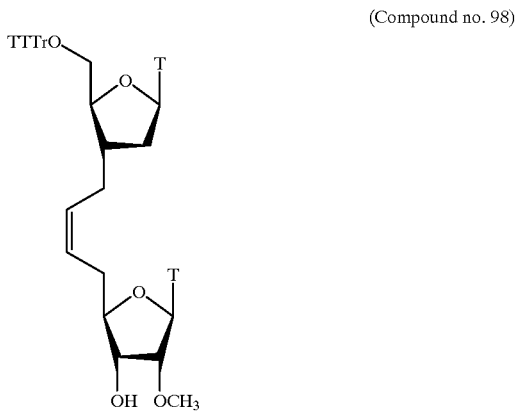

(Compound no. 98)

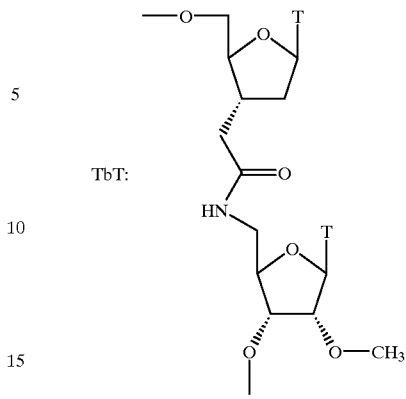

TbT:

(c) 176 mg of alcohol compound no. 98 (0.189 mmol) and 162 mg of di-isopropyl-ammonium tetrazolide (0.950 mmol) are dried for 2 h (HV, 60° C.), dissolved in 4 ml $CH_2Cl_2$ and treated with 171 mg of cyanoethoxy-bis-diisopropylamino-phosphine (0.567 mmol). The reaction mixture is stirred for 1.5 h at 25° C., concentrated and purified by flash chromatography. The product containing fractions are dissolved in $CH_2Cl_2$ and precipitated in cold pentane. The mother liquor is concentrated and remaining product is precipitated. The precipitates are washed with pentane to give phosphoramidite compound no. 99 (mixture of diastereomers).

B. Synthesis of oligonucleotides

Each oligonucleotide is prepared on an ABI 390 DNA synthesizer using standard phosphoramidite chemistry according to Gait, M. J., Oligonucleotide Synthesis: A Practical Approach IRL Press, Oxford (1984) but with prolonged coupling times (10 min). Dimethoxytrityl oligonucleotides are purified by reverse phase HPLC (column: Nucleosil $RPC_{18}$, 10 μ, 10×250 mm; eluent A: 50 mM triethylammonium acetate (TEAA), pH 7.0; eluent B: 50 mM TEAA, pH 7.0% acetonitrile; elution with gradient from 15% to 45% B in 45 min). After purification by HPLC the oligodeoxynucleotides are controlled by capillary gel electrophoresis (concentration: 1 OD/ml, injection: 2 kV, 3 sec, separation: 9 kV, capillary: effective length 30 cm, inner diameter 100 μm, polyacrylamide 10% T, buffer: 100 mM $H_3PO_4$, 100 mM Tris, 2 mM EDTA, 7M urea pH 8.8). The molecular weight of each oligodeoxynucleotide is checked by mass spectroscopy [MALDI-TOF: Pieles, U., Zürcher, W., Schär, M., Moser, H., Nucl. Acids Res. 21:3191 (1993)]. The oligodeoxynucleotide is desorbed using 2,4,6-trihydroxyacetophenone as a matrix (detection of negatively charged ions) with diammonium hydrogen citrate as additive (25 mM final concentration).

Oligonucleotides synthesized

Sequence 1: TpTpTpTbTpCpTpCpTpCpTpCpTpCpT (SEQ ID NO: 1)

Sequence 2: GpCpGpTbTpTbTpTbTpTbTpTbTpGpCpG (SEQ ID NO: 2)

Sequence 3: CpGpApCpTpApTpGpCpApTbTpTbTpC (SEQ ID NO: 3)

MALDI-TOF M.S. analysis of sequence 1:
calculate: 4416.038 experimental: 44169

C. Properties of oligonucleotides

EXAMPLE C1

Melting points

The thermal denaturation ($T_m$) of DNA/RNA hybrides is performed at 260 nm using a Gilford Response II Spectrophotometer (Ciba-Corning Diagnostics Corp., Oberlin, Ohio). Absorbance versus temperature profiles are measured at 4 μM of each strand in 10 mM phosphate pH 7.0 (Na salts), 100 mM total [$Na^+$] (supplemented as NaCl), 0.1 mM EDTA. $T_m$'s are obtained from fits of absorbance versus temperature curves to a two-state model with linear slope baselines [Freier, S. M., Albergo, D. D., Turner, D. H., Biopolymers 22:1107–1131 (1982)]. All values are averages of at least three experiments. The absolute experimental error of the $T_m$ values is ±0.5° C.

$T_m$ °C.) of the duplex with sequence 1 and the complementary RNA strand: $T_m$=54.2° C. for the wild type (duplex with DNA sequence 1): $T_m$=52.2° C. $\Delta T_m$/1 modification=+2.1° C.

EXAMPLE C2

Resistence against 3'-Exonucleases

For experimental details see Hoke, G. D., Draper, K., Freier, S. M., Gonzales, C., Driver, V. B., Zounes, M. C., Ecker, D. J., Nucl. Acids Res. 19:5743 (1991).

EXAMPLE C3

Biological activity—inhibition of expression of c-raf kinase

T-24 cells are treated with an unmodified oligonucleotide or an oligonucleotide modified according to the present invention in a serum free optimem medium containing 10 μg/ml lipofectin (the oligonucleotides are applied directly into the medium). After a 4 hours incubation at 37° C. the medium containing the oligonucleotide is replaced by a normal medium free from oligonucleotide (McCoys medium+10% FCS). After 24 hours cell RNA is extracted and separated via guanidinium isothiocyanate methodology followed by the determination of c-raf RNA expression using a radiolabelled human c-DNA "probe". C-raf RNA is quantitiated using a phospho-imager.

What is claimed is:

1. An oligonucleotide of the formula I $$5'\text{-}(U)_n\text{-}3' \qquad (I),$$

in which U is an identical or different radical of a natural or a synthetic nucleoside and n is a number from 2 to 200 comprising at least one structural unit of two consecutive nucleosides, the structural unit comprising the formula IIa

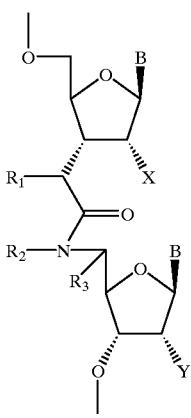
(IIa)

wherein $R_1$ is H, $C_1$–$C_4$alkyl or $C_1$–$C_4$alkoxy;

$R_2$ is H; $C_1$–$C_4$alkyl; phenyl; phenyl substituted with Oh, OR''', O(CH$_2$CH$_2$O)$_n$R''', $C_6$–$C_{10}$aryl or $C_3$–$C_9$heteroaryl; an intercalator; amino-$C_1$–$C_4$alkyl; $C_1$–$C_4$alkylamino; ammonium-$C_1$–$C_4$alkyl; $C_1$–$C_4$alkylammonium; amino-$C_1$–$C_r$alkylaminosulfonyl; $C_1$–$C_4$alkylamino-$C_1$–$C_4$alkylaminosulfonyl; or (CH$_3$)$_2$NCH$_2$CH$_2$;

$R_3$ is H or $C_1$–$C_4$alkyl;

R''' is $C_1$–$C_4$alkyl;

X is H, OH, O—$C_1$–$C_4$alkyl, —O—(CH$_2$—CH$_2$—O)$_m$H or —O—CH$_2$—C(OR)H—CH$_2$—OH;

Y is H, O—$C_1$–$C_4$alkyl, —O—(CH$_2$—CH$_2$—O)$_m$H or —O—CH$_2$—(OR)H—CH$_2$—OH;

r is H or $C_1$–$C_{10}$alkyl;

m is an integer from 1 to 4;

n is an integer from 1 to 4 and

B is a purine or pyrimidine radical with the proviso that either X or Y is H and that X and Y are not identical.

2. The oligonucleotide of claim 1 wherein the intercalator is anthraquinone connected via a linker.

3. The oligonucleotide of claim 2 wherein the linker is a chain of 2 to 7 atoms selected from the group consisting of C, N and O.

4. The oligonucleotide according to claim 1 in which B as a purine radical or an analogue thereof is a radical of the formula IV, IVa, IVb, IVc, IVd or Vd

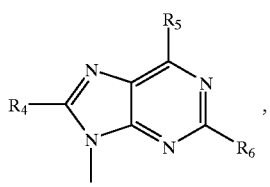
(IV)

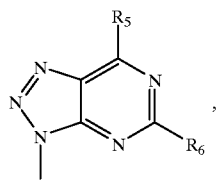
(IVa)

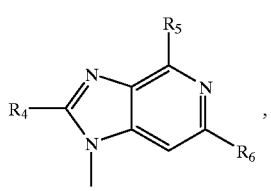
(IVb)

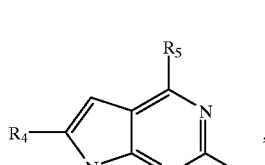
(IVc)

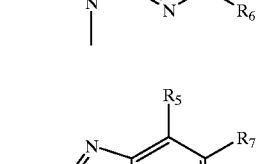
(IVd)

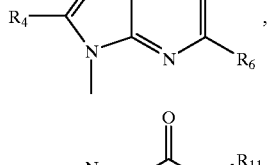
(IVe)

in which $R_4$ is H, Cl, Br or OH or —O-alkyl having 1 to 12 C atoms, and $R_5$, $R_6$ and $R_7$ independently of one another are H, OH, SH, NH$_2$, NHNH$_2$, NHOH, NHOalkyl having 1 to 12 C atoms, —N=CH—N($C_1$–$C_{12}$alkyl)$_2$, F, Cl, Br, alkyl or hydroxyalkyl or aminoalkyl or alkoxy or alkylthio having 1 to 12 C atoms, the hydroxyl and amino groups being unsubstituted or substituted by a protective group, phenyl, benzyl, primary amino having 1 to 20 C atoms or secondary amino having 2 to 30 C atoms, and $R_{11}$ is H or $C_1$–$C_4$alkyl.

5. The oligonucleotide according to claim 4, in which the protective group for hydroxyl and amino groups is $C_1$–$C_8$acyl.

6. The oligonucleotide according to claim 4, in which the primary amino contains 1 to 12 C atoms and the secondary amino 2 to 12 C atoms.

7. The oligonucleotide according to claim 4, in which the primary amino and secondary amino are radicals of the formula $R_8R_9N$ in which $R_8$ is H or, independently, has the meaning of $R_9$, and $R_9$ is $C_1$–$C_{20}$alkyl, -aminoalkyl or -hydroxyalkyl; carboxyalkyl or carbalkoxylalkyl, where the carbalkoxy group contains 2 to 8 C atoms and the alkyl group 1 to 6 C atoms; $C_2$–$C_{20}$alkenyl; phenyl, mono- or di($C_1$–$C_4$alkyl- or alkoxy)phenyl, benzyl, mono- or di($C_1$–$C_4$alkyl- or -alkoxy)benzyl; or 1,2-, 1,3- or 1,4-imidazolyl-$C_1$–$C_6$alkyl, or $R_8$ or $R_9$ together are tetra- or pentamenthylene, 3-oxa-1,5-pentylene, —CH$_2$—NR$_{10}$—

$CH_2CH_2$— or —$CH_2CH_2$—$NR_{10}$—$CH_2CH_2$—, in which $R_{10}$ is H or $C_1$–$C_4$alkyl, where the amino group in the aminoalkyl is unsubstituted or substituted by one or two $C_1$–$C_4$alkyl or -hydroxyalkyl groups, and the hydroxyl group in the hydroxyalkyl is free or etherified with $C_1$–$C_4$alkyl.

8. The oligonucleotide according to claim 6, in which the primary amino and secondary amino are methyl-, ethyl-, dimethyl-, diethyl-, allyl-, mono- or di(hydroxyeth-2-yl)-, phenyl-, benzyl-, acetyl-, isobutyryl- and benzoylamino.

9. The oligonucleotide according to claim 4, in which $R_4$ in the formulae IV, IVb, IVc, IVd and IVe is hydrogen.

10. The oligonucleotide according to claim 4, in which $R_7$ in formula IVd is hydrogen.

11. The oligonucleotide according to claim 4, in which $R_5$ and $R_6$ in the formulae IV, IVa, IVb, IVc, IVd and IVe independently of one another are H, F, Cl, Br, OH, SH, $NH_2$, NHOH, $NHNH_2$, methylamino, dimethylamino, benzoylamino, methoxy, ethoxy and methylthio.

12. The oligonucleotide according to claim 4, in which B is a purine radical or a radical of a purine analogue from the series consisting of adenine, N-methyladenine, N-benzoyladenine, 2-methylthioadenine, 2,-aminoadenine, 2-hydroxypurine, 2-amino-6-chloropurine, 2-amino-6-methylthiopurine, guanine and N-isobutyrlguanine.

13. The oligonucleotide according to claim 1, in which B as an analogous pyrimidine radical is a uracil, thymine or cytosine radical of the formulae V, Va and Vb

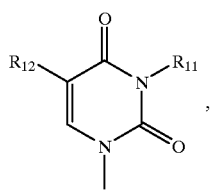

(V)

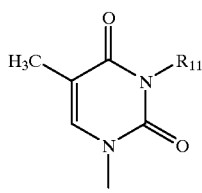

(Va)

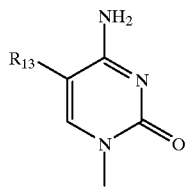

(Vb)

in which $r_{11}$ is H or $C_1$–$C_4$alkyl, and $R_{12}$ and $R_{13}$ independently of one another are H, F, Cl, Br, alkyl, propargyl or hydroxyalkyl or aminoalkyl or alkoxy or alkylthio having 1 to 12 C atoms, where the hydroxyl and amino groups are unsubstituted or substituted by a protective group, phenyl, benzyl, primary amino having 1 to 20 C atoms or secondary amino having 2 to 30 C atoms, and the hydrogen atoms of the $NH_2$ group in formula Vb are unsubstituted or substituted by $C_1$–$C_6$alkyl, benzoyl or benzyl, and the dihydro derivatives of the radicals of the formulae V, Va and Vb.

14. The oligonucleotide according to claim 13, in which $r_{12}$ is H, $C_1$–$C_6$alkyl or —hydroxyalkyl, F, Cl, Br, $NH_2$, benzoylamino, mono- or di-$C_1$–$C_6$-alkylamino.

15. The oligonucleotide according to claim 13, in which $R_{13}$ is H, $C_1$–$C_6$alkyl or -alkoxy or —hydroxyalkyl, F, Cl, Br, $NH_2$, benzoylamino, mono- or di-$C_1$–$C_6$-alkylamino.

16. The oligonucleotide according to claim 14, in which $R_{12}$ is H, F, Cl, Br, $NH_2$, $NHCH_3$, $N(CH_3)_2$ or $C_1$–$C_4$alkyl.

17. The oligonucleotide according to claim 16, in which $R_{13}$ is H, $C_1$–$C_4$alkyl, $NH_2$, $NHCH_3$ or $(CH_3)_2N$.

18. The oligonucleotide according to claim 13, wherein $R_{12}$ and $R_{13}$ independently from each other are propargyl.

19. The oligonucleotide according to claim 1, in which B as the radical of a pyrimidine analogue is derived from uracil, thymine, cytosine, 5-fluorouracil, 5-chlorouracil, 5-bromouracil, dihydrouracil or 5-methylcytosine.

20. The oligonucleotide according to claim 4 wherein the OH-protecting group is linear or branched $C_1$–$C_8$alkyl, $C_7$–$C_{18}$aralkyl, triphenylsilyl, alkyldiphenylsilyl, dialkylphenylsilyl or trialkylsilyl having 1 to 20 C atoms in the alkyl groups, —$(C_1$–$C_8$alkyl$)_2$Si—O—Si$(C_1$–$C_8$alkyl$)_2$—, $C_2$–$C_{12}$acyl, $R_{14}$—$SO_2$—, in which $R_{14}$ is $C_1$–$C_{12}$alkyl, $C_5$— or $C_6$cycloalkyl, phenyl, benzyl, $C_1$–$C_{12}$alkylphenyl, $C_1$–$C_{12}$alkylbenzyl, or is $C_1$–$C_{12}$alkoxycarbonyl, phenoxycarbonyl, benzyloxycarbonyl, methylphenoxycarbonyl or methylbenzyloxycarbonyl which is unsubstituted or substituted by F, Cl, Br, $C_1$–$C_4$alkoxy, tri($C_1$–$C_4$alkyl)silyl or $C_1$–$C_4$alkylsulfonyl, or 9-fluorenylmethoxycarbonyl.

21. The oligonucleotide according to claim 20, wherein the OH-protecting group is linear or branched $C_1$–$C_4$alkyl, $C_7$–$C_{18}$aralkyl, trialkylsilyl having 1 to 12 C atoms in the alkyl groups, —$(CH_3)_2$Si—O—Si$(CH_3)_2$—, —$(i$-$C_3H_7)_2$Si—O—Si$(iC_3H_7)_2$—, $C_2$–$C_8$acyl, $R_{14}$—$SO_2$—, in which $R_{14}$ is $C_1$–$C_6$alkyl, phenyl, benzyl, $C_1$–$C_4$alkylphenyl, $C_1$–$C_4$alkylbenzyl, halophenyl or halobenzyl, or is $C_1$–$C_8$alkoxycarbonyl, phenoxycarbonyl, benzyloxycarbonyl or 9-fluorenylmethoxycarbonyl.

22. The oligonucleotide according to claim 20, wherein the OH-protecting group is methyl, ethyl, n- or i-propyl, n-, i- or t-butyl; benzyl, methylbenzyl, dimethylbenzyl, methoxybenzyl, dimethoxybenzyl, bromobenzyl; diphenylmethyl, di(methylphenyl)-methyl, di(dimethylphenyl)methyl, di(methoxyphenyl)methyl, di(methoxyphenyl)-(phenyl)methyl, trityl, tri)methylphenyl)methyl, tri(dimethylphenyl)methyl, tri(methoxyphenyl)methyl, tri(dimethoxyphenyl)methyl; trimethylsilyl, triethylsilyl, tri-n-propylsilyl, i-propyldimethylsilyl, t-butyldimethylsilyl, t-butyldiphenylsilyl, n-octyldimethylsilyl, (1,1,2,2-tetramethylethyl)dimethylsilyl, —$(CH_3)_2$Si—O—Si$(CH_3)_2$—, —$(i$-$C_3H_7)_2$Si—O—Si$(iC_3H_7)_2$—; acetyl, propanoyl, butanoyl, pentanoyl, hexanoyl, benzoyl, methylbenzoyl, methoxybenzoyl, chlorobenzoyl or bromobenzoyl; methyl-, ethyl-, propyl-, butyl-, phenyl-, p-bromo-, p-methoxy- or p-methylphenylsulfonyl; methoxy-, ethoxy-, n- or i-propoxy- or n-, i- or t-butoxycarbonyl, or phenoxycarbonyl, benzyloxycarbonyl, methyl- or methoxy- or chlorophenoxycarbonyl or -benzyloxycarbonyl or 9-fluoroenylmethoxycarbonyl.

23. The oligonucleotide according to claim 1, comprising at least one structural unit of two consecutive nucleosides, the structural unit comprising the formula IIa wherein $R_1$ is H, $C_1$–$C_4$alkyl or $C_1$–$C_4$alkoxy; $R_2$ is H; $C_1$–$C_4$alkyl; phenyl; phenyl substituted with OH, OR''', O($CH_2CH_2O)_nR'''$, $C_6$–$C_{10}$aryl or $C_3$–$C_9$heteroaryl; an intercalator; amino-$C_1$–$C_4$alkyl; $C_1$–$C_4$alkylamino; ammonium-$C_1$–$C_4$alkyl; $C_1$–$C_4$alkylammonium; amino-$C_1$–$C_4$alkylaminosulfonyl; $C_1$–$C_4$alkylamino-$C_1$–$C_4$alkylaminosulfonyl or $(CH_3)_2NCH_2CH_2$; $R_3$ is H or $C_1$–$C_4$alkyl; R''' is $C_1$–$C_4$alkyl; X is H, OH, O—$C_1$–$C_4$alkyl, —O—$(CH_2$—$CH_2$—O$)_m$H or —O—$CH_2$—C(OR)H—$CH_2$—OH; Y is H, O—$C_1$–$C_4$alkyl, —O—$(CH_2$—$CH_2$—O$)_m$H or —O—CH$_2$—C(OR)H—CH$_2$—OH; R is H or C$_1$–C$_{10}$alkyl; m is an integer from 1 to 4; n is an integer from 1 to 4 and B is a purine or pyrimidine radical or an analogue thereof.

24. The oligonucleotide according to claim 23, wherein R$_1$ is H or C$_1$–C$_4$alkyl; R$_2$ is H; C$_1$–C$_4$alkyl; phenyl or phenyl substituted with OH, OR''', O(CH$_2$CH$_2$O)$_n$R''', C$_6$–C$_{10}$aryl or C$_3$–C$_9$heteroaryl; R$_3$ is H or C$_1$–C$_4$alkyl; R''' is C$_1$–C$_4$alkyl; X is H, OH, O—C$_1$–C$_4$alkyl, —O—(CH$_2$—CH$_2$—O)$_m$H or —O—CH$_2$—C(OR)H—CH$_2$—OH; Y is H, O—C$_1$–C$_4$alkyl, —O—(CH$_2$—CH$_2$—O)$_m$H or —O—CH$_2$—C(OR)H—CH$_2$—OH; r is H or C$_1$–C$_{10}$alkyl; m is an integer from 1 to 4; n is an integer from 1 to 4 and B is a purine or pyrimidine radical or an analogue thereof.

25. The oligonucleotide according to claim 24, wherein R$_1$ is H or C$_1$–C$_4$alkyl; R$_2$ is H; C$_1$–C$_4$alkyl or phenyl; R$_3$ is H or C$_1$–C$_4$alkyl; X is H, OH, O—C$_1$–C$_4$alkyl, —O—(CH$_2$—CH$_2$—O)$_m$H or —O—CH$_2$—C(OR)H—CH$_2$—OH; Y is H, O—C$_1$–C$_4$alkyl, —O—(CH$_2$—CH$_2$O)$_m$H or —O—CH$_2$—C(OR)H—CH$_2$—OH; R is H or C$_1$–C$_{10}$alkyl; m is an integer from 1 to 4; n is an integer from 1 to 4 and B is a purine or pyrimidine radical or an analogue thereof.

26. The oligonucleotide according to claim 25, wherein R$_1$ is H or C$_1$–C$_4$alkyl; R$_2$ is H; C$_1$–C$_4$alkyl or phenyl; R$_3$ is H or C$_1$–C$_4$alkyl; X is H, OH or O—C$_1$–C$_4$alkyl; Y is H or O—C$_1$–C$_4$alkyl; and B is a purine or pyrimidine radical or an analogue thereof.

27. The oligonucleotide according to claim 26, wherein R$_1$ is H; r$_2$ is H or phenyl; R$_3$ is H or methyl; X is H or O—CH$_3$; Y is H or O—CH$_3$; and B is a pyrimidine radical or an analogue thereof.

28. A pharmaceutical preparation comprising an effective amount of an oligonucleotide according to claim 1 on its own or together with other active ingredients, a pharmaceutical carrier and, if appropriate, excipients.

29. The oligonucleotide of claim 1, comprising at least one structural unit of two consecutive nucleosides, the structural unit comprising the formula IIa.

30. A method diagnosing viral infection or genetically related diseases comprising:
selectively interacting the oligonucleotides of claim 1 with a tissue sample derived from a mammal including humans.

31. A therapeutic method for the treatment of diseases in a mammal including humans comprising:
interacting the oligonucleotide of claim 1 with nucleotide sequences in the body of said mammal.

32. A nucleotide dimer of the formula IIIa

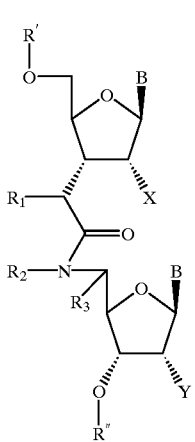

(IIIa)

wherein
R$_1$ is H, C$_1$–C$_4$alkyl or C$_1$–C$_4$alkoxy;

R$_2$ is H; C$_1$–C$_4$alkyl; phenyl; phenyl substituted with OH, OR''', O(CH$_2$CH$_2$O)$_n$R''', C$_6$–C$_{10}$aryl or C$_3$–C$_9$heteroaryl; an intercalator; amino-C$_1$–C$_4$alkyl; C$_1$–C$_4$alkylamino; ammonium-C$_1$–C$_4$alkyl; C$_1$–C$_4$alkylammonium; amino-C$_1$–C$_4$alkylaminosulfonyl; C$_1$–C$_4$alkylamino-C$_1$–C$_4$alkylaminosulfonyl; or (CH$_3$)$_2$NCH$_2$CH$_2$;

R$_3$ is H or C$_1$–C$_4$alkyl;

R' and R'' are H or an OH-protecting group or R'' is a radical forming a phosphorus-containing nucleotide bridge group;

R''' is C$_1$–C$_4$alkyl;

X is H, OR$_x$, O—C$_1$–C$_4$alkyl, —O—(CH$_2$—CH$_2$—O)$_m$H or —O—CH$_2$—C(OR)H—CH$_2$—OR$_x$;

Y is H, O—C$_1$–C$_4$alkyl, —O—(CH$_2$—CH$_2$—O)$_m$H or —O—CH$_2$—C(OR)H—CH$_2$—OH;

R is H or C$_1$–C$_{10}$alkyl;

R$_x$ is H or an OH-protecting group;

m is an integer from 1 to 4;

n is an integer from 1 to 4 and

B is a purine or pyrimidine radical with the proviso that either X or Y is H and that X and Y are not identical.

33. The dimer according to claim 32 wherein the phosphorus-containing nucleotide bridge group is a radical of the formula

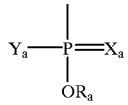

in which Y$_a$ is hydrogen, C$_1$–C$_{12}$alkyl, C$_6$–C$_{12}$aryl, C$_7$–C$_{20}$alkaryl, —OR$_b$, —SR$_b$, —NH$_2$, primary amino, secondary amino, O$^\ominus$M$^\oplus$ or S$^\ominus$M$^\oplus$; X$_a$ is oxygen or sulfur; R$_a$ is hydrogen, M$^\ominus$, C$_1$–C$_{12}$alkyl, C$_2$–C$_{12}$alkenyl or C$_6$–C$_{12}$aryl, or the group R$_a$O is N-heteroaryl-N-yl having 5 ring members and 1 to 3 N atoms; R$_b$ is hydrogen, C$_1$–C$_{12}$alkyl or C$_6$–C$_{12}$aryl; and Mj$^\oplus$ is Na$^\oplus$, K$^\oplus$, Li$^\oplus$, NH$_4$$^\oplus$ or primary, secondary, tertiary or quaternary ammonium; where alkyl, aryl, aralkyl and alkaryl in Y$_a$, R$_a$ and R$_b$ are unsubstituted or substituted by alkoxy, alkylthio, halogen, —CN, —NO$_2$, phenyl, nitrophenyl or halophenyl.

34. The dimer according to claim 32, wherein the bridge group R'' is —P(O)O$^\ominus$—, —P(O)S$^\ominus$—, —P(S)S$^\ominus$—, —P(O)R$_{16}$—, —P(O)NR$_{17}$R$_{18}$—, or —CH$_2$—, in which R$_{16}$ is H or C$_1$–C$_6$alkyl, and R$_{17}$ and R$_{18}$ independently of one another have the meaning of R$_{16}$.

35. The dimer according to claim 34, wherein the bridge group is —P(O)O$^\ominus$—.

36. The dimer according to claim 32, comprising the formula IIIa, wherein R$_1$ is H, C$_1$–C$_{alkyl\ or\ C1}$–C$_4$alkoxy; R$_2$ is H; C$_1$–C$_4$alkyl; phenyl; phenyl substituted with OH, OR''', O(CH$_2$CH$_2$O)$_n$R''', C$_6$–C$_{10}$aryl or C$_3$–C$_9$heteroaryl; an intercalator; amino-C$_1$–C$_4$alkyl; C$_1$–C$_4$alkylamino; ammonium-C$_1$–C$_4$alkyl; C$_1$–C$_4$alkylammonium; amino-C$_1$–C$_4$alkylaminosulfonyl; C$_1$–C$_4$alkylamino-C$_1$–C$_4$alkylaminosulfonyl or (CH$_3$)$_2$NCH$_2$CH$_2$; R$_3$ is H or C$_1$–C$_4$alkyl; R''' is C$_1$–C$_4$alkyl; X is H, OR$_x$, O—C$_1$–C$_4$alkyl, —O—(CH$_2$—CH$_2$—O)$_m$H or —O—CH$_2$—C(OR)H—CH$_2$—OR$_x$; Y is H, O—C$_1$–C$_4$alkyl, —O—(CH$_2$—CH$_2$—O)$_m$H or —O—CH$_2$—C(OR)H—CH$_2$—OH; R is H or C$_1$–C$_{10}$alkyl; R$_x$ is H or an OH-protecting group; m is an integer from 1 to 4; n is an integer from 1 to 4 and B is a purine or pyrimidine radical.

37. The dimer according to claim 36, wherein R$_1$ is H or C$_1$–C$_4$alkyl; R$_2$ is H; C$_1$–C$_4$alkyl; phenyl or phenyl substituted with OH, OR'", O(CH$_2$CH$_2$O)$_n$R'", C$_6$–C$_{10}$aryl or C$_3$–C$_9$heteroaryl; R$_3$ is H or C$_1$–C$_4$alkyl; R'" is C$_1$–C$_4$alkyl; X is H, OR$_x$, O—C$_1$–C$_4$-alkyl, —O—(CH$_2$—CH$_2$—O)$_m$H or —O—CH$_2$—C(OR)H—CH$_2$—OR$_x$; Y is H, O—C$_1$–C$_4$alkyl, —O—(CH$_2$—CH$_2$—O)$_m$H or —O—CH$_2$—C(OR)H—CH$_2$—OH; R is H or C$_1$–C$_{10}$alkyl; R$_x$ is H or an OH-protecting group; m is an integer from 1 to 4; n is an integer from 1 to 4 and B is a purine or pyrimidine radical.

38. The dimer according to claim 37, wherein R$_1$ is H or C$_1$–C$_4$alkyl; R$_2$ is H; C$_1$–C$_4$alkyl or phenyl; R$_3$ is H or C$_1$–C$_4$alkyl; X is H, OR$_x$, O—C$_1$–C$_4$alkyl, —O—(CH$_2$—CH$_2$—O)$_m$H or —O—CH$_2$—C(OR)H—CH$_2$—OR$_x$; Y is H, O—C$_1$–C$_4$alkyl, —O—(CH$_2$—CH$_2$—O)$_m$H or —O—CH$_2$—C(OR)H—CH$_2$OH; R is H or C$_1$–C$_{10}$alkyl; R$_x$ is H or an OH-protecting group; m is an integer from 1 to 4; n is an integer from 1 to 4 and B is a purine or pyrimidine radical.

39. The dimer according to claim 38, wherein R$_1$ is H or C$_1$–C$_4$alkyl; R$_2$ is H; C$_1$–C$_4$alkyl or phenyl; R$_3$ is H or C$_1$–C$_4$alkyl; X is H, OR$_x$ or O—C$_1$–C$_4$alkyl; Y is H or O—C$_1$–C$_4$alkyl; R$_x$ is H or an OH-protecting group; and B is a purine or pyrimidine radical.

40. The dimer according to claim 39, wherein R$_1$ is H; R$_2$ is H or phenyl; R$_3$ is H methyl; X is H or O—CH$_3$; Y is H or O—CH$_3$; and B is a pyrimidine radical.

41. A process for the preparation of a dimer according to claim 28 which comprises
a compound of the formula VI

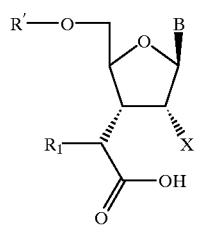

(VI)

wherein
R$_1$ is H, C$_1$–C$_4$alkyl or C$_1$–C$_4$alkoxy; R' is H or an OH-protecting group; X is H, OR$_x$, O—C$_1$–C$_4$alkyl, —O—(CH$_2$—CH$_2$—O)$_m$H— or —O—CH$_2$—C(OR) H—CH$_2$—OR$_x$; R is H or C$_1$–C$_{10}$alkyl; R$_x$ is H or an OH-protecting group and B is a purine or pyrimidine radical; is reacted with a compound of the VII

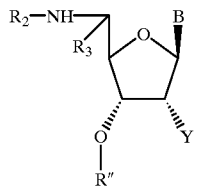

(VII)

wherein

R$_2$ is H; C$_1$–C$_4$alkyl; phenyl; phenyl substituted with OH, OR'", O(CH$_2$CH$_2$O)$_n$R'", C$_6$–C$_{10}$aryl or C$_3$–C$_9$heteroaryl; an intercalator; amino-C$_1$–C$_4$alkyl; C$_1$–C$_4$alkylamino; ammonium-C$_1$–C$_4$alkyl; C$_1$–C$_4$alkylammonium; amino-C$_1$–C$_4$alkyl-aminosulfonyl; C$_1$–C$_4$alkylamino-C$_1$–C$_4$alkylaminosulfonyl; or (CH$_3$)$_2$NCH$_2$CH$_2$; R$_3$ is H or C$_1$–C$_4$-alkyl; R" is H or an OH-protecting group or a radical forming a phosphorous-containing nucleotide bridge group; R'" is C$_1$–C$_4$alkyl; Y is H, O—C$_1$–C$_4$alkyl, —O—(CH$_2$—CH$_2$—O)$_m$H or —O—CH$_2$—C(OR)H—CH$_2$—OH: and B is a purine or pyrimidine radical.

42. A method of preparing oligonucleotides which comprise one or more identical or different dimer units of compounds of the formulae IIIa comprising:

contacting the dimer of claim 32 with monomer units wherein the oligonucleotides prepared have 2 to 200 monomer units.

43. The method according to claim 42 wherein said oligonucleotides have 2 to 100 monomer units.

44. The method according to claim 43 wherein said oligonucleotides have 2 to 50 monomer units.

45. The according to claim 44 wherein said oligonucleotides have 2 to 20 monomer units.

* * * * *

UNITED STATES PATENT AND TRADEMARK OFFICE
CERTIFICATE OF CORRECTION

PATENT NO.   : 6,066,447
DATED        : May 23, 2000
INVENTOR(S)  : De Mesmaeker et al.

It is certified that error appears in the above-identified patent and that said Letters Patent is hereby corrected as shown below:

Column 63,
Claim 1, line 25, "Oh" should be changed to -- OH --.
Claim 1, line 30, "$C_r$" should be changed to -- $C_4$ --.
Claim 1, line 42, "r" should be changed to -- R --.
Claim 4, line 57, "Vd" should be changed to -- IVe --.

Column 64, claim 7,
Line 67, "pentamenthylene" should be changed to -- pentamethylene --.

Column 65, claim 14,
Line 66, "$r_{12}$" should be changed to -- $R_{12}$ --.

Column 66, claim 22,
Line 50, after the word "phenyl-," insert the word -- benzyl-, --.

Column 67,
Claim 24, line 10, "r" should be changed to -- R --.
Claim 27, line 27, "$r_2$" should be changed to -- $R_2$ --.
Claim 30, line 36, after the word "method", insert the word -- of --.

Column 68, claim 33,
Line 34, before "$C_7$-$C_{20}$arkaryl," insert -- $C_7$-$C_{20}$aralkyl, --.
Line 36, "$M^\ominus$" should be changed to -- $M^\oplus$ --.
Line 39, "$Mj^\ominus$" should be changed to -- $M^\oplus$ --

Column 69, claim 40,
Line 23, before the word "methyl", insert the word -- or --.

UNITED STATES PATENT AND TRADEMARK OFFICE
CERTIFICATE OF CORRECTION

PATENT NO. : 6,066,447
DATED : May 23, 2000
INVENTOR(S) : De Mesmaeker et al.

It is certified that error appears in the above-identified patent and that said Letters Patent is hereby corrected as shown below:

<u>Column 70, claim 45,</u>
Line 39, after the word "The", insert the word -- method --.

Signed and Sealed this

Thirteenth Day of November, 2001

Attest:

*Nicholas P. Godici*

NICHOLAS P. GODICI
*Attesting Officer*  *Acting Director of the United States Patent and Trademark Office*

SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<221> NAME/KEY: modified_base
<222> LOCATION: (4)
<223> OTHER INFORMATION: n is Tb as shown on page 79 of the
      specification
<220> FEATURE:
<223> OTHER INFORMATION: Description of Artificial Sequence:
      Oligonucleotide

<400> SEQUENCE: 1
tttntctctc tctct                                                    15

<210> SEQ ID NO 2
<211> LENGTH: 16
<212> TYPE: DNA
<213> ORGANISM: Artificial Sequence
<220> FEATURE:
<221> NAME/KEY: modified_base
<222> LOCATION: (4)..(12)
<223> OTHER INFORMATION: n is Tb as shown on page 79 of the
      specification
<220> FEATURE:
<223> OTHER INFORMATION: Description of Artificial Sequence:
      Oligonucleotides

<400> SEQUENCE: 2
gcgntntntn tntgcg                                                   16

<210> SEQ ID NO 3
<211> LENGTH: 15
<212> TYPE: DNA
<213> ORGANISM: Artificial Sequence
<220> FEATURE:
<221> NAME/KEY: modified_base
<222> LOCATION: (10)..(12)
<223> OTHER INFORMATION: n is Tb as shown on page 79 of the
      specification
<220> FEATURE:
<223> OTHER INFORMATION: Description of Artificial Sequence:
      Oligonucleotides

<400> SEQUENCE: 3
cgactatgca ntntc                                                    15
      82